United States Patent
Lenker et al.

(10) Patent No.: US 9,993,266 B2
(45) Date of Patent: Jun. 12, 2018

(54) STEERABLE ENDOLUMINAL PUNCH

(71) Applicant: Indian Wells Medical, Inc., Laguna Beach, CA (US)

(72) Inventors: Jay A. Lenker, Laguna Beach, CA (US); Michael L. Jones, San Clemente, CA (US); James A. Carroll, Laguna Beach, CA (US)

(73) Assignee: Indian Wells Medical, Inc., Laguna Beach, CA (US)

( * ) Notice: Subject to any disclaimer, the term of this patent is extended or adjusted under 35 U.S.C. 154(b) by 321 days.

(21) Appl. No.: 14/851,941

(22) Filed: Sep. 11, 2015

(65) Prior Publication Data

US 2016/0100860 A1 Apr. 14, 2016

Related U.S. Application Data

(60) Provisional application No. 62/146,891, filed on Apr. 13, 2015, provisional application No. 62/135,103, filed on Mar. 18, 2015, provisional application No. 62/050,093, filed on Sep. 13, 2014.

(51) Int. Cl.
| | |
|---|---|
| *A61B 17/34* | (2006.01) |
| *A61B 17/00* | (2006.01) |
| *A61M 25/06* | (2006.01) |
| *A61B 17/3205* | (2006.01) |

(52) U.S. Cl.
CPC .... *A61B 17/3478* (2013.01); *A61B 17/32053* (2013.01); *A61B 2017/00247* (2013.01); *A61B 2017/00309* (2013.01); *A61B 2017/00314* (2013.01); *A61B 2017/00323* (2013.01); *A61B 2017/00867* (2013.01); *A61M 25/0606* (2013.01); *A61M 2025/0681* (2013.01)

(58) Field of Classification Search
CPC .......... A61B 17/3478; A61B 17/32053; A61B 2017/00247; A61B 2017/00309; A61B 2017/00314; A61B 2017/00318; A61B 2017/00323; A61B 2017/00327
See application file for complete search history.

(56) References Cited

U.S. PATENT DOCUMENTS

| | | | |
|---|---|---|---|
| 6,685,679 B2 * | 2/2004 | Merdan ............. | A61M 25/0043 604/264 |
| 2015/0320437 A1 * | 11/2015 | Worrell .............. | A61B 18/1445 606/169 |

* cited by examiner

*Primary Examiner* — Ashley Fishback
(74) *Attorney, Agent, or Firm* — K. David Crockett, Esq.; Crockett & Crockett, PC

(57) ABSTRACT

An endoluminal needle or punch is describes wherein the distal end of the endoluminal needle is able to articulate laterally out of the longitudinal axis of the steerable endoluminal needle. The endoluminal needle further comprise a blunted distal end configuration that is minimally traumatic. Under control by the user, at the proximal end of the endoluminal needle, a sharp stylet can be advanced to punch tissue and then be retracted to maximize safety. The endoluminal needle is configured for use within an introducer.

19 Claims, 40 Drawing Sheets

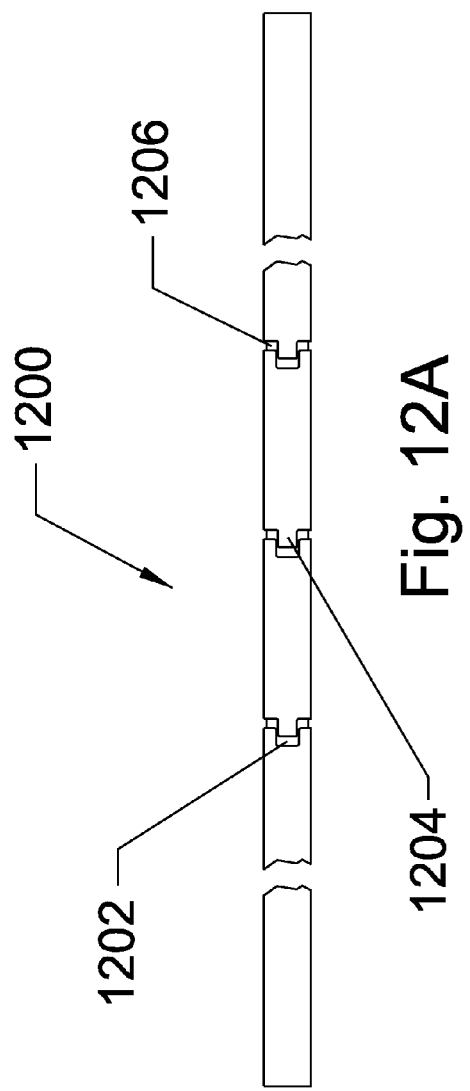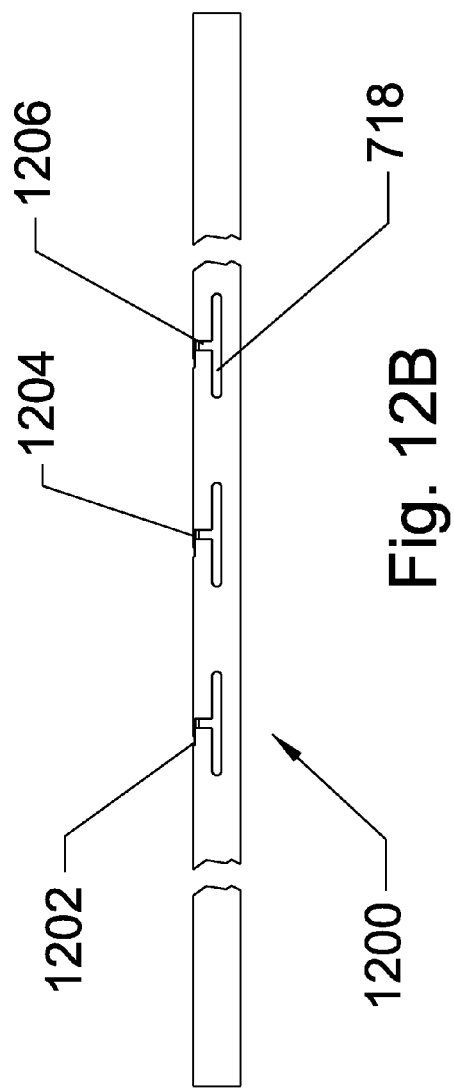

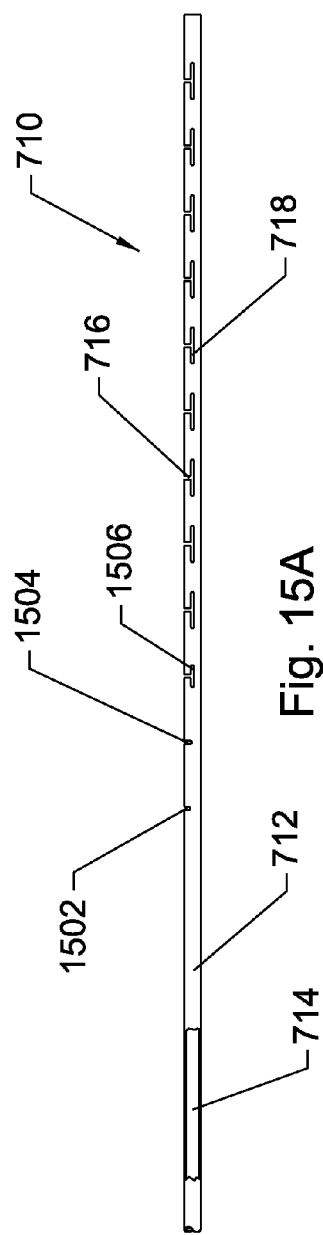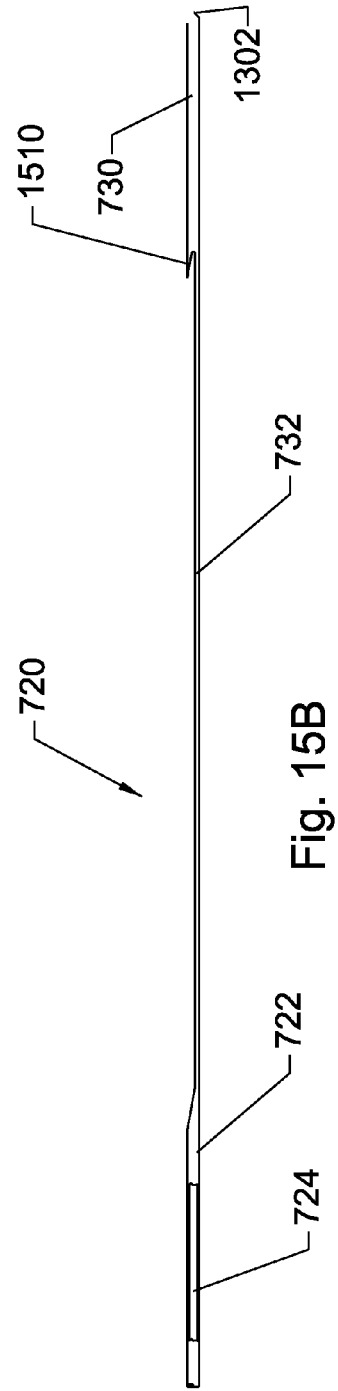

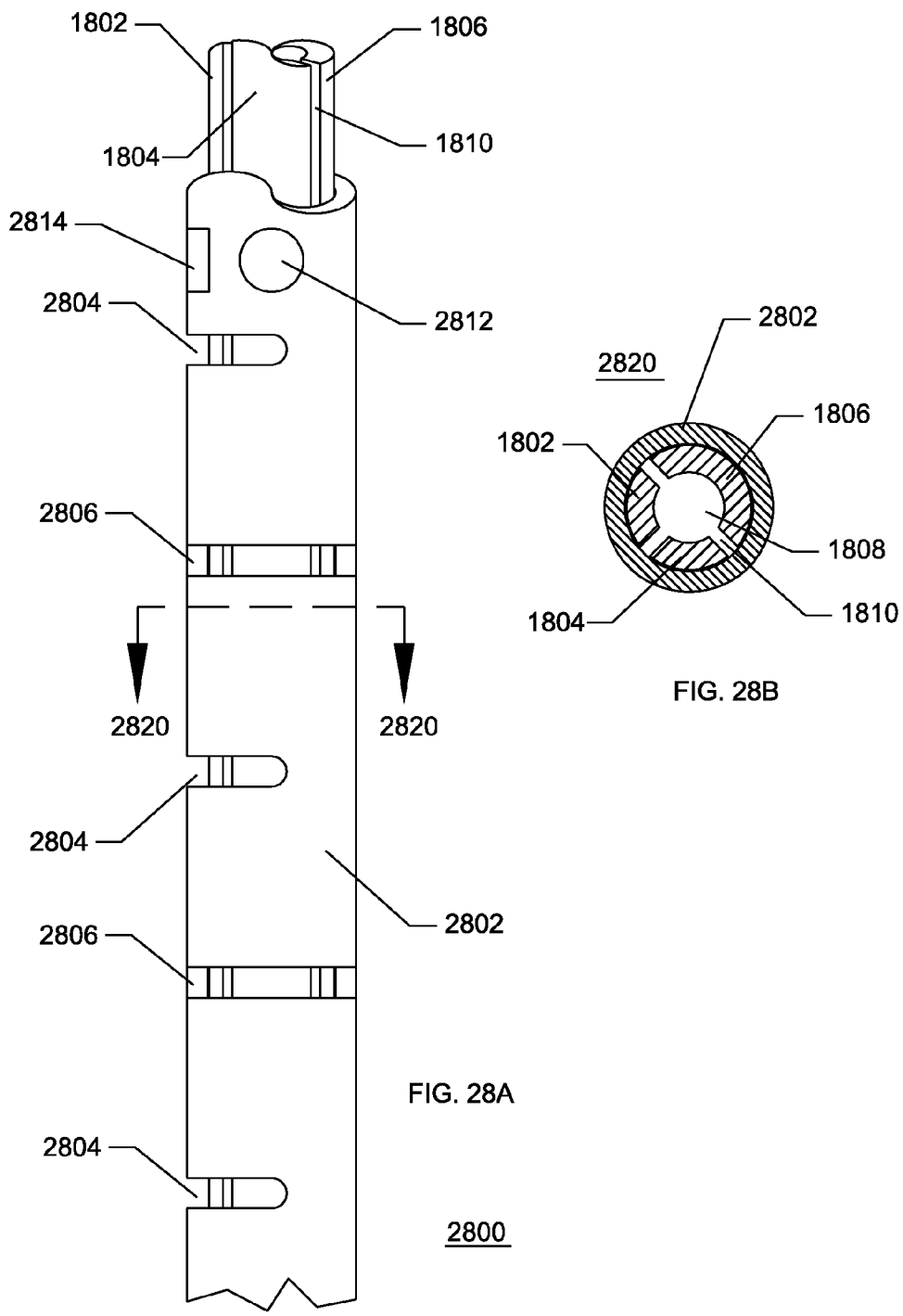

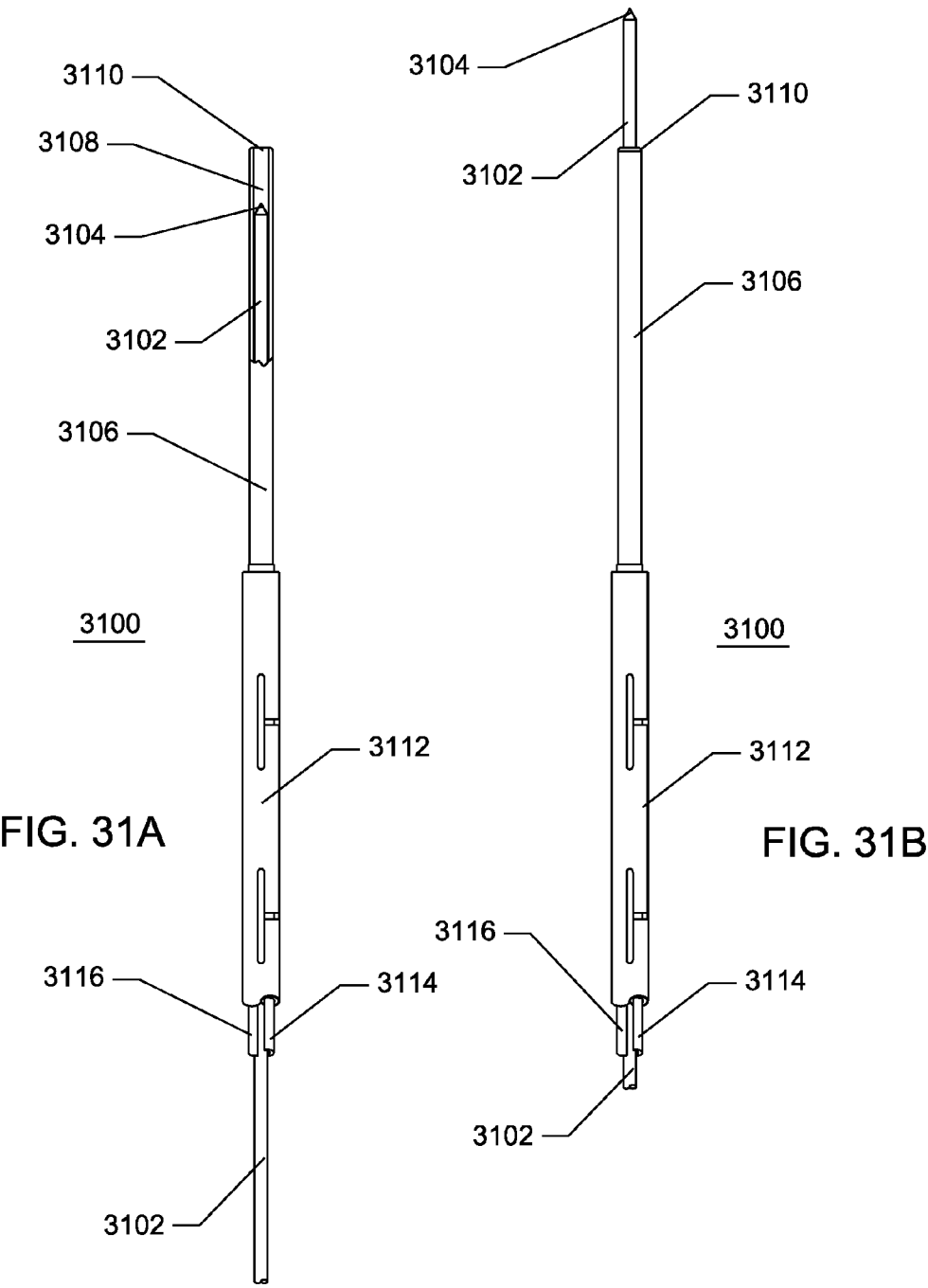

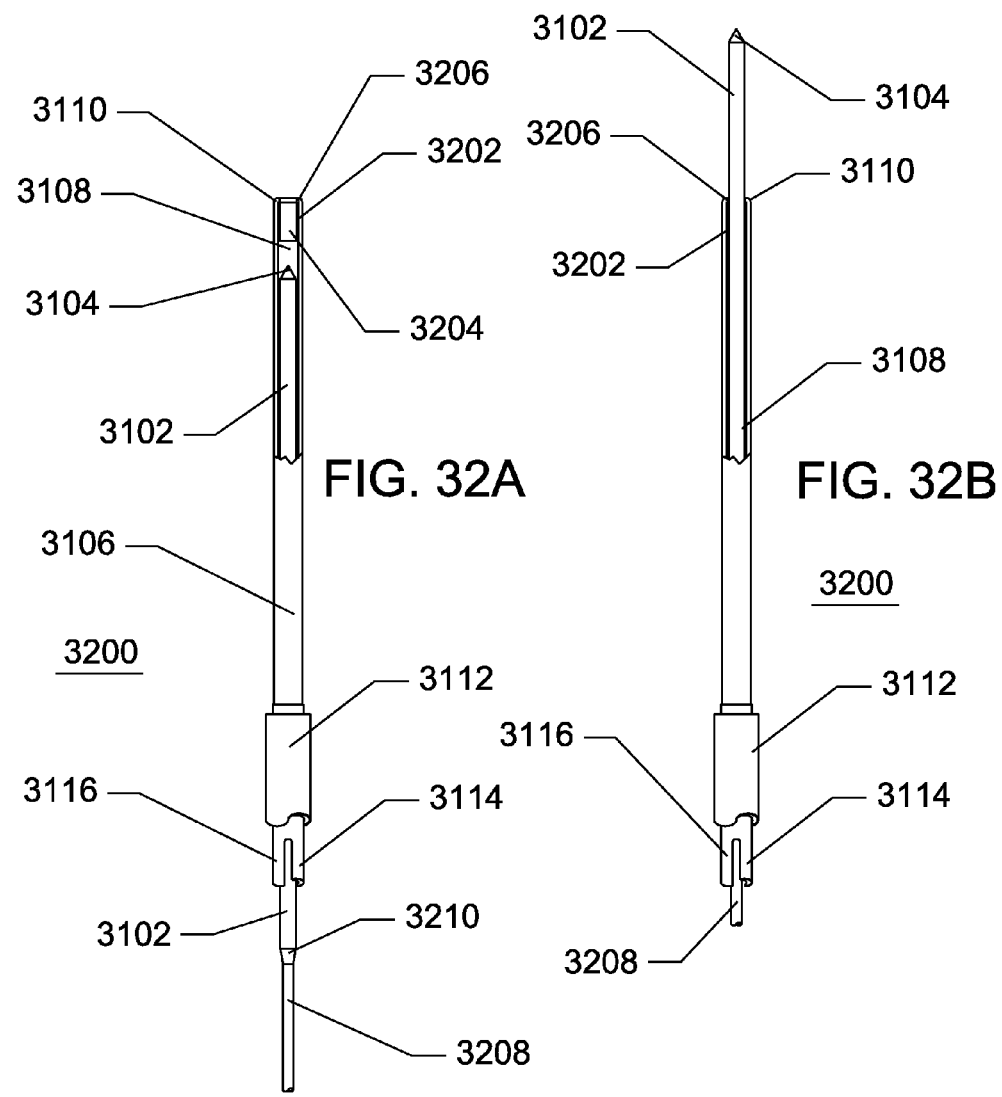

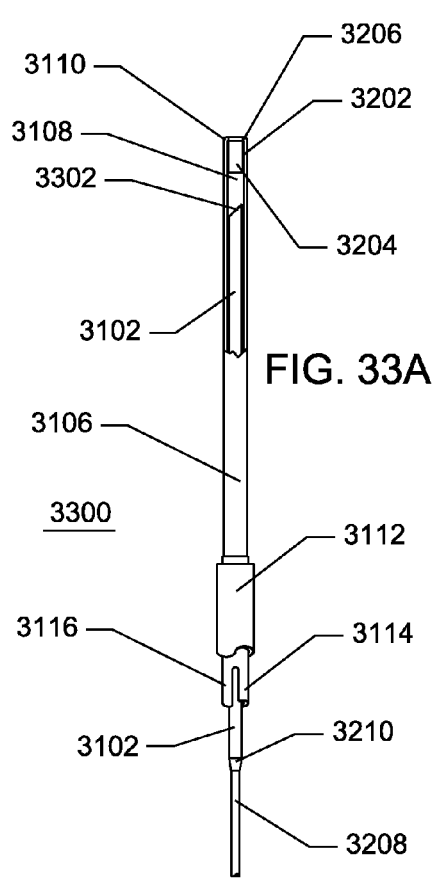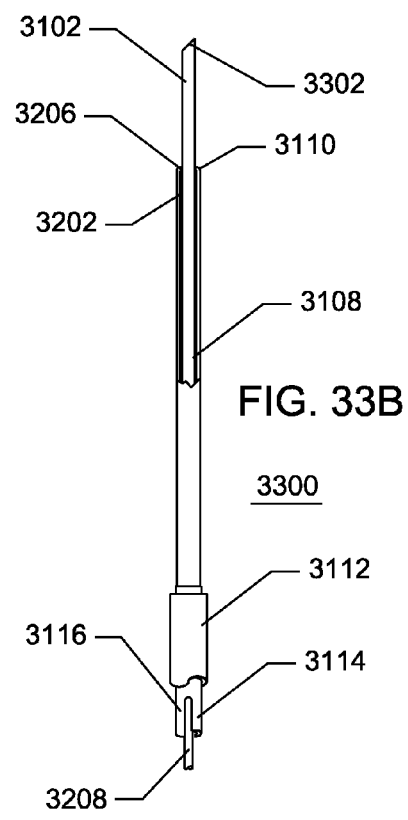

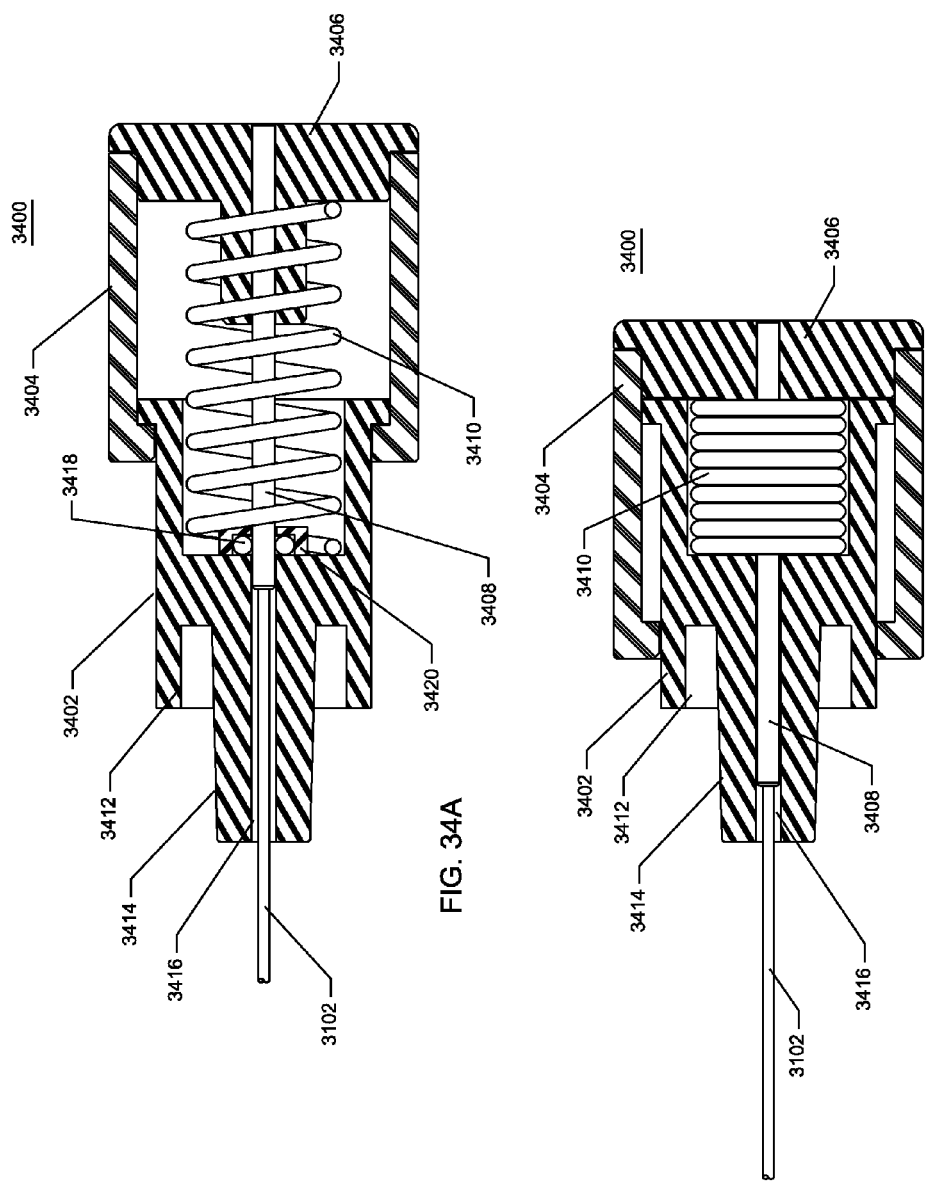

STEERABLE ENDOLUMINAL PUNCH

This application claims priority to U.S. Provisional Application 62/050,093, filed Sep. 13, 2014, U.S. Provisional Application 62/135,103, filed Mar. 18, 2015 and U.S. Provisional Application 62/146,891, filed Apr. 13, 2015, the entirety of each of which is hereby incorporated by reference.

FIELD OF THE INVENTION

The inventions described below relate to endoluminal punches and needles.

BACKGROUND

The currently accepted procedure for left atrial access involves routing a needle called a Brockenbrough needle into the right atrium with the Brockenbrough needle pre-placed within a guiding catheter. The guiding catheter specifically preferred for use with a Brockenbrough needle is called a Mullins catheter or transseptal introducer. The Brockenbrough needle is a long, small diameter punch, generally formed from a stainless steel wire stylet that is surrounded by a stainless steel tube.

The Brockenbrough needle, a relatively rigid structure, is operated by advancing the device, with its stylet wire advanced to blunt the sharp tip, within its guiding catheter through the inferior vena cava and into the superior vena cava. Under fluoroscopic guidance, the Brockenbrough needle, retracted inside the distal tip of the Mullins catheter, is withdrawn caudally into the right atrium until it falls or translates medially into the Fossa Ovalis. The Brockenbrough needle can then be advanced out the tip of the Mullins catheter to punch the cardiac tissue.

A main disadvantage of this system is that the Brockenbrough needle system is pre-curved at its distal end and is relatively rigid. This pre-curving, rigidity, and necessary distal sharpness causes the Brockenbrough needle system to carve material from the interior wall of the otherwise straight guiding catheter when the Brockenbrough needle assembly is inserted therethrough. The material carved from the guide catheter could potentially be released into the cardiovascular system and generate emboli with any number of serious clinical sequelae. Should this embolic catheter material enter the left atrium it could flow into and block important arterial vasculature such as the coronary arteries or cerebrovasculature. Furthermore, advancing a pre-curved, rigid punch through the cardiovascular system is difficult and could potentially damage the vessel wall or any number of significant cardiovascular structures, during the advancement.

SUMMARY

It is desirable to have a Brockenbrough needle system that is initially straight and then becomes curved under user control after being inserted into the guiding catheter. Such a straight Brockenbrough configuration is advantageous during ex-vivo insertion as well as insertion after the guide catheter has already been placed into the cardiovascular system. During ex-vivo insertion, the debris can be flushed from the lumen of the guide catheter but complete removal is not assured and emboli can still be generated by the device. However, if the guide catheter has already been inserted into the cardiovascular system, the debris cannot be flushed out ahead of time and could easily flow toward or be released into the cardiovascular system with potentially catastrophic or fatal results. Furthermore, the needle or punch can be more easily advanced into the body lumen if it were not pre-curved. Furthermore, it is beneficial that the needle comprise an adjustable curvature once it is located within the vasculature so that the user can modify the curve, in situ. This ability to articulate the distal end of the transseptal needle can be termed articulation.

In some embodiments, the steerability, deflection, or articulation, of a distal region of the device can be accomplished using the inner tube and outer tube, concentrically arranged and radially constrained together. The inner tube outer diameter is a close tolerance fit to the inside diameter of the outer tube but the inner tube is free to translate along a longitudinal axis of the tubes relative to the outer tube. Thus, only translational motion along the longitudinal axis is used to generate the articulation. The inner tube is modified in a region proximate the distal end such that the inner tube is divided, weakened, or split, into two or more parts. Only a portion of these divided parts of the inner tube are affixed, at their proximal end, to the more proximal portion of the inner tube. The parts of the inner tube not affixed at their proximal end can be optionally affixed near their distal end to the portions of the inner tube that are also affixed at their proximal end. The outer tube is rendered flexible by cutting slots or gaps generally having a lateral or radial orientation, although there can be some projection at an angle or along the longitudinal axis of the outer tube. These lateral slots do not pass completely through the outer tubing so a spine with ribs is formed in the outer tubing. The inner tube is affixed to the outer tube at a region distal to the lateral slots in the outer tube. The portion of the inner tube that is affixed to the outer tube is that portion of the split inner tube that is connected at its proximal end to the more proximal portions of the inner tube.

The articulation is generated by an outer tube that is modified to increase flexibility within a pre-determined longitudinal region. The articulation is controlled by one or more control rods disposed within the lumen of the tube. The control rod or rods can run the entire length of the exposed device distal to the hub, or the control rod or rods can run at least a portion of the distance of the pre-determined longitudinal region of increased flexibility, the bending zone. The control rod or rods can be integral to, or affixed, at their proximal ends to the hub, to an anchor within the hub, to a control mechanism comprising mechanical advantage, or to an intermediate member that transfers energy to the control rod or rods. The control rod or rods can be affixed to a point substantially distal to the bending zone or they can be integral or affixed to an intermediate member that is then affixed to the outer tube at a location distal to the bending zone.

Thus, articulation can also be generated using a plurality of (two or more) nested, radially constrained, substantially concentric axially translating tubes, wherein a first tube is weakened on one side to increase flexibility and limit final curvature and shape while a second tube is split substantially longitudinally and broken off on one side within the region where the first tube is also weakened. In certain embodiments, both tubes are substantially in place to maintain hoop strength, column strength, kink resistance, and orientation of discreet structures, such as breaks or slots exist within the plurality of tubes.

In certain embodiments, the steerable transseptal needle can comprise a stylet that comprises a sharp distal end. The sharp distal end can comprise a conical or beveled distal tip. The conical tip embodiment can comprise an angle of about 10 degrees to about 60 degrees from the longitudinal axis with a preferred angle of about 15 to about 30 degrees. The beveled tip embodiment can comprise an angle of about 10 degrees to about 60 degrees from the longitudinal axis. The sharp tip can, in other embodiments, comprise facets, pyramidal shapes, or the like.

In the embodiments that include a sharp stylet distal tip, the distal end of the inner tube and outer tube are generally blunted to the extent possible to render them minimally traumatic. The transition between the outer tube and the inner tube can comprise a tapered conical fairing, or it can comprise a rounded fillet, or the like. The distal end of the inner tube can comprise a rounded fillet, a blunted taper, or the like. The blunted taper can comprise angles ranging from about 45 degrees to about 90 degrees from the longitudinal axis.

The stylet can be routed through the central lumen of the inner tube and any control rods and keepers comprised within the outer tube. The stylet can comprise wire having a diameter of about 0.013 to about 0.030 inches in diameter with a preferred diameter of about 0.015 to about 0.025 inches in diameter with a more preferred diameter of about 0.016 to 0.022 inches in diameter. The stylet can comprise an area of reduced diameter within the region where the steerable transseptal needle is articulated, this reduced diameter reducing the bending resistance of the stylet in the flexible region.

The diameter of the stylet wire can be configured to permit fluid to be injected around the stylet but through the steerable transseptal needle internal lumen, even while the stylet wire is in place within the lumen. Furthermore, the annular lumen around the stylet can be configured to be sufficient to permit pressure measurements to be made through the central lumen of the steerable transseptal introducer while the stylet is in place. These pressure measurements and fluid injections can be facilitated by removal of the stylet from the steerable transseptal introducer. In a preferred embodiment, a central lumen of 0.023 inches diameter can surround a stylet having a diameter of about 0.016 to 0.020 inches in diameter. Thus, a lumen of about 0.035 to about 0.015 inches, radially, can exist within the steerable transseptal needle while the stylet is in place.

In other embodiments, the stylet wire can retain a reduced area, cross sectional shape comprising, but not limited to, half (or partial) circle, C-shape, cross-shape, or the like. The stylet wire can comprise these shapes to reduce the area of the lumen within the inner tube, control rods, and keepers, which are configured to maximize flow rate of fluids injected around the stylet wire. The reduced cross-sectional area of the stylet wire can continue along its entire length, or a portion thereof. In some embodiments, the reduced cross-section is eliminated and transitions to a full (or nearly full) circular cross-section at or near the distal end such that any protrusion outside of the inner tube lumen is substantially round and able to dilate tissue being punctured.

The hub at the proximal end of the stylet can preferably be removably affixed to the proximal female Luer lock connector on the steerable transseptal needle with a male Luer lock, quick disconnect, or other fastener. The stylet hub can comprise a spring-loaded actuator which is biased to withdraw the stylet tip proximally so it does not project out the distal end of the steerable transseptal needle. When the spring loaded button is depressed, or actuated, by the user, the sharp stylet tip protrudes out the distal end of the steerable transseptal needle sufficiently to penetrate tissue. Release of the spring-loaded button or actuator causes retraction of the sharp stylet distal tip within the blunted distal end of the steerable transseptal needle.

The hub of the steerable transseptal introducer can comprise a side port with a female Luer lock fitting to permit infusion or withdrawal of fluids or measurement of pressure while the stylet hub is locked in place and protruding axially through the steerable transseptal needle. The side port lumen is operably connected to the central lumen in the hub of the steerable transseptal needle. The side port can further comprise a valve such as a stopcock or a hemostasis valve to prevent unwanted fluid ingress or egress from the central lumen of the steerable transseptal needle. In some embodiments, the stopcock, preferably comprised by the hub of the steerable transseptal needle, can be configured as a three-way or four-way stopcock rather than a one-way stopcock to allow for the presence of a side port, operably connected to the lumen of the steerable transseptal needle with minimal required real estate. The side port, in other embodiments, can be affixed to the hub of the steerable transseptal needle at a location other than at the stopcock.

In another embodiment, the hub of the stylet can comprise a quick release or safety catch that prevents the sharp stylet tip from projecting out the distal end of the steerable transseptal needle inner tube lumen more than momentarily. This system includes a release that is activated upon full advancement of the stylet out the distal end, whereby the release activates and allows spring-biased withdrawal of the stylet proximally.

In some embodiments, the quick release, or safety stylet, can comprise an intermediate component that rotates or changes diameter to cause disengagement of the stylet from the button being pushed, such that a spring or other forcing mechanism can withdraw the safety stylet proximally such that it is sheathed and no longer protrudes beyond the distal end of the inner tube. This quick release can be reset by the user, for example, by releasing a button being pushed so that it can return to its initial, loaded, position. In yet other embodiments, the safety stylet hub can comprise magnets that cause the stylet tip to follow a control button or actuator until such time the magnetic force is exceeded by the force of the return spring, tissue resistance, or the like. Once a pre-set force is reached, the magnets pull apart and the stylet can return to its initial, retracted position. The Control handle, once released, likewise can return to its initial, armed position.

In some embodiments, the hub of the steerable transseptal needle piercing stylet can comprise a safety catch or release that prevents actuation of the piercing stylet until such actuation is desired. The safety catch can comprise a pin lock, a C-collar, a safety switch, a removable fastener, a breakaway member, or the like.

In other embodiments, the distal end of the steerable transseptal needle can comprise a cylindrical radiopaque marker band that reduces the diameter of the inner tube and provides for additional Radiopacity and visibility under fluoroscopy. This radiopaque marker band can be used to reduce the annulus around the stylet tip as it protrudes through the distal end of the steerable transseptal needle. However, when the stylet is retracted, the distal orifice of the central lumen of the steerable transseptal introducer is not significantly restricted because the lumen at the center of the RO marker is not blocked by the stylet, whose tip resides proximal to the RO marker sufficiently to allow for fluid flow therethrough.

In other embodiments, the steerable transseptal needle can comprise an electrical plug, operably connected to the inner tube, the central stylet or wire, or the outer tube. The electrical plug can be affixed to the hub of the steerable transseptal needle. The plug can be configured for releasable attachment to the cable of a radio frequency (RF) power supply or "Bovie". The plug can be used to conduct electrical energy to one or more of the tubes or wires of the steerable transseptal needle. The plug can comprise conductive materials such as, but not limited to, stainless steel, cobalt nickel alloy, titanium, brass, copper, nitinol, or the like. The steerable transseptal needle, in these embodiments, can comprise an outer jacket, which has electrical insulating properties, which surrounds the outer tube of the steerable transseptal needle, along some or the entirety of the exposed length of the outer tube, inner tube, or both. The insulating jacket can be fabricated from materials such as, but not limited to, polyester (PET), polyimide, FEP, PFA, PTFE, polyamide, Hytrel, Pebax, PEEK, PVC, polyurethane, polyethylene, polypropylene, or the like. In some embodiments, the insulating jacket can be the same as the pressure shroud surrounding the slots or openings in the tubing at the distal end of the steerable transseptal needle. The insulating jacket can be heat shrunk around the outer tubing, applied as a liquid that dries, slipped over the outer tubing and affixed, or the like.

BRIEF DESCRIPTION OF THE DRAWINGS

FIG. 12A illustrates a top view of a portion of the distal flexible region of an outer tube comprising dovetails or interlocking grooves to reduce torque or side-to-side motion, according to an embodiment of the invention;

FIG. 12B illustrates a side view of a portion of the outer tube distal flexible region of an outer tube comprising dovetails or locking grooves to reduce torque or side-to-side motion, according to an embodiment of the invention;

FIG. 15A illustrates an outer tube cut in its flexible regions with shorter lateral slots and with reduced or complete elimination of some T-slots to improve resistance to bending in that region, according to an embodiment of the invention;

FIG. 15B illustrates a control rod without any control rod retainer leaving only the c-shaped control rod and the distal end, according to an embodiment of the invention;

FIG. 28A illustrates a lateral cross section of a steerable transseptal punch comprising an outer tube having a central lumen and a plurality of radially oriented cuts or grooves disposed in two generally orthogonal directions, the different cuts or grooves being interdigitated between each other along the length of a flexible region, a plurality of control rods and a control rod retainer, according to an embodiment of the invention;

FIG. 28B illustrates a lateral cross section of the steerable transseptal punch comprising an outer tube having a central lumen, two quarter-circular arcuate control rods, and a semi-circular hollow control rod retainer, according to an embodiment of the invention;

FIG. 31A illustrates a side view of a steerable transseptal needle comprising a blunt distal end and a sharp, tissue piercing stylet or obturator, in its retracted state, according to an embodiment of the invention;

FIG. 31B illustrates a side view of the steerable transseptal needle of FIG. 31A with the sharp stylet or obturator advanced distally beyond the distal end of the inner tube to form a sharp, tissue punch, according to an embodiment of the invention;

FIG. 32A illustrates a steerable transseptal needle comprising a radiopaque marker at the distal end of the inner tube as well as a small diameter segment of the stylet wire, according to an embodiment of the invention;

FIG. 32B illustrates the steerable transseptal needle of FIG. 32A with the stylet advanced out the distal end of the inner tube, according to an embodiment of the invention;

FIG. 33A illustrates a steerable transseptal needle comprising a beveled tip, sharp stylet, according to an embodiment of the invention;

FIG. 33B illustrates the steerable transseptal needle of FIG. 33A with the beveled sharp stylet advanced out the distal end of the inner tube;

FIG. 34A illustrates a hub configured for use with a piercing stylet or obturator in its retracted state, according to an embodiment of the invention;

FIG. 34B illustrates the hub of FIG. 34A actuated such that the stylet or obturator is advanced a controlled distance, according to an embodiment of the invention;

DETAILED DESCRIPTION

Figure 1:
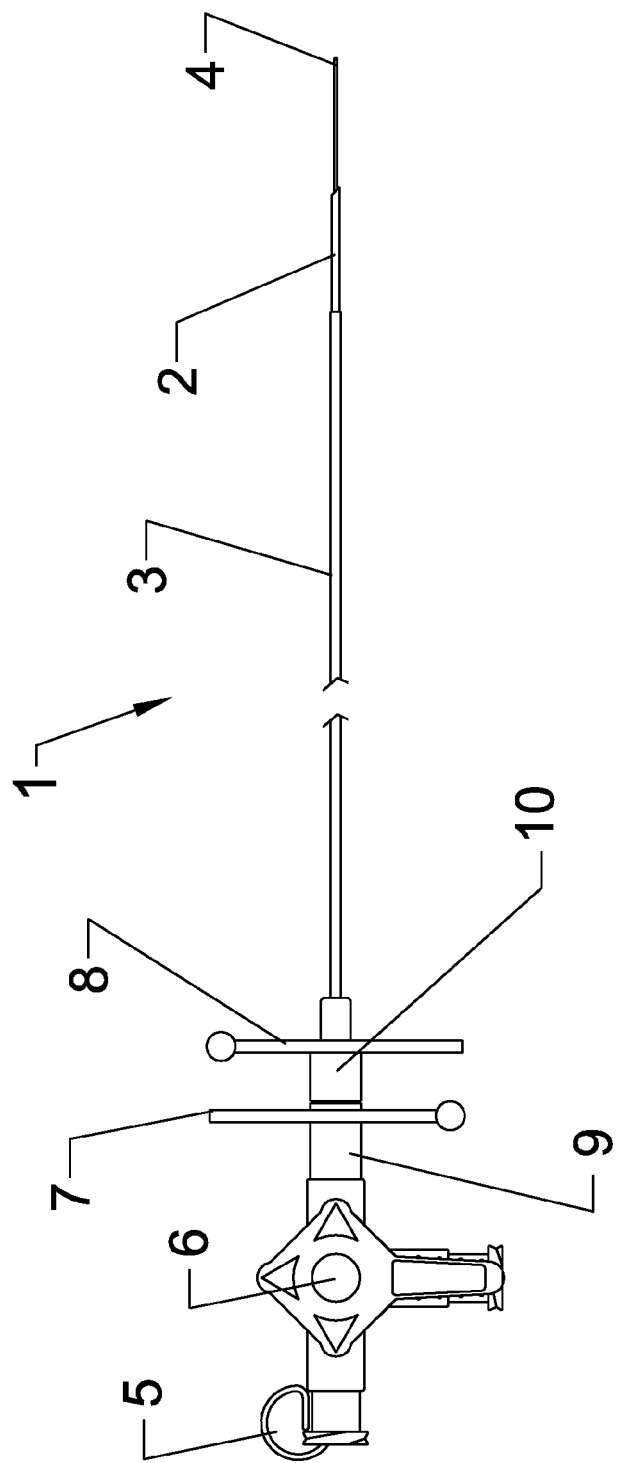
FIG. 1 illustrates a side view of a trans-septal punch assembled so that the intermediate tube is bent in a direction 180 degrees opposite that of the outer tube, resulting in a substantially straight punch configuration, according to an embodiment of the invention.

In accordance with current terminology pertaining to medical devices, the proximal direction will be that direction on the device that is furthest from the patient and closest to the user, while the distal direction is that direction closest to the patient and furthest from the user. These directions are applied along the longitudinal axis of the device, which is generally an axially elongate structure having one or more lumens or channels extending through the proximal end to the distal end and running substantially the entire length of the device.

In an embodiment, the invention is an endoluminally, transvascularly, or endovascularly placed tissue punch, with internal deflectability or the ability to articulate, at its distal end, in a direction away from its longitudinal axis. The punch can also be termed a catheter, needle, or cannula. The punch is generally fabricated from stainless steel and comprises an outer tube, an intermediate tube, a central stylet wire, and a distal articulating region. The deflecting or articulating mechanism is integral to the punch. The punch, needle, or catheter is sufficiently rigid, in an embodiment, that it can be used as an internal guidewire or internal guide catheter. The punch is useful for animals, including mammals and human patients and is routed through body lumens or other body structures to reach its target destination.

In an embodiment, the punch comprises an inner core wire or stylet, an intermediate tube and an outer tube. In an embodiment, the stylet can be removable or non-removable. The punch further comprises a hub at its proximal end which permits grasping of the punch and also includes a stopcock or valve to serve as a lock for the stylet, or inner core wire, as well as a valve for control of fluid passage into and out from the innermost lumen within which the stylet or inner core wire resides. The proximal end further comprises one or more control handles to manipulate the amount of articulation at the distal end of the catheter. The proximal end further is terminated with a female Luer or Luer lock port, which is suitable for attachment of pressure monitoring lines, dye injection lines, vacuum lines, a combination thereof, or the like.

The punch is fabricated so that it is substantially straight from its proximal end to its distal end. Manipulation of a control mechanism at the proximal end of the punch causes a distal region of the punch to bend or curve away from its longitudinal axis. The bending, steering, or articulating region is located near the distal end of the punch and can be a flexible region or structure placed under tension or compression by pull wires or control rods routed from the control handle at the proximal end of the punch to a point distal to the flexible region. The flexible region is thus a region at the distal end of the outer tube that is significantly more flexible and susceptible to deflection than the remaining proximal region of the outer tube. In another embodiment, the bending or articulating mechanism can also be created by pre-bending the outer tube in one direction and bending the intermediate tube in another direction. The two tubes can be rotated relative to each other, about their longitudinal axis, by turning knobs or grips at the proximal end of the punch. When the curvatures of both tubes are aligned, the tubes will generally cooperate and not oppose each other, thus, maximum curvature or deflection is generated. When the tubes are rotated so their natural curvatures are aligned 180 degrees from each other, the curves will oppose each other or cancel out. Thus, the nested tubes will be substantially straight when the curvatures of the two concentric tubes oppose each other. Alignment marks or graduations at the proximal end can be used to assist with proper rotational alignment of the two tubes. The central core wire or stylet is generally straight and flexible and does not contribute to the curvature. In another embodiment, however, the stylet can be imparted with a curvature to assist with steering or articulation. Rotation of the two concentric tubes at relative angles between about 180 degrees and 0 degrees will result in intermediate amounts of deflection so the amount of deflection can be increased or decreased in an analog, continuously variable, digital, or stepwise fashion. The stepwise or digital response can be generated using detents or interlocks that weakly engage at specific pre-determined locations. A locking mechanism can be further utilized to hold the two tubes in rotational alignment once the desired amount of curvature has been achieved.

In another embodiment, steerability can be obtained using actuators on the surface or within the interior of the cannula to force bending of the cannula. These actuators can be typically electrically powered. In an embodiment, an actuator can comprise electrical leads, a power source, a compressible substrate, and shape memory materials such as nitinol. Such actuators may be distributed along the length of the cannula. The actuators may be placed so as to oppose each other. Opposing actuators are activated one at a time and not simultaneously and can generate a steering effect or back and forth motion.

Other embodiments of the inventions comprise methods of use. One method of use involves inserting the central core wire or stylet so that it protrudes out the distal end of the punch. A percutaneous or cutdown procedure is performed to gain access to the vasculature, either a vein or an artery. An introducer and guidewire are placed within the vasculature and the guidewire is routed proximate to the target treatment site. The introducer can be removed at this time. A guiding catheter, preferably with a removable central obturator or dilator, with a tapered distal tip pre-inserted, is routed over the guidewire to the target site. In some embodiments, the guide catheter is routed through from a femoral vein, through the inferior vena cava, and into the right atrium of the heart. In an embodiment, the target site can be the atrial septum of the heart in the region of the Fossa Ovalis. In some embodiments, the guide catheter distal tip is routed past the right atrium and into the superior vena cava. The guidewire can be removed at this time. The punch is adjusted so that it assumes a substantially straight configuration. The punch can be advanced through the central lumen of the already placed catheter, sheath, introducer, or guide catheter. By making the punch as straight as possible, there is no curvature to force the sharpened distal edges of the punch to scrape the inside of the catheter lumen as the punch is advanced distally inside the guide catheter and potentially dislodge or skive away debris or material which could cause embolic effects to the patient. Carefully ensuring that the punch does not protrude beyond the distal end of the catheter or its obturator, the punch is next deflected so that it forms a curve. The distal end of the punch is sufficiently radiopaque that it is observable clearly under fluoroscopy or X-ray imaging. The location of the punch and the amount of deflection and curvature of the distal end are observed and controlled using the aforementioned fluoroscopy or X-ray imaging, or other imaging method such as MRI. The curve is oriented so that it is medially directed toward the atrial septum. Alignment with any curvature of the catheter can be completed at this time. The punch and guide catheter/obturator are withdrawn caudally, as a unit, into the right atrium from the superior vena cava. The punch and guide catheter are positioned using fluoroscopy or other imaging system against the Fossa Ovalis. The Fossa Ovalis is a relatively thin structure and the force of the punch will tent the Fossa Ovalis toward the left atrium. In one embodiment, the central core wire or stylet, initially advanced, can next be withdrawn to expose the sharp distal edge of the punch. When correctly positioned under fluoroscopy, ultrasound, or other imaging system, dye can be injected into the central lumen of the punch at its proximal end and be expelled out of the distal end of the punch and obturator to paint or mark the Fossa Ovalis. A generally "V-shaped" mark can be observed under fluoroscopy, which denotes the location of the Fossa Ovalis. The curvature of the punch can be increased or decreased by articulation to gain optimal alignment with the Fossa Ovalis. This steering function can be very beneficial in device placement.

Maintaining the position of the guiding catheter against the Fossa Ovalis, the punch is advanced distally against and through the atrial septum, in the region of the Fossa Ovalis, so that it penetrates and protrudes into the left atrium. In order to stabilize the atrial septal tissue prior to coring, a distally protruding corkscrew tipped wire or a vacuum head operably connected to the proximal end of the punch, can be used to grasp and retract the septal tissue. Once the initial penetration is completed, the guide catheter is next advanced, with its tapered obturator leading the way, across the atrial septum until it resides within the left atrium. The tapered obturator or dilator along with the punch can be removed at this time to allow for catheter placement through the guiding catheter. In another embodiment, a calibrated spacer can be used between the guide catheter hub and the punch hub to ensure that the punch does not protrude beyond the distal end of the guide catheter tip until the desired time for punching the hole. At this point, the spacer is unlocked and removed from the punch or catheter. In some embodiments, the punch is removed from the guide catheter and the same punch is routed through a second guide catheter to provide access to the left atrium for the second guide catheter. Two guide catheters are often necessary for ablation procedures because one guide catheter is used to route mapping and diagnostic devices into the left atrium while the second guide catheter is used to route therapeutic catheters into the left atrium. Thus, the punch can be used more than once on a given patient but, for prevention of contamination, the same punch should not be used on different patients because cleaning and sterilization after use is nearly impossible given the small distances between the moving inner and outer tubes which can hide contamination from cleaning or sterilization by the user.

In another embodiment, the core wire, obturator or stylet is sharpened and serves as a tissue punch. In this embodiment, the distal end of the hollow tubes of the punch are blunted and made relatively atraumatic. Once the core wire punch has completed tissue penetration, the outer tubes are advanced over the central punch wire through the penetration and into the left atrium. In another embodiment, a pressure monitoring device such as a catheter tip pressure transducer, or a pressure line terminated by a pressure transducer, can be affixed to a quick connect, generally a Luer fitting, at the proximal end of the punch hub. By monitoring pressure, it is possible to determine when the distal end of the punch has passed from, for example, the right atrium into the left atrium, because the pressure versus time curves in these two chambers are measurably, or visually, different. The proximal end of the hub further has provision for attachment to a dye injection line for use in injecting radiographic contrast media through the central lumen of the punch. Typically a manifold can be attached to the Luer fitting on the proximal end of the hub, the manifold allowing for pressure monitoring, for example on a straight through port, and for radiopaque dye injection, for example through a side port. A stopcock, or other valve, can be used to control which port is operably connected to the central lumen of the punch.

In some embodiments, the inner tube, the outer tube, or both can have slots imparted into their walls to impart controlled degrees of flexibility. The slots can be configured as "snake cuts" to form a series of ribs with one or more spines. The spines can be oriented at a given circumferential position on the outer tube, the inner tube, or both. The spines can also have non-constant orientations. In some embodiments, only the outer tube is slotted. The slots can be generated within the distal portion of the outer tube where the curve is generated. This distance can range between 3-cm and 15-cm of the end and preferably between 7-cm and 12-cm of the distal end. The slot widths can range between 0.001 inches and 0.100 inches with a preferable width of 0.003 to 0.025 inches. In exemplary embodiments, the slot widths are about 0.010 inches. In some embodiments, it is desirable to have the outer tube bend in one direction only but not in the opposite direction and not in either lateral direction. In this embodiment, cuts can be made on one side of the outer tubing within, for example, the distal 10-cm of the tube length. Approximately 10 to 30 cuts can be generated with a width of approximately 0.010 to 0.040 inches. The cut depth, across the tube diameter from one side, can range between 0.1 and 0.9 of the tube diameter. In an embodiment, the cut depth can be approximately 0.4 to 0.6 of the tube diameter with a cut width of 0.025 inches. A second cut can be generated on the opposite side of the tube wherein the second cut is approximately 0.005 inches or less. In an embodiment, the outer tube can be bent into an arc first and then have the slots generated such that when the tube is bent back toward the 0.005 inch wide cuts, the tube will have an approximately straight configuration even through each tube segment between the cuts is slightly arced or curved.

FIG. 1 illustrates a side view of a punch, needle, or catheter assembly 100, with an integral articulating or bending mechanism. The punch assembly 100 comprises a stylet or obturator wire 102, an intermediate tube 104, an outer tube 106, an obturator grasping tab 108, a stopcock 110, an intermediate tube pointer 112, an outer tube pointer 114, an intermediate tube hub 116, and an outer tube hub 118. The obturator wire 102 is affixed to the obturator grasping tab 108. The stylet or obturator wire 102 is inserted through the central lumen of the intermediate tube 104 and is slidably disposed therein. The stopcock 110 is affixed to the intermediate tube hub 116 and the through lumen of the stopcock 110 is operably connected to the central lumen of the intermediate tube 104. The intermediate tube pointer 112 is affixed to the intermediate tube hub so that it is visible to the user. The outer tube pointer 114 is affixed to the outer tube hub 118 so that it is visible to the user. The intermediate tube hub 116 and the intermediate tube 104 are able to rotate about the longitudinal axis within the outer tube hub 118 and the outer tube 106. In an embodiment, the intermediate tube 104 is restrained from longitudinal motion relative to the outer tube 106. In another embodiment, the intermediate tube 104 can be advanced distally relative to the outer tube 106. In this latter embodiment, advancement of the inner tube 104 can be used to facilitate punching. The distal end of the intermediate tube 104 can be sharpened and serve as a punch. The distal end of the intermediate tube 104 is sheathed inside the outer tube 106 to protect the tissue from the sharp distal edge of the intermediate tube 104 until the intermediate tube 104 is advanced distally outside the distal end of the outer tube 106. A releasable lock can be used to maintain the axial or longitudinal position of the intermediate tube 104 relative to the outer tube 106 until punching is required. A releasable lock can further be used to maintain the rotational position of the intermediate tube hub 116 and thus the intermediate tube 104 relative to the outer tube hub 118 and the outer tube 106.

All components of the punch assembly 100 can be fabricated from metals such as, but not limited to, stainless steel, Elgiloy™, cobalt nickel alloy, titanium, nitinol, or the like. The nitinol can be shape-memory or it can be superelastic. The metals used in the obturator wire 102, the intermediate tube 104 and the outer tube 106 are advantageously cold rolled, heat treated, or otherwise processed to provide a full spring hardness. The intermediate tube 104, the outer tube 106, or both, are relatively rigid, resilient structures. Polymeric materials, such as, but not limited to, polycarbonate, ABS, PVC, polysulfone, PET, polyamide, polyimide, and the like, can also be used to fabricate the stopcock 110, the intermediate tube hub 116, the outer tube hub 118, the intermediate tube pointer 112, and the outer tube pointer 114. The materials are beneficially radiopaque to maximize visibility under fluoroscopy during the procedure. Additional radiopaque markers fabricated from tantalum, platinum, iridium, barium sulfate, and the like can be added to improve visibility if needed. The intermediate tube 104 is curved or bent near its distal end into a gentle curve, preferably with a radius of between 1 to 5 inches and so that the distal tip is deflected through an angle of approximately 10 to 90 degrees from the longitudinal axis of the intermediate tube 104. The outer tube 106 is curved or bent near its distal end into a gentle curve, preferably with a radius of between 1 to 5 inches and so that the distal tip is deflected through an angle of approximately 10 to 90 degrees from the longitudinal axis of the outer tube 106. The intermediate tube hub 116 is welded, silver soldered, bonded, crimped, or otherwise fastened to the proximal end of the intermediate tube 104 so that the intermediate tube pointer 112 points in the direction of the bend in the intermediate tube 104. The outer tube hub 118 is welded, silver soldered, bonded, crimped, or otherwise fastened to the proximal end of the outer tube 106 so that the outer tube pointer 114 points in the direction of the bend in the outer tube 106. When the intermediate tube pointer 112 is oriented 180 degrees away from the direction of the outer tube pointer 114, the bend in the intermediate tube 104 substantially counteracts or opposes the bend of the outer tube 106 and the coaxial assembly 100 is substantially straight, as shown in FIG. 1. The stopcock 110 can also be a ring seal, Tuohy-Borst valve, membrane valve, hemostasis valve, gate valve, or other valve, generally, but not necessarily manually operated. The stiffness of the intermediate tube 104 and the outer tube 106 are sufficient that the punch can be used as a guide for other catheters through which the punch 100 is passed and will deflect those catheters, even ones that have thick walls and high resistance to bending.

Figure 2:
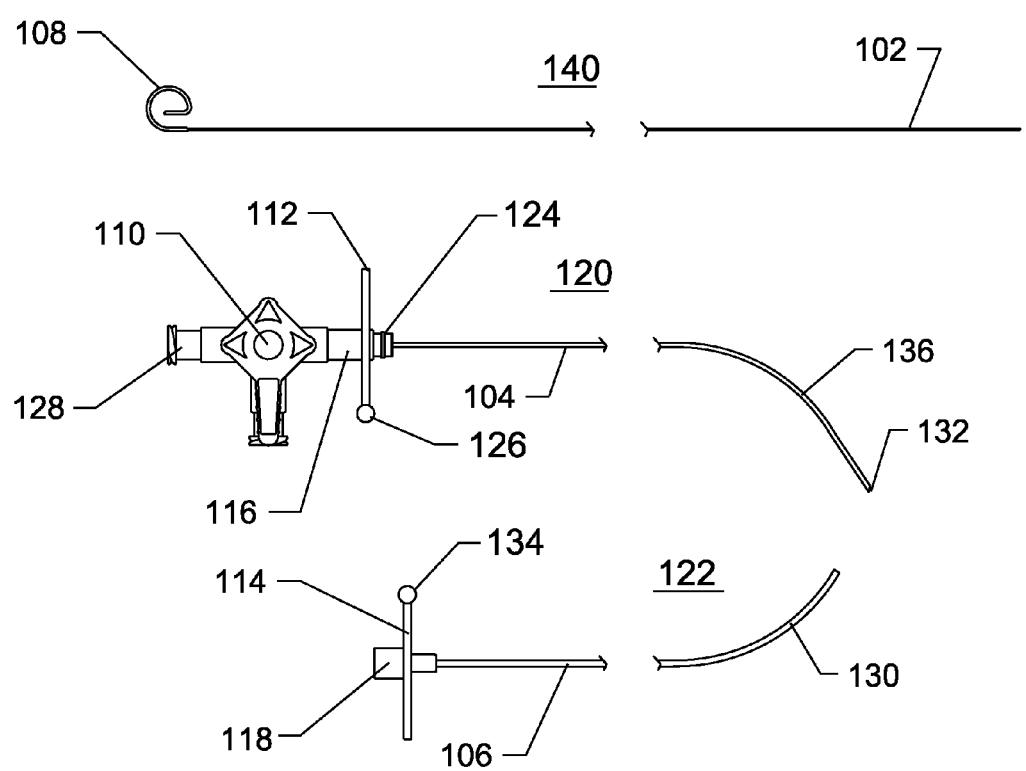
FIG. 2 illustrates a side view of the disassembled transseptal punch showing the central core wire or stylet, the intermediate tube bent in one direction and the outer tube bent in another direction, according to an embodiment of the invention.

FIG. 2 illustrates a side view of a stylet or obturator 140 further comprising the obturator wire 102 and the obturator-grasping tab 108. The obturator wire 102 is blunted at its distal end to render it as atraumatic as possible. In another embodiment, the obturator wire 102 can be tapered in diameter to render it very flexible and therefore atraumatic at its distal end. The obturator wire 102, in another embodiment, can be sharpened and serve as a needle or primary punching mechanism. FIG. 2 also illustrates an intermediate punch assembly 120 further comprising the intermediate tube 104, the stopcock 110, the intermediate tube pointer 112, the intermediate tube hub 116, an intermediate tube seal 124, an intermediate tube pointer ball 126, a through lumen port 128, a beveled distal tip 132, and a pre-set curve 136. FIG. 2 further illustrates an outer tube assembly 122 further comprising the outer tube 106, the outer tube hub 118, the outer tube pointer 114, an outer tube distal curve 130, and an outer tube pointer ball 134.

Referring to FIG. 2, the obturator-grasping tab 108 is affixed, either integral to, silver soldered, welded, crimped, adhered, pinned, or otherwise attached, to the proximal end of the obturator wire 102. The intermediate tube 104 is affixed to the intermediate tube hub 116 by silver soldering, welding, potting, crimping, setscrew, pin, or other fixation method, such that the hub 116 rotates 1 to 1 with the intermediate tube 104. An optional intermediate tube pointer ball 126 is affixed to the intermediate tube pointer 112 and provides additional visual and tactile rotational positioning sense for the intermediate punch or needle assembly 120. A curve or bend 136 is heat set, or cold worked into the intermediate tube 104 at or near its distal end. The distal end of the intermediate tube 104 comprises a bevel 132 which helps serve as a punch or cutting edge for the intermediate tube 104. The angle of the bevel 132 can range between 20 and 70 degrees from the direction perpendicular to the longitudinal axis of the intermediate tube 104. In another embodiment, the bevel is removed and the distal tip of the intermediate tube 104 is a gentle inward taper or fairing moving distally that serves as a dilator should the obturator wire 102 be used as the punching device rather than the blunt distal tip obturator of the intermediate tube 104. The intermediate tube hub 116 further comprises a circumferential groove with an "O" ring 124 affixed thereto. The "O" ring 124 serves to form a fluid (e.g. air, blood, water) tight seal with the inner diameter of the outer sheath hub 118 central lumen and allows for circumferential rotation of the intermediate tube hub 116 within the outer tube hub 118. The "O" ring 124 can be fabricated from rubber, silicone elastomer, thermoplastic elastomer, polyurethane, or the like and may be lubricated with silicone oil or similar materials. The stopcock 110 can be a single way or a three-way stopcock without or with a sideport, respectively.

The outer punch assembly 122 comprises the bend 130, which is heat set or cold worked into the outer tube 106 in the same longitudinal location as the bend 136 of the intermediate tube. The wall thicknesses of the intermediate tubing 104 and the outer tubing 106 are chosen to provide bending forces that cancel out when the curves 136 and 130 are oriented in opposite directions and the intermediate tubing 104 is inserted fully into the outer tubing 106. The wall thickness of the outer tube 106 and the intermediate tube 104 can range between 0.003 inches and 0.20 inches, preferably ranging between 0.004 and 0.010 inches. The outer diameter of the outer tube 106 can range between 0.014 and 0.060 inches and preferably between 0.025 and 0.050 inches. In a most preferred embodiment, the outside diameter of the outer tube 106 is about 0.048 inches. The outer diameter of the obturator wire 102 can range between 0.005 and 0.030 inches and preferably range between 0.010 and 0.020 inches.

Figure 3:
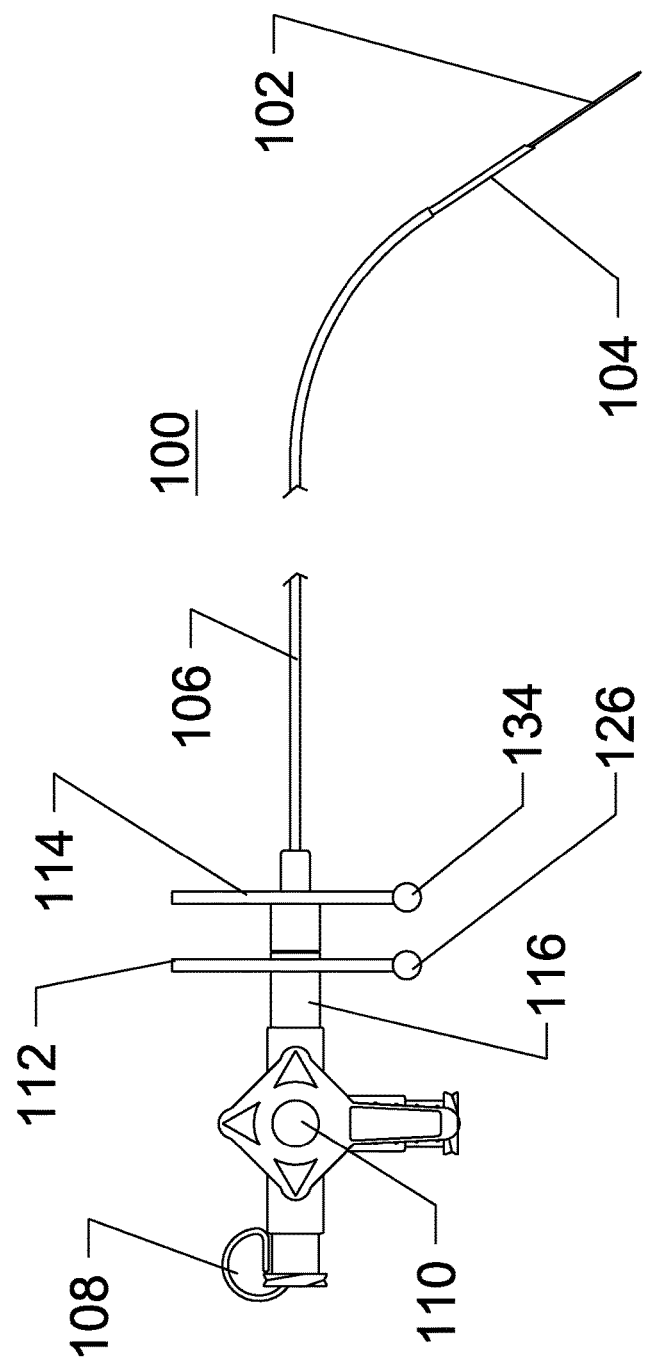
FIG. 3 illustrates a side view of the trans-septal punch assembled so that the intermediate tube bend is aligned in the same direction as the outer tube bend, resulting in a curved distal end on the punch assembly, according to an embodiment of the invention.

FIG. 3 illustrates a side view of the punch assembly 100 fully assembled and aligned so that both the intermediate tube distal curve 136 (Refer to FIG. 2) and the outer tube distal curve 130 are aligned in the same direction resulting in a natural bend out of the axis of the punch 100. The punch assembly 100 comprises the obturator wire 102, the intermediate tube 104, the outer tube 106, the obturator grasping tab 108, the stopcock 110, the intermediate tube pointer 112, the outer tube pointer 114, the intermediate tube hub 116, the intermediate tube pointer ball 126, and the outer tube pointer ball 134. The outer tube pointer 114 and intermediate tube pointer 112 are aligned together and in this configuration, the tubing assembly possesses its maximum curvature, which is oriented in the same directions as the pointers 112 and 114. The pointer balls 126 and 134 are aligned together to provide additional tactile and visual indices of curvature direction. In an embodiment, the curvature of the tube assembly 104 and 106 is unbiased with no net force exerted therebetween and an angle of approximately 45 degrees is subtended by the device in the illustrated configuration. Further curvature can also occur out of the plane of the page so that the curvature takes on a 3-dimensional shape, somewhat similar to a corkscrew. In another embodiment, the curvature of the aligned inner tube 104 and the outer tube 106 subtends an angle of 90-degrees or greater. Again, the intermediate tube 104 and the outer tube 106 have stiffness sufficient that the assembly is capable of guiding any catheter through which the punch 100 is passed. In another embodiment, the intermediate tube 104 and the outer tube 106 have different degrees of curvature so that when they are aligned, a net force still is generated between the two tubes, although a maximum curvature configuration is still generated. This embodiment can be advantageous in permitting articulation in a direction away from the direction of primary curvature. The radius of curvature of the punch 100 can range from substantially infinity, when straight, to as little as 0.5-cm, with a preferred range of infinity to as little as 2-cm radius when fully curved or articulated. One embodiment permits a substantially infinite to a 3-cm radius of curvature. The overall working length of the punch, that length from the proximal end of the outer tube hub to the distal most end of the punch, can range from 10 to 150-cm and preferably between 60 and 100-cm, with a most preferred range of between 70 and 90-cm. A preferred curve has a radius of about 3-cm and is bent into an arc of about 45 to 90 degrees.

Figure 4:
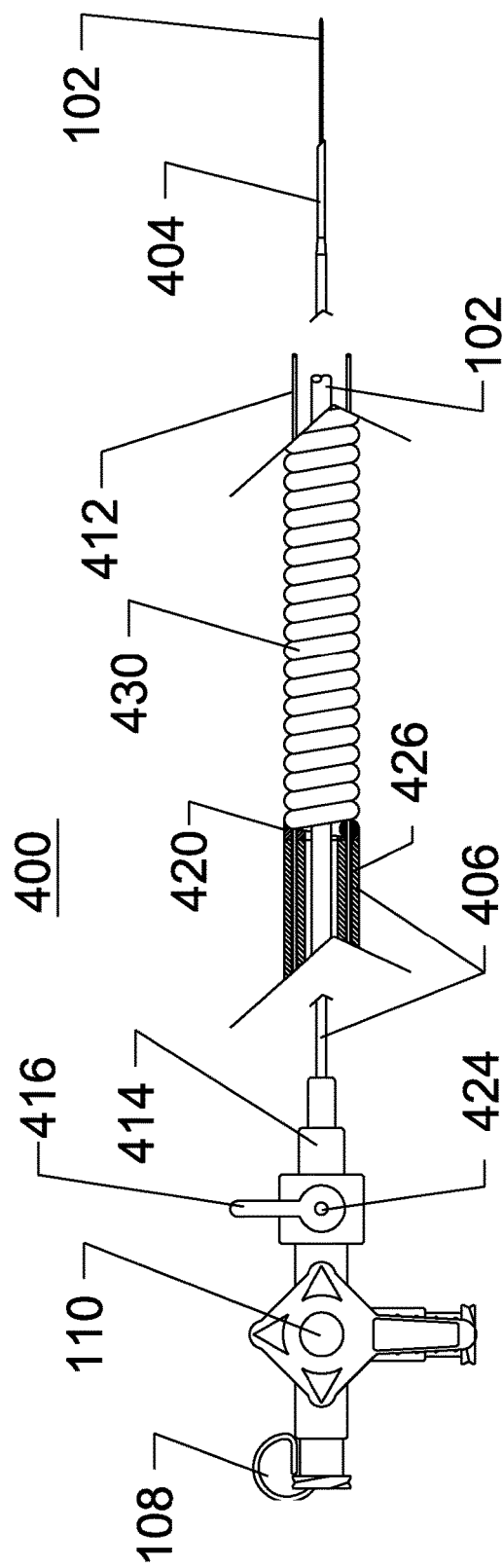
FIG. 4 illustrates a side view of a trans-septal punch comprising a flexible region proximal to the distal end and pull-wires disposed between the distal end and the proximal end of the punch, according to an embodiment of the invention.

FIG. 4 illustrates a side view of another embodiment of a needle or punch assembly 400 comprising an obturator wire 102, an obturator wire grasping tab 108, a stopcock 110, an intermediate tube 404, an outer tube 406, a plurality of deflecting wires 412, an outer tube hub 414, a deflecting lever 416, a weld 420, an axis cylinder 424, a plurality of deflecting wire channels 426, and a flexible region 430. The distal end of the region just proximal to the flexible region 430 is shown in breakaway view. Furthermore, the distal end of the region just proximal to the flexible region 430 as well as the flexible region 430 has been expanded in scale so that certain details are more clearly visible. The flexible region 430 is affixed to the outer tube 406 by a weld 420. The flexible region 430 can also be fixed to the outer tube 406 by a crimp, pin, setscrew, adhesive bond, interference fit, mechanical interlock, thread, or the like. The attachment between the flexible region 430 and the outer tube 406 is made at the proximal end of the flexible region 430 and a second attachment or weld 420 can be made at the distal end of the flexible region 430 so as to attach to a length of distal outer tube 406. The flexible region 430 can comprise a length of coiled wire such as that used in guidewires, it can be a tube that comprises cutouts to provide a backbone configuration to impart flexibility, it can be a length of polymeric tube with elastomeric characteristics, or it can be another type of structure that is known in the art as providing flexibility. These preferred structures also advantageously provide column strength and kink resistance to the flexible region 430. The center of the flexible region 430 is hollow and comprises a lumen, which is operably connected to the central lumen of the outer tube 406 at both the proximal and distal end of the flexible region 430. The stopcock 110 is affixed, at its distal end, to the outer tube hub 414. The outer tube hub 414 further comprises a deflecting lever 416 that is affixed to the axis cylinder 424, which serves as an axle or rotational pin, and can be moved proximally or distally by manual action on the part of the operator or by a motor or other electromechanical actuator (not shown). The deflecting lever 416 is operably connected to the proximal ends of the deflecting wires 412. In an exemplary embodiment, one of the deflecting wires 412 is affixed to the top of the axis cylinder 424 and the other deflecting wire is affixed to the bottom of the axis cylinder 424. When the deflecting lever is pulled proximally, for example, the top wire 412 is placed under tension and the tension on the bottom wire is relieved causing tension to be exerted on the distal end of the punch 400. The deflecting wires 412 are slidably routed through the deflecting wire channels 420 within the outer tube 406. The deflecting wires 412 also run through the deflecting wire channels 420 within the flexible region 430. The deflecting wires 412 can also be routed through the internal lumen of the outer tube 406 and the flexible region 430.

Referring to FIG. 4, the outer tube hub 414 is affixed to the proximal end of the outer tube 406 by a crimp, pin, setscrew, adhesive bond, interference fit, mechanical interlock, thread, or the like. The intermediate tube 404 is affixed to the distal end of the outer tube 406 by a crimp, pin, setscrew, adhesive bond, interference fit, mechanical interlock, thread, or the like. In another embodiment, the intermediate tube 404 is routed throughout the length of the outer tube 406. In this embodiment, the intermediate tube can comprise grooves (not shown) that serve as deflecting wire channels 420 when the intermediate tube 404 is inserted inside the outer tube 406. Such grooves can also be disposed on the interior surface of the outer tube 406, rather than on the exterior surface of the inner tube 404. The obturator wire 102 and the attached grasping loop 108 are slidably disposed within the inner lumen of the outer tube 406, or the intermediate tube 404. The intermediate tube 404 is gently tapered up to the outer tube 406 at the distal end of the outer tube 406 in a transition region so that a dilator effect can be created during distal advancement of the punch 400. The distal end of the intermediate tube 404 can comprise a bevel 132 (FIG. 2) or other sharp point for punching through biological tissue. The distal end of the intermediate tube 404 preferably forms a non-coring needle or punch that does not excise a tissue sample. The non-coring punch feature is achieved by keeping the central lumen closed or very small. The non-coring punch 400 embodiment can comprise filling the lumen of the intermediate tube 404 with the obturator or stylet wire 102 to prevent the sharp edge of the intermediate tube from functioning as a trephine.

Figure 5:
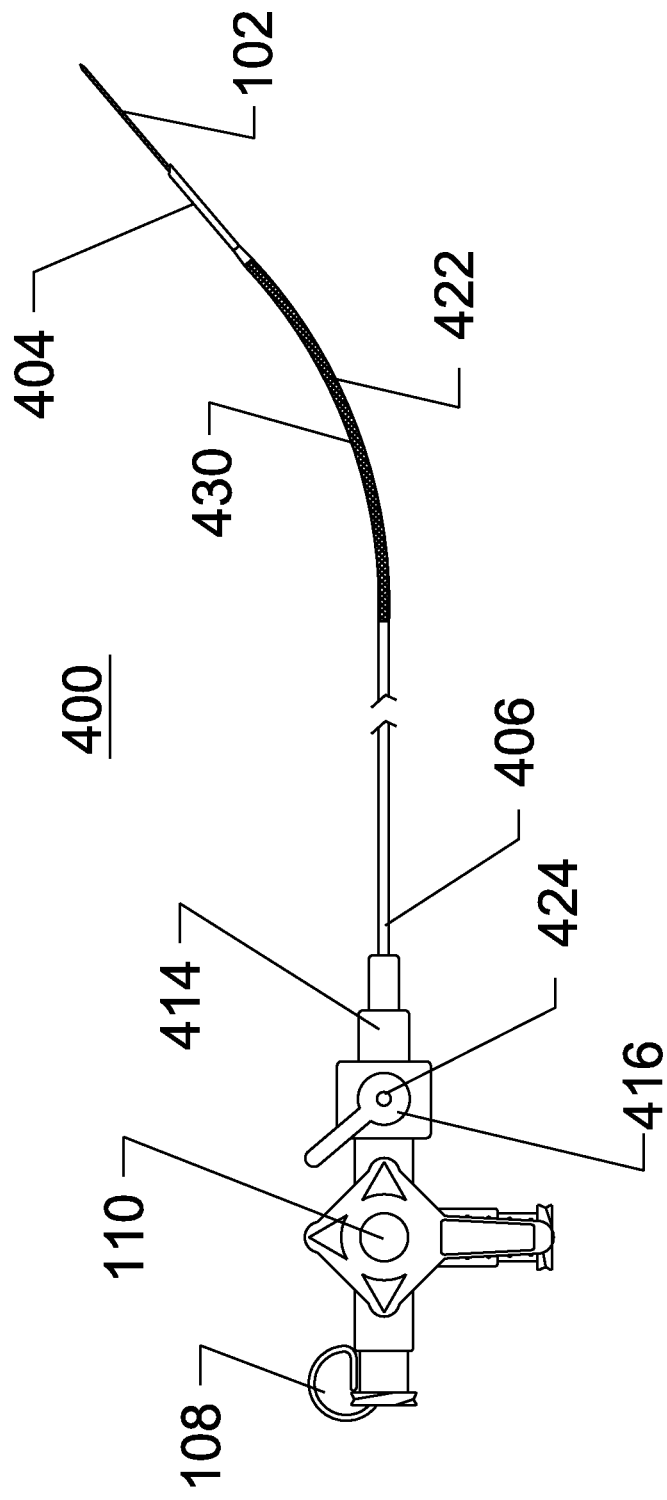
FIG. 5 illustrates a side view of the trans-septal punch of FIG. 4 wherein one of the pull-wires is placed in tension causing the distal flexible region of the punch to deflect into an arc away from the longitudinal axis of the punch, according to an embodiment of the invention.

FIG. 5 illustrates a side view of the punch assembly 400 wherein the deflecting lever 416 has been withdrawn proximally causing increased tension in one of the deflecting wires 412, causing the flexible region 430 to bend 422 out of the longitudinal axis. The punch assembly 400 further comprises the obturator wire 102, the obturator wire grasping tab 108, the stopcock 110, the deflecting lever 416, an axis cylinder 424, the hub 414, the outer tubing 406, the intermediate tubing 404, and the bend 422. The deflecting lever 416 has been moved proximally and the axis cylinder 424 causing the top deflecting wire 412 to be placed in tension while the bottom deflecting wire 412 is relaxed. The deflecting wires 412 are affixed at their distal end to the outer tubing 406 or the intermediate tubing 404 at a point substantially at or beyond the distal end of the flexible region 420. The distal fixation point (not shown) of the deflecting wires 412 is off-center from the axis of the outer tubing 406 or intermediate tubing 404. When uneven tension is created in the opposing deflecting wires 412, the uneven tension on the distal end of the punch 400 causes the flexible region 430 to undergo deflection into a curve or bend 422. Similarly, forward movement of the deflecting lever 416 will place the bottom deflecting wire 412 in tension while the upper deflecting wire 412 will be relaxed, causing the punch 400 to undergo a bend in the opposite direction (downward). The deflecting lever 416 can further comprise a ratchet and lock, a friction lock, a spring-loaded return, or other features to hold position or cause the lever and the flexible region 430 to return to a neutral deflection configuration (substantially straight). The spring nature of the outer tube 406 and the flexible region 430 can advantageously be used to cause a return to neutral once the deflection force is removed from the deflecting lever 416. The stylet or obturator wire 102 can be withdrawn or extended to expose or protect (respectively) the distal end of the intermediate tube 404 which can be sharpened or blunted. The obturator wire 102 can further be used as the primary punch, especially if the distal tip of the obturator wire 102 is sharpened. If the obturator wire 102 is used as the primary punch, the proximal end of the intermediate tube hub is fitted with a Tuohy-Borst or other hemostatic valve to permit the obturator wire 102 to remain in place. In this embodiment, sidearms affixed proximal to the proximal end of the punch, and operably connected to the central lumen, serve to permit pressure monitoring and dye contrast injection without compromising hemostasis or air entry into the punch assembly 400.

Figure 6:
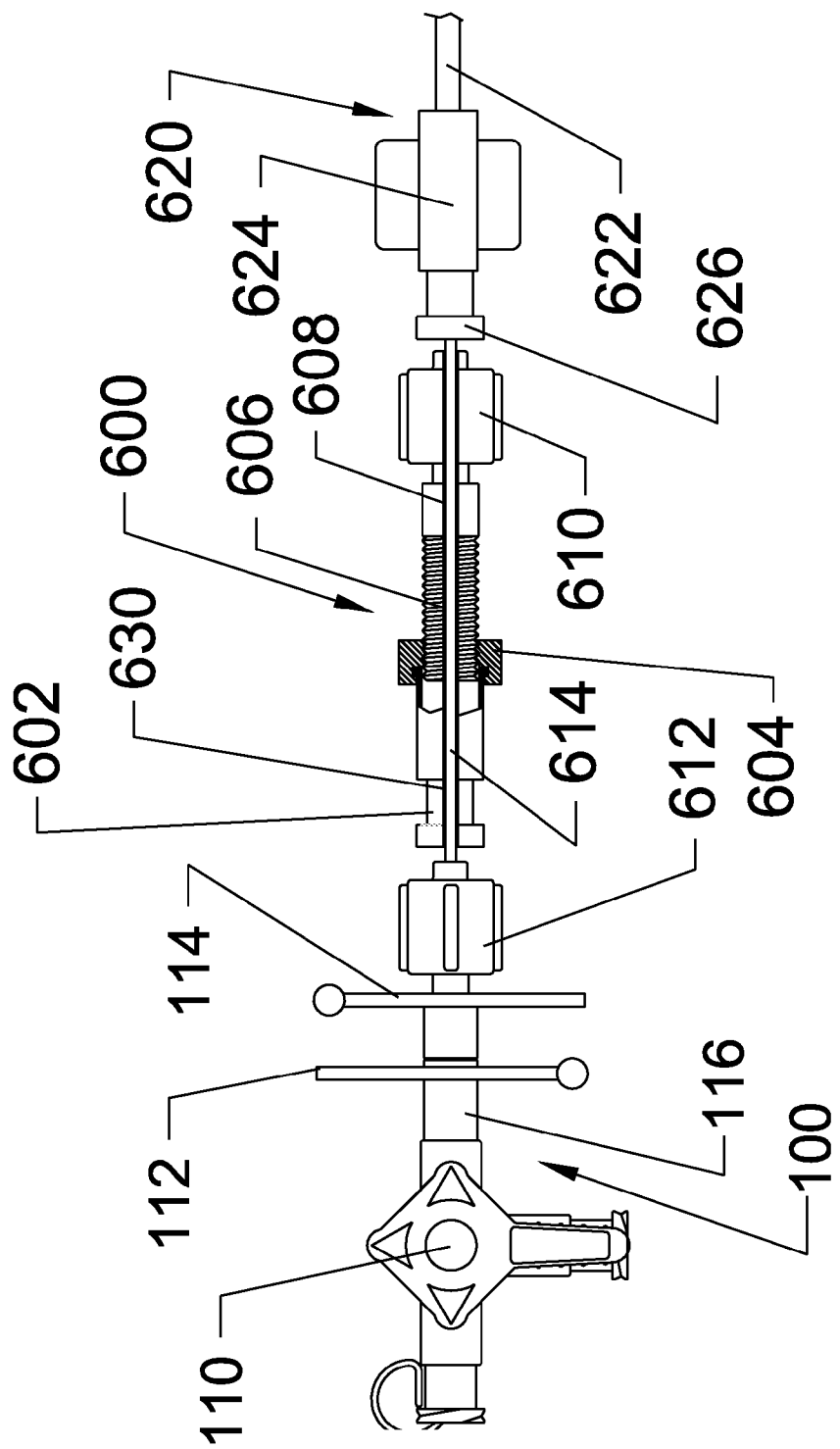
FIG. 6 illustrates an adjustable, spacer, which sets and maintains the distance between the distal end of the punch hub and the proximal end of a guide catheter hub, according to an embodiment of the invention.

FIG. 6 illustrates a side view of an adjustable spacer 600 interconnecting a guide catheter 620 and a punch assembly 100. The spacer 600 further comprises a proximal connector 602, a rotating nut 604, an inner telescoping tube 608, a threaded region 606, a distal locking connector 610, and an outer telescoping tube 614. The guide catheter further comprises a tube 622, a hub 624, and a proximal connector 626. The punch assembly 100 further comprises the stopcock 110, the distal rotating locking connector 612, the intermediate tube pointer 112, the outer tube pointer 114, and the intermediate tube hub 116. The spacer 600 can comprise an optional slot 630. The punch assembly 100 is inserted through the central lumen of the adjustable spacer 600. The distal end of the punch assembly 100 is then inserted through the central lumen of the guide catheter 620. The hub 624 of the guide catheter 620 is affixed to the proximal end of the guide catheter tube 622. The distal end of the hub 624 comprises a female luer lock connection, which is bonded to, or integrally affixed to the hub 624. The hub 624 can further comprise a seal or hemostasis valve such as a Tuohy-Borst fitting. The punch 100 hub 116 is terminated at its distal end by a swivel male luer lock connector 612. The adjustable spacer 600 comprises an outer telescoping tube 614, shown in partial cutaway view that is terminated at its proximal end with a female luer lock 602. The proximal end of the outer telescoping tube 614 has a flange that permits rotational attachment of the rotating nut 604, shown in partial cutaway view, so that the rotating nut is constrained in position, longitudinally, relative to the outer telescoping tube 614 but is free to rotate. The inner telescoping tube 608 is affixed at its distal end with a swivel male luer connector 610, or equivalent. The proximal end of the inner telescoping tube 608 is affixed to, or comprises, the integral threaded region 606. The threaded region 606 mates with the internal threads on the rotating nut 604. As the rotating nut 604 is rotated, either manually or by an electromechanical device, it moves forward or backward on the inner telescoping tube 608 and threaded region 606 thus changing the space between the hub 116 of the punch 100 and the proximal end of the hub 624 of the guide catheter 620. The system is preferably set for spacing that pre-sets the amount of needle or stylet travel. In an embodiment, the rotating nut 604 comprises a quick release that allows disengagement of the inner telescoping tube 608 from the outer telescoping tube 614 so that collapse is permitted facilitating the tissue punching procedure of advancing the punch 100 distally relative to the hub 624. The system further comprises hemostatic valves at some, or all, external connections to prevent air leaks into the punch 100. The telescoping tube 608 can be set to disengage from the outer telescoping tube 614 to allow for longitudinal collapse so that the punch 100 can be advanced distally to provide its tissue punching function. In another embodiment, the spacer 600 comprises the slot 630 that permits the spacer to be removed sideways off the punch 100. The slot 630 is wide enough to allow the outer tube 106 to fit through the slot 630 so the spacer 600 can be pulled off, or removed from, the punch 100 prior to the punching operation. Thus, the slot 630 can be about 0.048 to 0.060 inches wide and extend the full length of the spacer 600. With the slot 630, the spacer 600 comprises a generally "C-shaped" lateral cross-section. The spacer 600 can further comprise a slot closure device (not shown) to prevent inadvertent removal of the punch 100.

In another embodiment, the threaded region 606 and the rotating nut 604 are replaced by a friction lock on telescoping tubes, a ratchet lock, or other suitable distance locking mechanism. In yet another embodiment, a scale or series of markings (not shown) is incorporated into the adjustable spacer 600 to display the exact distance between the proximal end and the distal end of the spacer 600. In another embodiment, the proximal end and the distal end of the spacer 600 do not comprise one or both of the female luer lock 602 or the rotating male luer lock 610. In this embodiment, the spacer 600 provides positional spacing but does not affix the punch 100 to the guide catheter 620 so that the two devices move longitudinally as a unit. In another embodiment, the pull wires 412 of FIG. 4, which are strong in tension but cannot support compression are replaced by one or more control rods, which are flexible but which have column strength. Thus, deflection can be generated by imparting either tension on the control rod or compression and such tension and compression is capable of deflecting the distal tip of the punch 400 without the need of a separate control rod to impart tension in the other direction. The intermediate tube hub 116 is terminated at its proximal end by a female luer, luer lock, threaded adapter, bayonet mount, or other quick release connector. The quick connect or female luer can be releasably affixed to a hemostasis valve, other stopcock, pressure transducer system, "Y" or "T" connector for pressure and radiopaque contrast media infusion, or the like.

In another embodiment, a vacuum line can be connected to a port affixed to the proximal end of the punch. The port can be operably connected to a bell, cone, or other structure at the distal end of the punch by way of a lumen, such as the central lumen of the intermediate tube or an annulus between the intermediate and outer tube, within the punch. By application of a vacuum at the proximal end of the punch, the distal structure can be releasably secured to the atrial septum prior to punching through. In another embodiment, a corkscrew structure projects out the distal end of the punch and is operably connected to a knob or control at the proximal end of the punch by way of a control rod slideably or rotationally free to move within a lumen of the punch. The corkscrew structure can be screwed into tissue to releasably secure the distal end of the punch to the tissue, for example, to enhance stability of the punch prior to, during, or after the punching operation.

Referring to FIG. 1, in another embodiment, the intermediate tube 104, the outer tube 106, or both, are fabricated from shape memory nitinol. In this embodiment, electrical energy can be applied to the pre-bent regions of the inner tube 104, the outer tube 106, or both. Upon application of electrical energy, Ohmic or resistive heating occurs causing temperature of the tubes to increase. The nitinol changes its state from martensitic to austenitic, with the increase in temperature, and can assume a pre-determined configuration or stress state, which is in this case curved. The austenite finish temperature for such a configuration is approximately 40 degrees centigrade or just above body temperature. In yet another embodiment, the austenitic finish temperature can be adjusted to be approximately 28 to 32 degrees centigrade. The punch 100 can be maintained at room temperature where it is substantially martensitic and non-rigid. Upon exposure to body temperatures when it is inserted into the core lumen of the guide catheter, it will assume its austenitic shape since body temperature is around 37 degrees centigrade. This can cause the punch 100 to curve from substantially straight to substantially curved. In this configuration, only a single tube, either the intermediate tube 104 or the outer tube 106 is necessary, but both tubes, while potentially beneficial, are not required.

Figure 7A:
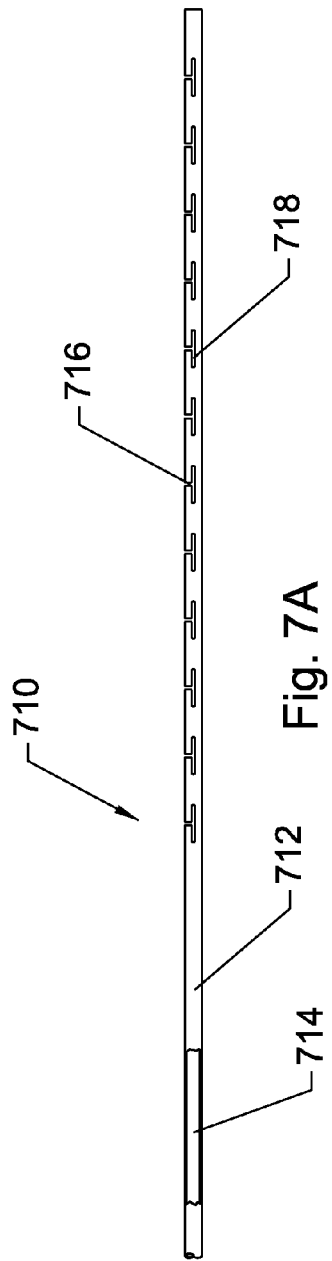
FIG. 7A illustrates a side, partial breakaway, view of an outer tube of an articulating trans-septal punch comprising a plurality of slots near the distal end to generate a region of increased flexibility, according to an embodiment of the invention.

FIG. 7A illustrates a side view, in partial breakaway, of the distal end of an axially elongate outer tube 710, comprising a lumen 714, a proximal, uncut portion 712, a plurality of lateral partial cuts 716, and a plurality of longitudinal "T" cuts 718, according to an embodiment. The outer tube 710 serves as the outer tube of an articulating septal punch such as that illustrated in FIG. 5. The plurality of partial lateral cuts 716 serve to render the region of the outer tube 710 in which the lateral cuts 716 are located more flexible than the proximal region 712. The plurality of longitudinal "T" cuts, serve to further render the region of the outer tube 710, in which the "T" cuts 718 reside, more flexible than in tubes where such "T" cuts 718 were not present. The longitudinal "T" cuts 718 are optional but are beneficial in increasing the flexibility of the outer tube 710 in the selected bend region. The partial lateral slots 716 can be spaced apart by about 0.02 to about 1.0 inches with a preferred range of about 0.1 inches to about 0.8 inches and a further preferred range of about 0.15 inches to about 0.5 inches. In an exemplary embodiment, the partial lateral slots 716 are spaced about 0.17 inches apart. The spacing between the partial lateral slots 716 can vary. In some embodiments, for example, the spacing between the partial lateral slots toward the proximal end of the outer tube 710 can be about 0.3 inches while those partial lateral slots 716 nearer the distal end of the outer tube 710 can be spaced about 0.15 inches apart. The spacing can change in a step function, it can change gradually moving from one end of the outer tube 710 to the other, or it can increase and decrease one or more times to generate certain specific flexibility characteristics. Increased spacing increases the minimum radius of curvature achievable by compression of the partial lateral slots 716 while decreased spacing allows for a smaller minimum radius of curvature.

The number of lateral cuts 716 or, optionally, the number of lateral cuts 716 with T-cuts 718, can number between about 4 and about 50 with a preferred number being between about 6 and about 25 and a more preferred number of about 8 to about 15. In the illustrated embodiment, there are 12 partial lateral cuts 716, each modified with a "T" slot 718. In other embodiments, the partial lateral cuts 716 can be shaped differently. For example, the partial lateral cuts 716 can be at angles other than 90 degrees to the longitudinal axis, curved, V-shaped, Z-shaped, W-shaped or the like. In other embodiments, the 'T' slots 718 can have, for example, further cuts approximately lateral to the longitudinal axis, along any portion of the "T" cut 718.

The outer tube 710 can have an outer diameter of about 0.020 to about 0.1 inches with a preferred outside diameter of about 0.040 to about 0.060 inches and a more preferred diameter of about 0.045 inches to about 0.055 inches. In the illustrated embodiment, the outside diameter is about 0.048 inches while the inner diameter is about 0.036 inches. The inside diameter of the outer tube 710 can range from about 0.0.010 inches to about 0.090 inches.

Figure 7B:
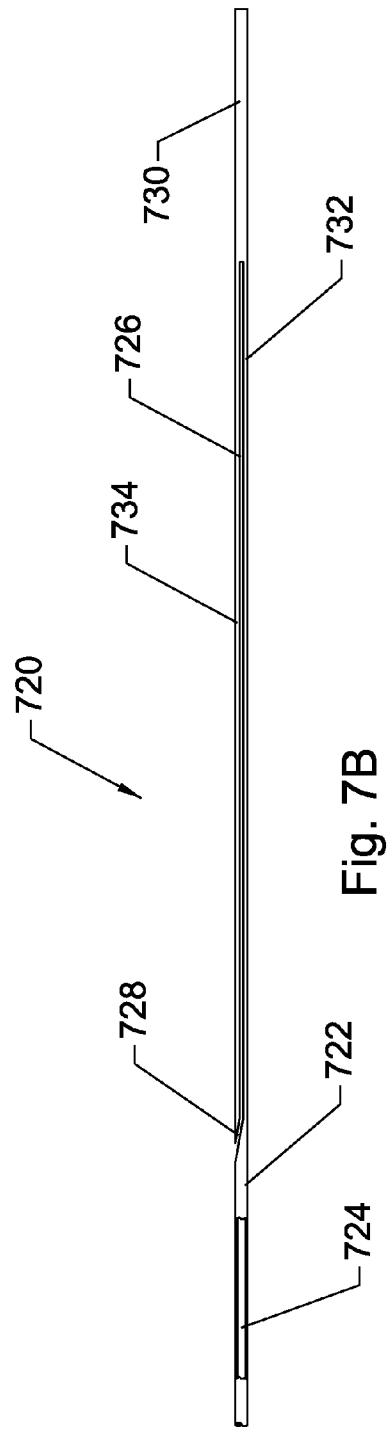
FIG. 7B illustrates a side, partial breakaway, view of an intermediate, or inner, tube of an articulating trans-septal punch comprising a longitudinal slot dividing the tube into two axially oriented parts which are connected at the distal end of the inner tube, according to an embodiment of the invention.

FIG. 7B illustrates an embodiment of a side view, in partial breakaway, of the distal end of an axially elongate intermediate tube 720, comprising a lumen 724, a proximal, uncut portion 722, a longitudinal slot 726 further comprising an angled lead in 728, a free side 734, a pusher or connected side 732, and a distal tip 730. The distal tip 730 interconnects the free side 734 and the pusher side 732. The distal tip 730 further comprises a tapered distal end that can be beveled or otherwise shaped into a sharp edge such as by circumferentially forming a trephine-like (cylindrical) blade or even a pointed end that is closed or partially closed. The free side 734 and the pusher side 732 are generally integrally formed but can also be affixed to each other by welding, adhesives, fasteners, or the like.

The lead in 728 to the longitudinal slot 726 is beneficially angled to prevent guidewires, stylets, or other catheters, which are inserted through the central lumen 724 from being caught or bumping against an edge. The angled lead in 728 serves a guide to assist with traverse of a stylet, obturator, or guidewire past the lead in 728 and into the distal region of the steerable transseptal needle. The lead in 728 can be angled from between about −80 degrees (the angle can be retrograde) from the longitudinal axis (fully lateral) to about +2 degrees and preferably from about +5 degrees to about +20 degrees with a most preferred angle of about +8 degrees and about +15 degrees. In the illustrated embodiment, the angle of the lead in slot 728 is about 10 degrees from the longitudinal axis. A second feature of the lead in 728 is that it be positioned or located proximally to the most proximal "T" slot 718 in the outer tube 710 when the two tubes 710, 720 are affixed to each other (see FIG. 9). The lead in 728 is located at least 1-cm proximal to the proximal most "T" slot 718 and preferably at least 2-cm proximal to the proximal most "T" slot 718 so that bending in the distal region does not distort the lead in 728 and cause kinking, misalignment, or pinching of the internal lumen 724.

The inner or intermediate tube 720 can have an outside diameter that is slightly smaller than the inside diameter of the outer tube 710 so that the intermediate tube 720 can be constrained to move longitudinally or axially within the outer tube 710 in a smooth fashion with relatively little force exerted. In the illustrated embodiment, the outside diameter of the intermediate tube 720 is about 0.033 inches giving about a 0.0015 inch radial clearance between the two tubes 710 and 720. The inside diameter of the intermediate tube 720 can range from about 0.002 to about 0.015 inches less than the outside diameter of the intermediate tube 720. In the illustrated embodiment, the wall thickness of the intermediate tube is about 0.006 inches so the inside diameter of the intermediate tube is about 0.021 inches. The lumen 724 of the intermediate tube 720 can be sized to slidably accept a stylet or obturator 140 such as illustrated in FIGS. 1 and 2. A typical stylet wire 140 can range in diameter from about 0.01 to about 0.23 inches with a preferred diameter range of about 0.012 to about 0.020 inches. In another embodiment, the outer tube 710 has an outside diameter of about 0.050 inches and an inside diameter of about 0.038 inches. In this embodiment, the inner tube 720 has an outside diameter of about 0.036 inches and an inside diameter of about 0.023 inches. The radial wall clearance between the inner tube 710 and the outer tube 720 is about 0.001 inches and the diametric clearance is about 0.002 inches. The annulus between the two tubes must be substantially smooth, free from burrs, and free from contamination because the two tubes 710, 720 beneficially need to translate along their longitudinal axis relative to each other over relatively long axial distances of about 50 to about 150-cm.

The inner tube 720 transmits force along its proximal non-slotted region 722 from the proximal end of the inner tube 720 to the lead in 728 where the force continues to be propagated along the connected side 732 to the distal end 730. The outer tube 710 transmits force along its proximal non-slotted region 712. Longitudinal forces applied to the distal, flexible region with the slots 716 cause deformation of the outer tube in an asymmetrical fashion with the side of the outer tube 710 comprising the partial lateral slots 716 forming an outer curve if the slots 716 are expanded and an inside curve if the slots 716 are compressed. Forces to cause bending are preferably exerted such that the partial lateral slots 716 are compressed up to the point where the gap closes, but no further, however forces can also be exerted to expand the slots 716, however limits on curvature are not in place because the lateral slots 716 can open in an unrestrained fashion except for the material properties of the outer tube 710.

The disconnected side 734 of the inner tube 720, separated from the connected side 732 by the longitudinal slot 726 and the lead in 728, serves to maintain an undistorted tube geometry and provide resistance to deformation while helping to maintain the inner lumen 724 in a round configuration and provide a shoehorn or funnel effect to guide an obturator, guidewire, or stylet 140 therethrough as they are advanced distally. The disconnected side 734, being separated from the force transmitting member 722 cannot provide any substantial longitudinal load bearing structure, although at its distal end, where it is integral or affixed to the distal end 730, some tension load carrying capability exists.

The intermediate tube 720 can be considered a split tube and does not carry a load in compression or tension along substantially the entire length of the disconnected side 734.

The partial lateral slot 716 in the inner tube 720 and the T-Slot 718 in the outer tube 710, as well as the longitudinal slot 726 in the inner or intermediate tube 720, and the lead in slot 728 can be fabricated by methods such as, but not limited to, electron discharge machining (EDM), wire EDM, photoetching, etching, laser cutting, conventional milling, or the like. In other embodiments, different slot configurations can also be employed, such as curved slots, complex slots, zig-zag slots, or the like. In some embodiments, the partial lateral slot 716 can be configured with a tongue and groove or dovetail design to prevent or minimize lateral movement or torqueing of the outer tube 710 in the flexible region. In some embodiments, the tongue and groove or dovetail (not shown) can be generally centered between two "T" slots, for example. The parts can be ganged and fixture such that, using wire EDM, for example, a plurality of tubes can be cut to reduce manufacturing costs. As many as 20 to 30 tubes, or more, can be fixed, secured, and etched by the aforementioned methods.

Figure 8:
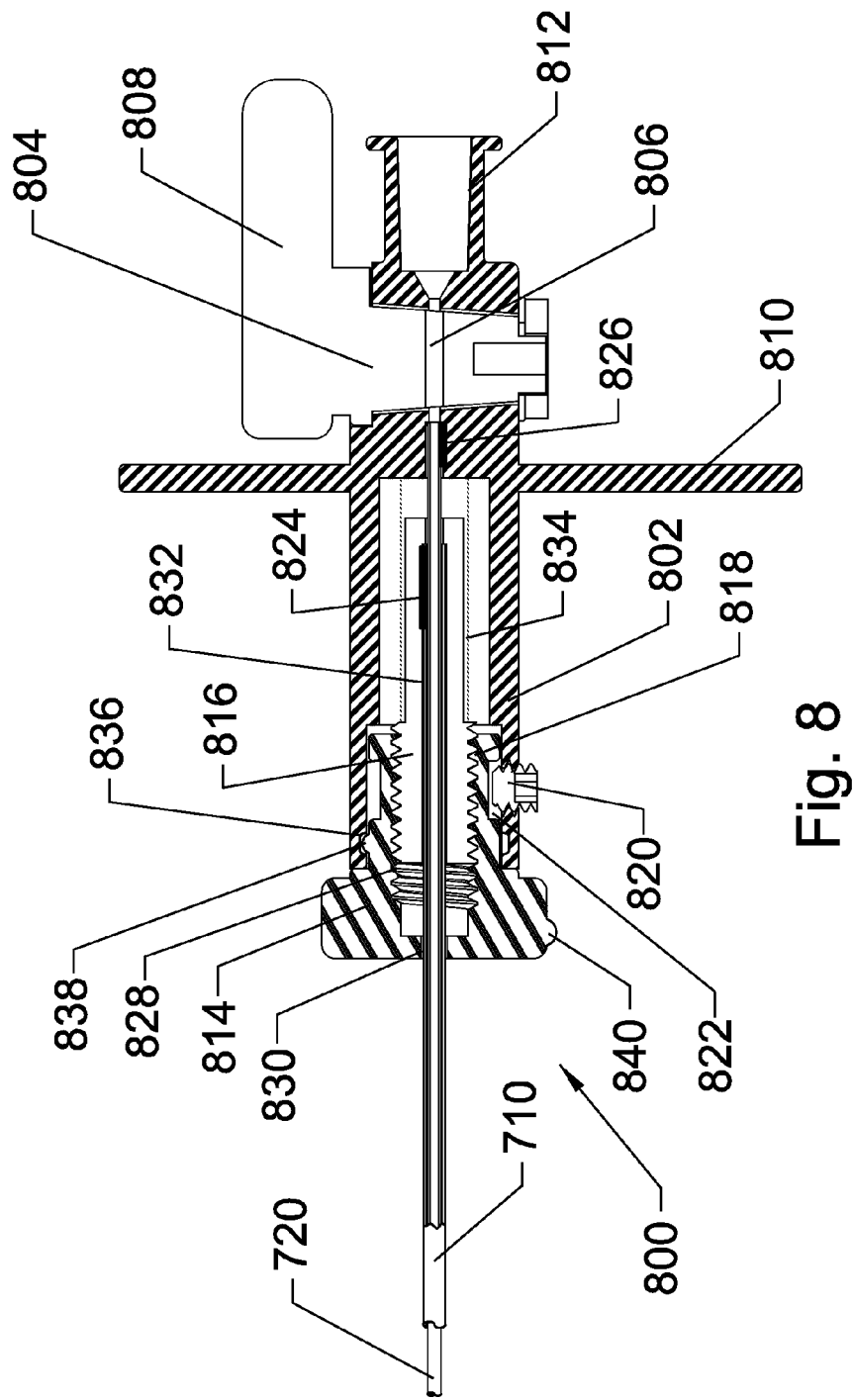
FIG. 8 illustrates a cross-sectional view of the proximal end of the articulating trans-septal punch comprising a stopcock and a bend adjusting mechanism, according to an embodiment of the invention.

FIG. 8 illustrates a side, cross-sectional view of an embodiment of a hub end 800 of an articulating septal punch. The hub end 800 comprises the outer tube 710, the intermediate tube 720, a hub body 802, a stopcock petcock 804 further comprising a petcock handle 808 and a petcock through bore 806, a Luer lock fitting 812, an arrow pointer 810, a keyed lumen 834, a setscrew or pin 820, a jackscrew body 816 further comprising a plurality of threads 828 and a central lumen 832, a control knob 814 further comprising a plurality of threads 818, a central lumen 830, the protrusion 838, and a circumferential recess 822, an outer tube weld 824, an orientation mark 840, and an intermediate tube weld 826. The hub body 802 can further comprise a plurality of recesses or complementary structures 836. The petcock 804 is affixed to the petcock handle 808 by welding, integral fabrication, fasteners, adhesives, or the like. The petcock 804 is retained within a lateral through bore in the hub body 802, which is in the illustrated embodiment, tapered, using a locking "C" washer, fastener, screw, pin, or the like (not shown). The petcock 804 can be rotated about its longitudinal axis to align the through bore 806 with the axis and central lumen of the hub body 802 or it can be rotated sideways to shut off and seal the lumen against the flow of fluids. The Luer lock 812 can be affixed to, or integrally fabricated with, the hub body 802. The knob 814 is retained within the hub body 802 by the setscrew of pin 820 which prevents axial movement but permits rotational movement as constrained by the setscrew, projection, or pin 820 riding within the circumferential recess 822 which is integrally formed or affixed to the knob 814. The jackscrew body 816 is capable of axial movement within the hub body 802 but is restrained from rotation about the long axis by flats or features on the exterior of the jackscrew body 816 which are constrained by flats or features in the keyed lumen 834. The knob 814 comprises threads 828 on its internal lumen which engage with external threads 818 on the jackscrew body 816. Rotation of the knob 814 thus causes the jackscrew body 816 to move axially proximally or distally with mechanical advantage. Rotation of the knob 814 can be forced using manual action or using a motor or other mechanism (not shown). The outer tube 710 is affixed to the jackscrew body 816 by the outer tube weld 824. The intermediate tube 720 (which can also be called the inner tube) is affixed to the hub body 802 by the intermediate tube weld 826. The central lumen 724 of the inner tube 720 is operably connected to a central lumen of the hub body 802, the petcock through bore 806, and the lumen of the Luer fitting 812.

The knob 814 can comprise markings 840 to permit the user to visualize its rotary or circumferential position with respect to the hub body 802. These markings 840 can comprise structures such as, but not limited to, printed alphanumeric characters (not shown), a plurality of geometric shapes such as dots, squares, or the like, or the markings can comprise raised or depressed (embossed) characters of similar configuration as described for the printed markings. In an embodiment, the knob 814 can comprise a number on each of the facets so the facets can be numbered from one to 6, in the illustrated embodiment. The knob markings 840 can further comprise raised structures, as illustrated, which can further be enhanced with contrasting colors for easy visualization.

The knob 814 can further comprise one or more complementary structures affixed or integral thereto, such as a plurality of protrusions 838 that fit into detents 836 affixed or integral to the proximal end of the hub body 802. Such protrusions extending into detents in the hub body 802 can provide a ratcheting or clicking sound as well as providing resistance to inadvertent movement of the knob 814 once it is rotated to the correct location. The knob 814, in some embodiments, can be biased toward the hub body 802 to ensure that complementary structures such as the protrusions and detents come into correct contact. In other embodiments, the knob 814 can comprise a ratchet system to further control its rotary movement with respect to the hub body 802. In other embodiments, the knob 814 can comprise one or more detents (not shown) while the hub body 802 can comprise one or more complementary protrusions (not shown). It is beneficial that the knob 814 be moved only when required by the user and not by accident or not when it is required to maintain its rotary position and, by consequence, the curvature at the distal end of the tubing. The number of ratchet locations, or low energy positions or setpoints, can range from about 2 per 360 degree rotation to about 20 with a preferred number of ratchet locations ranging from about 4 to about 12.

The hub body 802 can be fabricated from biocompatible metals such as, but not limited to, stainless steel, titanium, nickel coated brass, cobalt nickel alloy, and the like, although it could also be fabricated from polymeric materials in a less expensive format. The knob 814 can be fabricated from the same metals as the hub body 802 but it can beneficially be fabricated from biocompatible polymers such as, but not limited to, polyamide, polyimide, polyvinyl chloride (PVC), acrylonitrile butadiene styrene (ABS), acetal polymers, polycarbonate, polysulfone, PEEK, Hytrel®, Pebax®, and the like. The petcock 804 and petcock handle 808 can be fabricated from the same materials as the knob 814, or it can be different materials. The jackscrew body 816 can be fabricated from the same materials as the hub body 802, or from different materials, but must be able to be strongly affixed to the outer tube 710.

Figure 9:
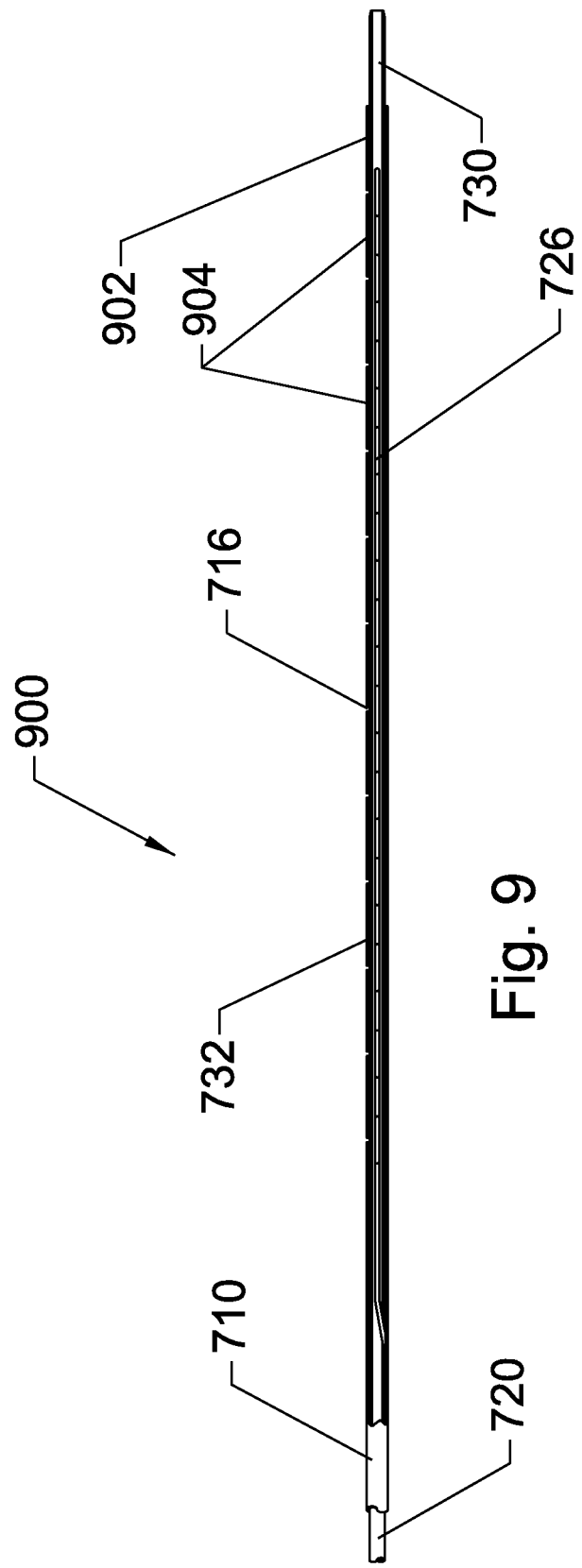
FIG. 9 illustrates a partial breakaway view of the distal end of the articulating trans-septal punch comprising the outer tube and the intermediate tube arranged concentrically and oriented circumferentially, according to an embodiment of the invention.

FIG. 9 illustrates a side view, in partial breakaway, of an embodiment of a distal end 900 of an articulating transseptal punch with any stylets removed. The distal end 900 comprises the outer tubing 710 further comprising the lateral partial slits 716 and the intermediate (or inner) tubing 720 further comprising the longitudinal slit 726 and the distal tip 730. A weld 902 affixes the distal end of the outer tubing 710 to the connected side 732 of the inner tube 720. The distal end 900 can further comprise one or more separate radiopaque markers 904. The outer tube 710 and the inner tube 720 are rotated about the longitudinal axis such that the connected side 732 of the intermediate tube 720 is generally aligned with, and affixed or welded 902 to, the outer tubing 710 on the side comprising the partial lateral slits 716. The flexible region of the inner tube is disposed within the flexible region of the outer tube, within the longitudinal extent of the flexible region of the outer tube. The width of the partial lateral slits 716, the T-slots 718, and the longitudinal slot 726 can range from about 0.001 to about 0.050 inches with a preferred range of about 0.005 to about 0.020 inches. In the illustrated embodiment, the slits 716, 718, and 726 are about 0.010 inches. The width of the partial lateral slits 716 on the outer tube 710 can be used, in compression to provide at least some limit to how much the outer tube 710 can bend in compression along the side comprising the partial lateral slits 716. Note that the intermediate tube 720 extends beyond the distal end of the outer tube 710. In the illustrated embodiment, the intermediate tube 720 extends about 10 mm to about 20 mm beyond the distal end of the outer tube 710. This construction provides for reduced device complexity, increased reliability of operation, and reduced manufacturing costs relative to other steerable devices. The system also provides for high stiffness when the distal end 900 is straight, as illustrated, curved as in FIG. 11, or curved, bent, deflected, steered, or otherwise deformed in any configuration between straight and maximally curved. The articulating trans-septal punch is necessarily stiff, has high column strength, and has significant resistance to bending from external sources because it needs to force an incision through tissue at the end of a very long, 2 to 4 foot length, of very small diameter punch tubing. Thus, the all-metal tubing punch can translate forces from its proximal end to its distal end that a polymeric catheter could not come close to equaling. Catheters carrying such a punch would be less effective for the specific purpose of transseptal puncturing than would the articulating trans-septal needle.

The distal end 900 of the articulating trans-septal punch is generally fabricated from metals with sufficient radiopacity or radio-denseness that they are clearly visible under fluoroscopic or X-ray imaging. However, if this is not the case, additional radiopaque markers 904 can be affixed to the outer tube 710, the inner tube 720, or both. These radiopaque markers can comprise materials such as, but not limited to, tantalum, gold, platinum, platinum iridium, barium or bismuth compounds, or the like.

Close tolerances between the internal diameter of the outer tube 710 and the outside diameter of the inner tube 720, ranging from a radial gap of between about 0.0005 inches to about 0.008 inches, depending on diameter cause the two tubes 710 and 720 to work together to remain substantially round in cross-section and not be ovalized, bent, kinked, or otherwise deformed. This is especially important in the flexible distal region comprising the partial lateral cuts 716 on the outer tube 710 and the longitudinal slot 726 in the inner or intermediate tube 720. The two tubes 710 and 720 can be fabricated from the same materials or the materials can be different for each tube 710, 720. Materials suitable for tube fabrication include, but are not limited to, stainless steel, nitinol, cobalt nickel alloy, titanium, and the like. Certain very stiff polymers may also be suitable for fabricating the tubes 710, 720 including, but not limited to, polyester, polyimide, polyamide, polyether ether ketone (PEEK), and the like. The relationship between the inner tube 720, the outer tube 710, and the slots 716, 718, 726, 728 serve to allow flexibility and shaping in high modulus materials such as those listed above, which are not normally suitable for flexibility. The internal and external surface finishes on these tubes 710, 720 are preferably polished or very smooth to reduce sliding friction between the two tubes 710, 720 because of their very small cross-sections and their relatively long lengths. Lubricants such as, but not limited to, silicone oil, hydrophilic hydrogels, hydrophilic polyurethane materials, PFA, FEP, or polytetrafluoroethylene (PTFE) coatings can be applied to the inner diameter of the outer tube 710, the outer diameter of the inner tube 720, or both, to decrease sliding friction to facilitate longitudinal relative travel between the two tubes which is necessary for articulating the flexible, slotted region near the distal end 900 of the articulating transseptal sheath. The exterior surface of the outer tube 710 can be covered with a polymeric layer, either substantially elastomeric or not, which can cover the slots 716, 718, etc. and present a smoother exterior surface to the environment. The exterior surface can be affixed or configured to slip or slide over the exterior of the outer tube 710.

The weld 902 affixes the outer tube 710 to the intermediate or inner tube 720 such that they cannot move relative to each other along the longitudinal axis at that point. However, since the two tubes 710, 720 are affixed to each other on the side of the outer tube 710 containing the partial lateral slots or gaps 716, compression or expansion of those gaps 716 can be accomplished by moving the weld 902 by relative movement of the inner tube 720 and the outer tube 710. The weld transmits the force being carried by the connected side 732 of the inner or intermediate tube 720 to the slotted side of the outer tube 710. Note that the terms intermediate tube 720 and inner tube 720 are used interchangeably, by definition. The inner tube 720 becomes an intermediate tube 720 if another tube or catheter is passed through its internal lumen 724.

In other embodiments, since the inner or intermediate tube 720 is split 726 lengthwise in the flexible region, a portion, or the entirety, of the distal end of the intermediate tube 720 can be affixed, adhered, welded, fastened, or otherwise attached to the outer tube 710 and functionality can be retained. The distal end 730 of the intermediate tube 720 can, in some embodiments be retained so as to create a cylindrical distal region 730 in the intermediate tube 720 and this entire cylindrical distal region 730, or a portion thereof that does not project distally of the distal end of the outer tube 710 can be welded to the outer tube 710 around a portion, or the entirety of the circumference of the outer tube 710. If only a portion of the inner tube 720 is welded to the outer tube 710, then the weld is beneficially located, approximately centered, on the side of the outer tube 710 comprising the partial lateral slots 716. The cylindrical distal region 730 is a beneficial construction, rather than completely cutting the inner tube 720 away on one side, since the distal region 730 projects distally of the distal end of the outer tube 710 to form the tip of the punch further comprising a sharpened tip 1102, 1302 configured to punch through myocardial tissue (refer to FIGS. 11 and 13).

In some embodiments, one of the welds, all of the welds, or a portion of the welds can be completed using techniques such as, but not limited to, TIG welding, laser welding, silver soldering, fasteners, adhesives, plasma welding, resistance welding, interlocking members, or a combination thereof. Laser welding is beneficial because it is highly focused and can be located with high accuracy. These welds include the weld 902 at the distal end that connects the inner tube 720 and the outer tube 710 as well as the welds at the proximal end connecting the inner tube 720 to the hub and the outer tube 710 to the traveler of the jack-screw 816.

Figure 10:
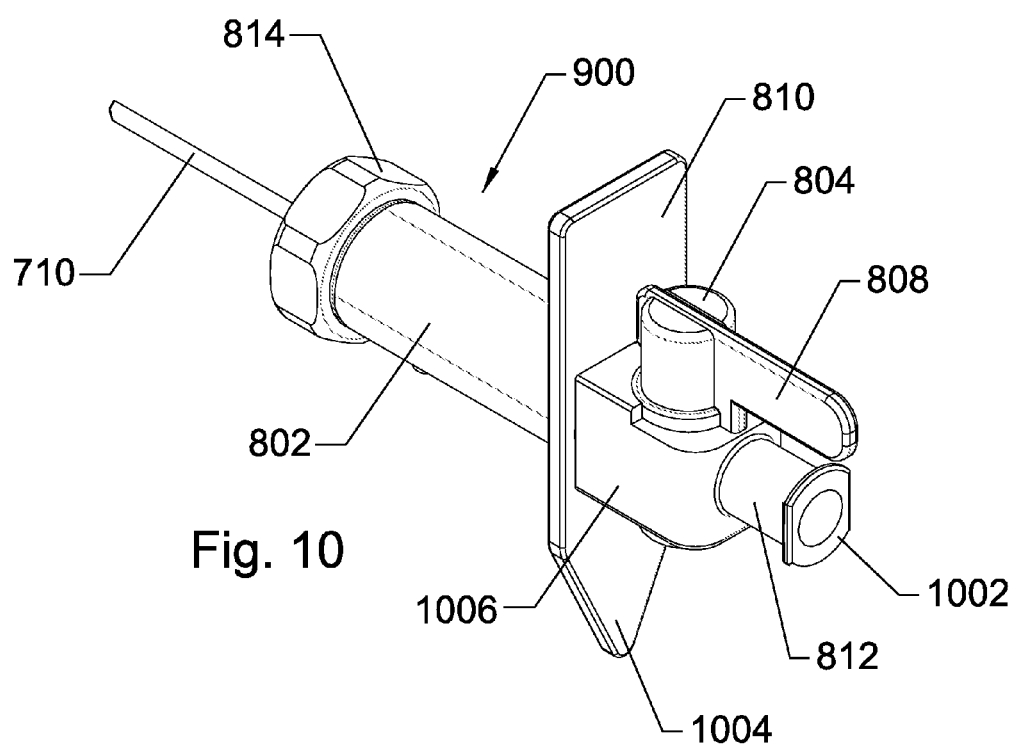
FIG. 10 illustrates an oblique view of the proximal end of the articulating trans-septal punch, according to an embodiment of the invention.

FIG. 10 illustrates an oblique external view of an embodiment of the proximal end 800 of the steerable trans-septal needle comprising the outer tube 710, the knob 814, the hub body 802, the arrow pointer 810 further comprising the pointed end 1004, a stopcock body 1006, the petcock 804, the petcock handle 808, and the Luer fitting 812 further comprising a locking flange 1002. The pointed end 1004 can be integrally formed with the arrow pointer 810, or it can be affixed thereto. The arrow pointer 810 can be integrally formed with the hub body 802, or it can be affixed thereto using fasteners, welds, adhesives, brazing, soldering, or the like. The stopcock body 1006 can be integrally formed with the hub body 802 or it can be affixed thereto using fasteners, welding, soldering, brazing, adhesives, threads, bayonet mounts, or the like. Referring to FIGS. 8 and 10, the lumen of the Luer fitting 812 is operably connected to the through bore of the petcock 804 if the petcock 804 is aligned therewith (as illustrated), or the petcock 804 can be rotated about an axis to misalign the through bore of the petcock 804 with the Luer fitting 812 and prevent fluid flow or passage of solid material therethrough. The knob 814 can be round, shaped as a lever, it can comprise knurls, facets (as illustrated), or it can comprise a plurality of projections which facilitate grabbing and rotation by the user. Circumferential motion of the knob 814 about is longitudinal axis is preferably and beneficially smooth but with sufficient friction to maintain its position in any desired configuration.

Figure 11:
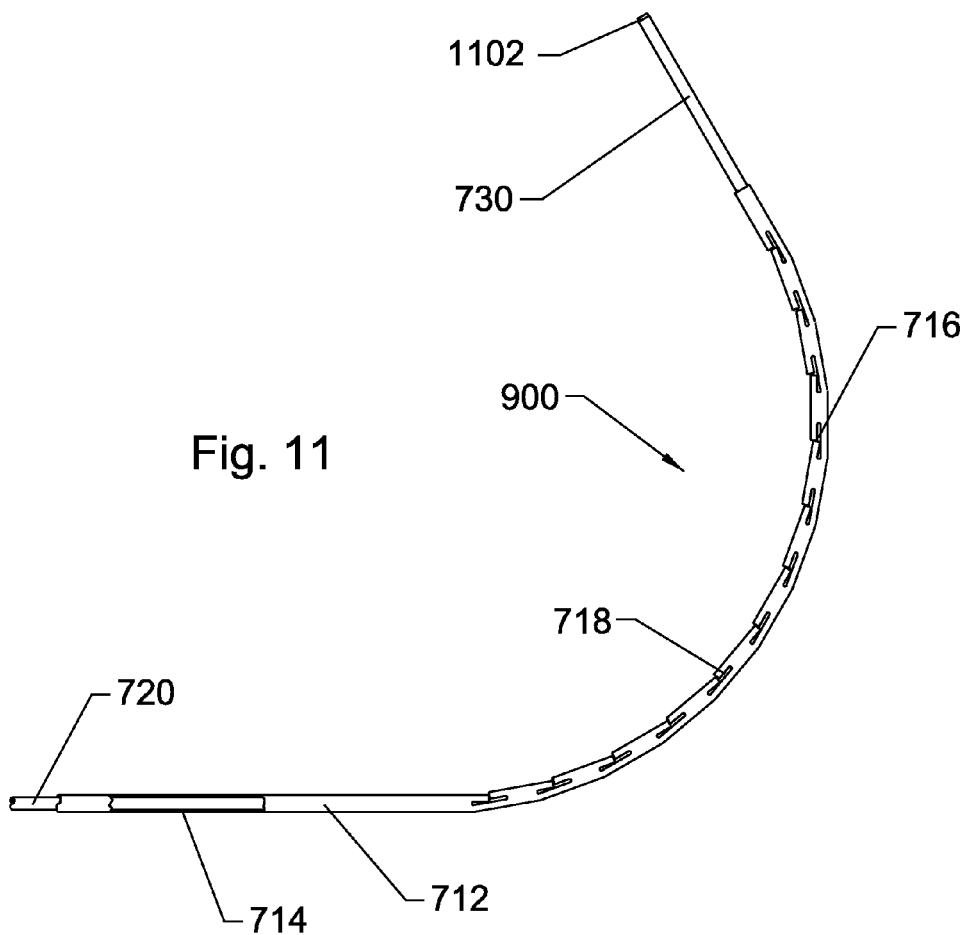
FIG. 11 illustrates a side view of the distal end of the articulating trans-septal punch incorporating a control rod and a control rod retainer, separated from each other, and the outer T-slotted tube with the inner tube being pulled proximally relative to the outer tube causing the outer tube to deform into a curve having very stiff, or rigid, mechanical properties, according to an embodiment of the invention.

FIG. 11 illustrates an embodiment of the distal end 900 of the articulating trans-septal needle in a curved configuration. The distal end 900 comprises the outer tube 710, the intermediate tube 720, the outer tube lumen 714, the distal end of the proximal region of outer tube 712, the distal end 730 of the intermediate tube 720 further comprising the sharpened distal tip 1102, the plurality of outer tube longitudinal cuts or slots 718, and the plurality of outer tube partial lateral cuts 716. The outer tube partial lateral cuts 716 represent spaces that close up when the side of the tube in which the lateral cuts 716 are located is placed in compression. Such compression is generated by pushing the outer tube 710 distally relative to the intermediate tube 720. When the partial lateral cuts 716 gaps close, further compression is much more difficult because the outer tube 710 stiffens substantially when no further gap exists for compression. The composite structure, with the intermediate tube 720 nested concentrically inside the outer tube 710 is relatively stiff and resistant to kinking no matter what amount of curvature is being generated. Such stiffness is essential when using the articulating trans-septal needle to bend or steer another catheter such as a Mullins introducer, or other guide catheter.

Preferred radius of curvatures for the distal end can range from about 1 inch to about 6 inches, with a preferred range of about 2 inches to about 4 inches and a more preferred range of about 2.5 to about 3.5 inches for the purpose of puncturing the atrial septum. Even smaller radius of curvatures would be appropriate in, for example, the cerebrovasculature, the arteries of the heart, and the like. The radius of curvature need not be constant. In some embodiments, the proximal end of the flexible region can have the partial lateral cuts spaced more widely than those at the distal end of the flexible region, causing the distal end to bend into a tighter radius than, the proximal end of the flexible region. In other embodiments, the distal region can be less flexible than the proximal end of the flexible region.

The partial lateral cuts 716, and the "T"-slots in the outer tube 710 are beneficially treated using etching, electropolishing, passivation, sanding, deburring, machining, or other process to round the external edges of the partial lateral cuts 716. Thus, the edges are blunted or rounded so they are not sharp such as to cause the articulating trans-septal needle to dig, skive, or shave material from the inside of a polymer guide catheter since that is a primary benefit of using the articulating trans-septal needle rather than a pre-curved, non-articulating, trans-septal needle or other punch that, when advanced distally through a polymeric sheath, can scrape or skive material from the inner diameter of the sheath or introducer.

The distal end 1102 can be sharp in some embodiments but it can also be somewhat or completely blunted. In the case of partially or completely blunted distal construction, the distal end can be operably connected to a source of electrical or radiofrequency (RF) energy and puncture holes can be created using the electrical or RF energy. The energy is carried by the intermediate tube 720, which is preferably electrically insulated from the outer tube 710, from the hub 900 into which electrical or RF energy can be applied to the distal tip 1102.

FIG. 12A illustrates a top view of another embodiment of an outer tube 1200 in the region of the distal, flexible section, wherein the outer tube 1200 comprises a plurality of partial lateral cuts or slots 1206 further comprising a dovetail 1202. The dovetail 1202 creates a groove 1202 and further comprises a peg or projection 1204 that rides or is circumferentially constrained within the groove 1202 as long as the outer tube 1200 is neutrally forced, or forced in compression on the side of the partial lateral cuts or slots 1206. The projection 1204 riding within the dovetail groove 1202 provides for torque resistance and torsional rigidity in the area of the dovetail 1202.

FIG. 12B illustrates a side view of the outer tube 1200 in the region of the distal, flexible section, wherein the outer tube 1200 comprises the partial lateral slots 1206, the dovetail 1202 further comprising the projection 1204, and the "T" slots 718. The T-slots 718 are optional or they can be configured differently.

The punch can be used to create holes in various structures in the body. It is primarily configured to serve as an articulating or variable deflection Brockenbrough needle. However, the steerable punch can be used for applications such as transluminal vessel anastomosis, biopsy retrieval, or creation of holes in hollow organs or lumen walls. The punch can be used in the cardiovascular system, the pulmonary system, the gastrointestinal system, or any other system comprising tubular lumens, where minimally invasive access is beneficial. The punch can be configured to be coring or non-coring in operation, depending on the shape of the distal end and whether an obturator or the circular hollow end of the punch is used to perform the punching operation. In the coring configuration, a plug of tissue is removed using, for example, a cylindrical cutting blade at the distal end, while in the non-coring configuration, substantially no tissue is removed from the patient. The punch facilitates completion of transseptal procedures, simplifies routing of the catheters, minimizes the chance of embolic debris being dislodged into the patient, and improves the ability of the cardiologist to orient the punch for completion of the procedure. The punch of the present invention is integral and steerable. It is configured to be used with other catheters that may or may not be steerable, but the punch disclosed herein does not require external steerable catheters or catheters with steerability to be steerable as it is steerable or articulating on its own. The punch is capable of bending and unbending a practically unlimited number of times. The punch is especially useful with catheters that are not steerable since the punch comprises its own steering system.

The punch can be removed from the lumen of a catheter after it completes perforation of the hollow organ or vessel wall, through which it is placed, so as to maximize the size of said lumen and allow for advancement of devices such as diagnostic mapping catheters, ablation catheters, catheters to place atrial appendage closure devices, mitral valve repair devices, mitral valve replacement devices, annuloplasty rings, and the like. Without removal of the punch, the lumen is compromised and the capacity of the sheath to introduce catheters is reduced, given a certain outside diameter. Minimizing the outside diameter of the sheath is important in preventing a damaged fossa Ovalis. This device is intended for use with catheters and is not intended for use as integral to a catheter. This device steers itself and can steer a catheter but is not a replacement for a steerable catheter. For instance, an introduction sheath or guide catheter can be steered and bendable but if the trans-septal punch is not steerable and is pre-bent, advancement of the pre-bent trans-septal punch through the sheath or guide catheter and its obturator, steerable or not, will cause the sharp distal end of the trans-septal punch to shave or skive off debris or material from the inside diameter of the obturator of the sheath or guide catheter or the catheters themselves. This shaving or skiving can occur even when the trans-septal punch is protected by a central obturator, stylet, inner tube, or guidewire. Use of a steerable obturator does not help the situation because a pre-bent, trans-septal punch, advanced through a straight, steerable obturator will still shave off or skive material from the inside diameter of the obturator.

The steering mechanism disclosed herein in FIGS. 7A & 7B through-FIG. 11 can be used to steer other types of catheters, guide catheters, introducers, sheaths, guidewires, or even obturators that are placed within the aforementioned devices, with high degree of control over long lengths up to 250 cm or more while requiring less wall thickness and thus allowing for larger internal lumens than steerable devices of the prior art with the same outside diameter. Typical sheaths can have internal lumens with capacities of, for example, 6-Fr to 12-Fr and still maintain very thin walls of around 1-Fr. While smaller catheters or guide catheters with lumens in the range of about 2-Fr to 5-Fr can have even smaller wall thicknesses, depending on the materials used to construct the walls of the sheath. Some sheath constructions can comprise composite materials such as an inner tube fabricated from metal and an outer tube fabricated from metal with a polymeric exterior coating. The inner tube can further be coated with an interior liner of, for example PTFE, or other fluoropolymers (PFA, FEP), Parylene, Pebax®, Hytrel®, polyimide, polyamide, PET, or the like, to create certain reduced frictional properties, electrically insulating properties, or both. These coatings or liners can range in thickness from about 0.0001 to about 0.005 inches, with a preferred thickness range of about 0.0005 to 0.002 inches. Electrical insulating properties are important if electrically conductive catheters are inserted through one or more lumens of a guide catheter or introducer whose mechanical properties are derived from high strength materials such as, in certain embodiments, conductive metal. Electrical insulating properties are also important should the device itself be used for electrical purposes such as, but not limited to, RF Ablation, RF hole puncturing, RF coagulation, and the like.

The steering mechanism disclosed herein, comprising two or more nested axially elongate cylindrical tubes moving relative to each other only along the longitudinal axis, can provide a high degree of precision, repeatability, force, column strength, torsional control, and the like, in a configuration with extremely thin walls and large inside diameter (ID) to outside diameter (OD) ratio. One of the tubes comprises partial lateral cuts or complex lateral gaps and the other tube comprising a split running substantially the length of the flexible region. The disconnected side of the slit tube can be removed so that only a partially formed, connected side remains. However, in preferred embodiments, the disconnected side, which is actually retained at the distal end, is not removed but serves to fill space within the lumen of the outer tube 710 to prevent kinking, improve column strength, prevent lumen collapse and provide for guiding of central stylets or catheters. Prior art devices require greater wall thickness, which reduces the size of the internal lumen relative to a given outside diameter, or they do not have the same degree of precise movement at the distal tip under control from the proximal end of the device.

Figure 13:
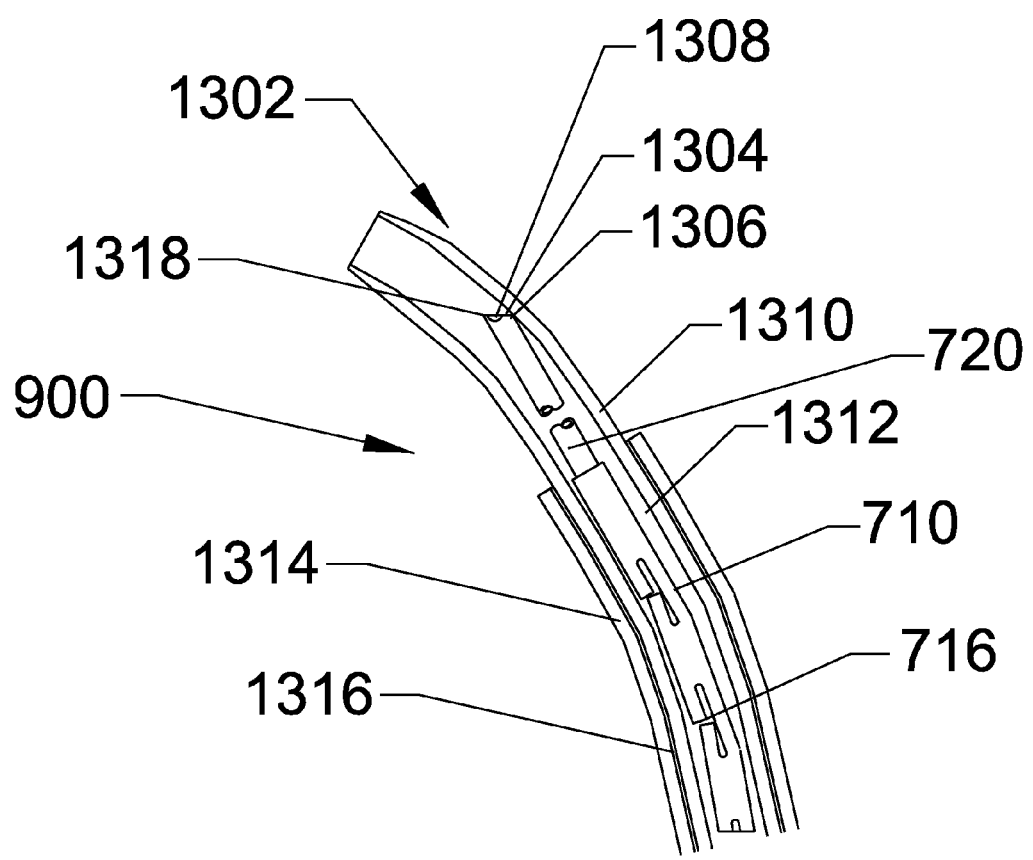
FIG. 13 illustrates the distal end of an articulating septal punch advanced nearly to the distal end of an obturator or dilator, which is coaxially, removably assembled into the central lumen of a guide catheter sheath, according to an embodiment of the invention.

FIG. 13 illustrates a side view of the distal end 900 of an articulating transseptal punch advanced through a central lumen 1312 of a dilator or obturator 1310 of a guide catheter 1314. The articulating transseptal punch distal end 900 comprises the outer tube 710, comprising the plurality of partial lateral cuts 716, and the inner tube 720, comprising a sharpened distal tip 1302. The sharpened distal tip 1302 comprises a bevel 1304, one or more facets 1308, a point 1318, and a rounded or blunted outside edge 1306. The obturator 1300 further comprises the central lumen 1312. The guide catheter 1314 further comprises a central lumen 1316. The guide catheter 1314 and its obturator 1310 are generally curved near the distal end. When the distal end 900 is advanced distally through the lumen 1312 of the obturator 1310, scraping of the inner wall of the obturator 1310 is prevented by inclusion of a rounded edge 1306 of the distal end 1302 toward the outside of the curvature. The distal sharp end 1302 comprises a bevel 1304 to create a sharpened tissue punch with a point 1318. The facets 1308 are optional but can be provided in numbers ranging from one to about 10. The bevel 1304 can be generated at a single angle, or with a complex curvature. In some embodiments, the bevel 1304 can be generated at an angle of about 20 to about 80 degrees from lateral to the axis of the tube with a preferred range of about 30 to about 60 degrees from lateral, and a most preferred range of about 40 to about 50 degrees. The point 1318 can be a point in three dimensions or in two dimensions, such as the point 1318 illustrated herein.

Figure 14:
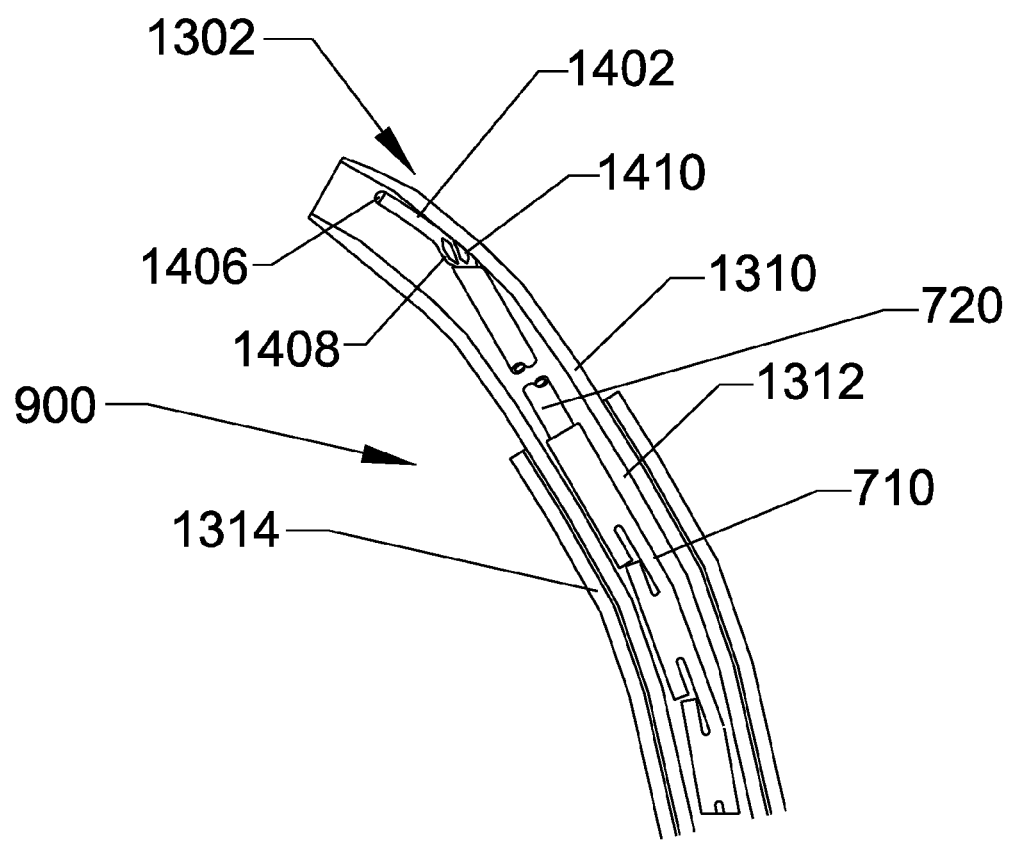
FIG. 14 illustrates the distal end of an articulating transseptal punch further comprising a removable obturator having a collapsible distal shield, according to an embodiment of the invention.

FIG. 14 illustrates the distal end 900 of an articulating transseptal punch further comprising a stylet 1400. The stylet comprises the core wire 1402, the proximal lock 1404 (not shown), a collapsing shield 1408, and the rounded distal tip 1406. The stylet 1400 is slidably and removably inserted through the central lumen of the inner tube 720 to assist with blunting the sharpened distal end. Stylets sufficiently small to fit through these central lumens of the inner tube 720 are generally quite small, having a diameter of about 0.012 to 0.015 inches and are necessarily very weak. They are subject to bending and kinking and cannot hide a sufficient amount of the distal pointed end 1302 to prevent damage to the inside of a polymeric guide catheter 1314 or its obturator 1310. Because the inner tube 720 has a very thick wall relative to its overall diameter, a wire inserted through the central lumen of the inner tube 720 cannot protect or shield the distal end 1302 adequately. Thus, a regular stylet 1400 is only partially useful in preventing skiving material from the inside of the guide catheter 1314 or obturator 1310 unless it includes the collapsing shield 1408. A radially collapsing feature 1408 of the obturator 1400 can be beneficial in protecting the distal end with more completeness than a non-collapsing version. The collapsing feature 1408 is collapsed radially, laterally, or diametrically by withdrawing the obturator 1400 inside the inner tube 720 and it expands on its own using self expansion under spring bias, shape memory recovery, or the like. The obturator 1400 can be fabricated from materials such as, but not limited to, stainless steel, nitinol, cobalt nickel alloy, titanium, and the like using methods such as cold rolling or tempering to achieve substantial spring conditions. In the illustrated embodiment, the collapsing shield feature 1408 is created by means of a split tube of spring stainless steel, comprising a plurality of slots or openings 1410 which are biased outward to create a bulge when unrestrained. The slotted tube shield 1408 is integral or affixed to the core wire 1402. The amount of outward bulge of the shield 1408 is not large but is sufficient to substantially equal or exceed the wall thickness of the inner tube 720.

In some embodiments, the outer tube 710 can be modified to adjust stiffness. It can be preferential to increase the resistance to bending moving distally to proximally on the outer tube 710. This increase in bending resistance contravenes the tendency of the outer tube to bend more severely at the proximal end of the flexible region than in the distal region. It is possible to configure the bending so that the bend radius is approximately constant or such that a greater curvature (smaller radius of bending) is generated moving toward the distal end of the flexible region. The partial lateral slots 716 can be cut with reduced depth more proximally to increase the resistance to bending imparted by the outer tube 710. The partial lateral slots 716 can be cut more narrowly in the more proximal regions to reduce the distance the slot 716 can close. The T-slots 718 can be reduced in length or removed in the more proximal regions of the flexible region of the outer tube 710. Elastomeric bumpers or fillers can be added to some of the partial lateral slots 716 to reduce the amount the partial lateral slots 716 can compress. Once the partial lateral slots 716, associated with the T-slots 718 have closed under bending of the outer tube 710, further bending is resisted and is substantially arrested. By tailoring the width and spacing of the partial lateral slots 716, a specific final curvature can be tailored for a given catheter.

FIG. 15A illustrates an the outer tube 710 comprising the lumen 714, the proximal tube wall 712, the plurality of partial lateral slots 716, the plurality of T-slots 718, a short partial lateral slot 1502, a slightly longer partial lateral slot 1504, and a standard length lateral slot 716 but with a shortened T-slot 1506. The most proximal partial lateral slot 1502 penetrates less than the standard partial lateral slots 716. The second (moving distally) partial lateral slot 1504 is slightly longer than slot 1502 and therefore is more flexible in that region and requires less force to generate bending. The third partial lateral slot comprises the shortened T-slot 1506 which reduces the ability of the tubing to bend given a constant bending force.

FIG. 15B illustrates the inner tube 720 comprising the lumen 724, the proximal region 722, the connected side 732, the distal end 730, the sharpened tip 1302, and a beveled lead-in 1510 at the proximal end of the distal end 730. The proximal end of the disconnected region can be moved distally to increase the stiffness of the inner tube 720 in a specific region, generally the most proximal part of this distal, flexible region.

Since, during use of the steerable transseptal needle, the needle is advanced distally through an already placed introducer, sheath, or guide catheter, it is beneficial that the straight steerable transseptal needle be capable of advancing through any curvatures in the already placed introducer, sheath, or guide catheter. Thus. In certain embodiments, the bevel is oriented such that the pointed point of the sharpened tip 1302 is oriented toward the direction of bending. In this way, the steerable transseptal needle, when in its straight configuration, can be pushed against into the curved region of the introducer, sheath, or guide catheter and not have the sharp point dig into the wall of the introducer, sheath, or guide catheter. The side of the sharpened tip 1302 away from the sharp point can further be rounded somewhat to make it even more atraumatic and smooth so it can skate or sled along the curvature of the introducer, sheath, or guide catheter without digging out any material from the wall of the introducer, sheath, or guide catheter.

In certain preferred embodiments, it is beneficial that the inner tube 720 can sustain compression to generate bending of the outer tube 710 at the distal end back to straight after being curved and even to bend beyond straight in the other (or opposite) direction. In order to sustain compression, it is beneficial that the disconnected side 734 be separated from the connected side 732 at or near substantially the center or midpoint of the tubing. Depending on the width of the slot 726 separating the disconnected side 734 from the connected side 732, the location of the slot can be offset from the midpoint but this is dependent on the wall thickness of the inner tube 720 and the angle of the slotting. In a preferred embodiment, interference exists between the disconnected side 734 and the connected side 732 such that the disconnected side and force transmitting member cannot move substantially inward, a situation that would have negative effects of obstructing the lumen, restricting fluid flow therethrough, trapping stylets or other catheters that need to move longitudinally therein, or buckling sufficiently to prevent application of longitudinal compression forces on the connected side 732.

Figure 16A:
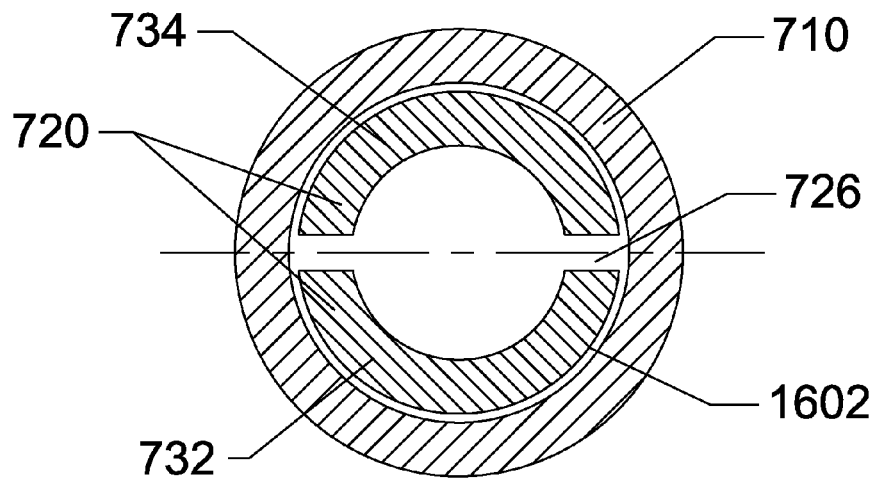
FIG. 16A illustrates a cross-sectional view of a control rod configuration in a steerable transseptal punch within the flexible region, wherein the separation between the control rod and a control rod retainer is substantially at the midpoint or center of the outer tubing, according to an embodiment of the invention.

FIG. 16A illustrates a lateral cross-sectional view an inner tube 720 nested inside an outer tube 710 and separated from the outer tube 720 by a radial gap 1602 in the flexible region of an articulating septal punch wherein the inner tube 720 is separated by a split or gap 726 into two approximately or substantially equal parts, a connected side 732 and a disconnected side 734, approximately (or substantially) at the midline or centerline of the cross-section.

Figure 16B:
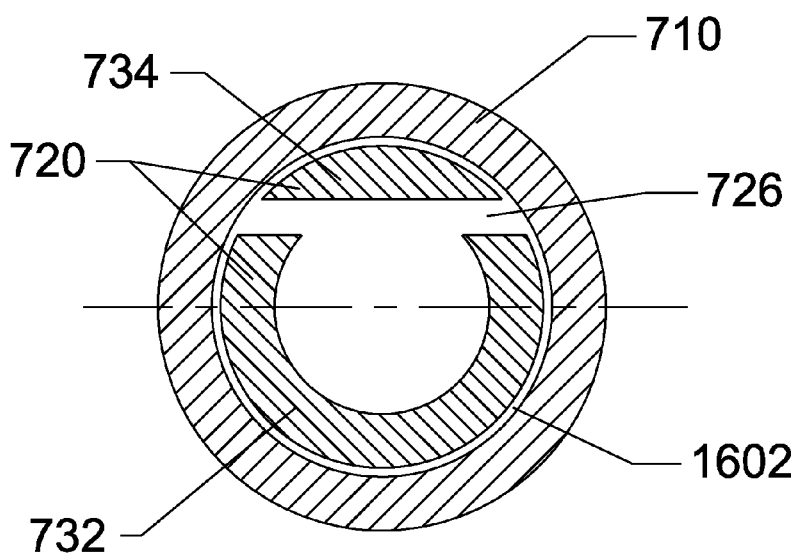
FIG. 16B illustrates a lateral cross-section of a tubing configuration of a steerable transseptal punch within the flexible distal region, with an off-center slot, according to an embodiment of the invention.

FIG. 16B illustrates a lateral cross-sectional view an inner tube 720 nested inside an outer tube 710 and separated from the outer tube 720 by a radial gap 1602 in the flexible region of an articulating septal punch wherein the inner tube 720 is separated by a split or gap 726 into two substantially unequal parts, a connected side 732 and a disconnected side 734, substantially offset from the midline or centerline of the cross-section.

Referring to FIGS. 16A and 16B, the disconnected side 734 is retained in close proximity to the outer tube 710 by its stiffness and its inability to deform such that the edges of the disconnected side 734 can pass beyond the edges of the connected side 732 and thus the two sides 732 and 734 are retained radially displaced from centerline. If the gap 726 were too large or either side 732, 734 were small enough to fit within the edges of the other side, then displacement of one side toward the centerline and confounding of the off-center orientation of the connected side 732 or 734 would occur leading to buckling of the connected side 732 in compression and inability to straighten out a bent transseptal needle. Another problem might be loss of torqueability and predictability of the direction of bending. Both embodiments shown in FIGS. 16A and 16B maintain circumferential and radial orientation of the inner tube connected side 732 relative to the disconnected side 734 and promote high precision deflection of the distal tip.

In preferred embodiments, the radial gap 1602 is minimized and is retained between about 0.0005 to 0.002 inches when the needle is about 0.050 in outside diameter. Furthermore, the split or gap 726 should be as minimal as possible and in preferred embodiments can range from about 0.002 inches to about 0.015 inches with a gap of about 0.004 to 0.010 inches being most preferable.

The embodiments presented in FIGS. 7 through 16 describe a system that does not use pull wires or push rods. There are no side lumens required in either the outer tube or the inner tube. Such side lumens, as found in certain prior art catheters, require extensive cross-sectional area be used to surround the side lumens and take away from the potential area for the central lumen since the outside extent of the catheter is limited. The use of control rods or pull wires requires such as those in certain prior art catheters, retaining these structures along one side of the outer tube so it does not obstruct the lumen, which is needed for stylets, fluid injection, radiopaque dye injection, and the like. Side lumens or channels are necessary to retain a pull wire or control rod in the correct location so as to provide correct off center forces to bend the distal end. The side lumens are also necessary to keep the control rod or pull wires out of the central lumen which needs to remain open and substantially circular. The system disclosed herein, however, retains a high degree of column strength, maximum torqueability, the largest possible central lumen, and a very strong control and steering function or capability. Furthermore, the side lumens or channels are necessary to maintain spatial (rotational orientation) for the articulating distal end of the device. Without the side lumens or channels permitting axial slidability but generating radial retention, the pull wires or pushrods would be free to migrate around within the central lumen of the device and could bend the device in an unwanted direction. Long catheters or needles with relatively small cross-sectional areas are highly subject to torque and rotational misalignment and some method must be employed to retain the correct circumferential location of the articulating apparatus.

Furthermore, a pull-wire as used in prior art devices is incapable of generating compression against the distal end of the device so a pull-wire could not, under compression, move or articulate the distal end of the device. The pull-wire, under tension, can move or articulate the distal end and would require some sort of counterforce such as an opposing pull-wire, shape memory metal, or spring return biasing to move the distal end in the reverse direction. A pull-wire with a diameter of about 0.010 inches (0.0000785 square inches) would sustain tension loads of about 500,000 PSI, to generate a pull force of 40 pounds or 250,000 PSI to generate a pull force of 20 pounds, beyond the capability of most known metals or polymers. Forces exceeding 20 pounds can be necessary to cause bending and stiffening of a Brockenbrough needle to generate the appropriate column strength and bending resistance such that the fossa Ovalis can be penetrated by the needle. A unconstrained push-rod or control rod of almost any diameter will buckle under these types of loads and be unable to generate oppositional forces under compression to articulate the distal end in the reverse direction sufficiently to make the device clinically acceptable.

However, a tubular or cylindrical central control device can maintain its structure in compression, maintain circumferential location within the outer cylindrical, axially elongate tube, maintain precise control, maintain sufficient tensile strength to exert forces up to and exceeding 40 pounds, and maintain a central lumen larger than any other type of steerable device. The resistance to buckling occurs even when the inner tube is slotted longitudinally because the inner tube is constrained within the outer tube using very tight tolerances that will not let the inner tube bend out of its straight orientation, even under compression.

Figure 17A:
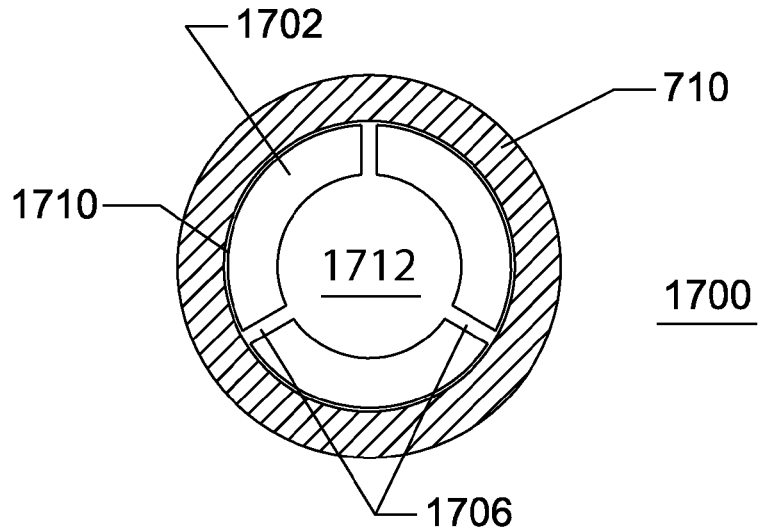
FIG. 17A illustrates a cross-sectional view of a steerable transseptal punch comprising an outer tube and three control rods, each subtending approximately ⅓ of the internal circumference of the outer tube, some or all of which can be functional and each of which is separated from the other by the spacing and all residing within the central lumen of the outer tube, according to an embodiment of the invention.

FIG. 17A illustrates a lateral cross-sectional view of the shaft 1700 of a steerable needle or punch. The shaft comprises an outer tube 710 further comprising a lumen 1710, a plurality of control rods 1702, a plurality of control rod spaces 1706, and a resultant central lumen 1712. The control rods 1702 are slidably disposed within the lumen 1710 outer tube 710, as well as relative to each other. The embodiment illustrated in FIG. 17A has three control rods 1702, which can be pulled from the proximal end of the device to exert compression on the outer tube, and may optionally be stiff enough to be pushed distally within the outer tube to tension the outer tube, or twisted to apply torque to the outer tube. In some embodiments, one or more of the plurality of control rods 1702 can be replaced with keepers. The control rods 1702 are affixed at their distal end to the outer tube, distal to flexible region of the outer tube 710. As illustrated, the control rods are partial cylinders (hollow, in this case, though they may be solid) disposed in the lumen 1712 radially displaced from the remaining control rods. Each control rod extends proximally to a proximal hub (illustrated in FIGS. 8 and 40, for example) and thus remains in a partial cylinder configuration from the proximal hub to the point where it is fixed to the outer tube, distal to the flexible region. Each partial cylinder is characterized by a longitudinal axis, corresponding to the axis of the complete cylinder to which they relate, and each partial cylinder is disposed generally coaxially within the outer tube, such that the longitudinal axis of the outer tube roughly corresponds the longitudinal axes of the partial cylinders, thus leaving the lumen defined by the partial cylinders and/or the outer tube open for passage of stylets, needles, or fluids. Each of the control rods 1702 is retained away from the resultant central lumen 1712 and held substantially against the inner diameter of the outer tube 710 by remaining control rods and the narrow spacing 1706. The three control rods 1702 are configured to provide for steering, deflection, or articulation of the distal end of the steerable needle or punch about multiple axes. Each control rod 1702 can be moved independently, or in concert, along the longitudinal axis under the influence of different actuators, controllers, hydraulic actuators, electrical actuators, pneumatic actuators, levers, knobs, jackscrews, or the like.

The outer tube 710, the control rods 1702, or both, can be fabricated from materials such as, but not limited to, polyimide, polyamide, polyester, polyurethane, silicone, PEEK, PTFE, PFA, FEP, stainless steel, nitinol, titanium, cobalt nickel alloys, and the like.

Figure 17B:
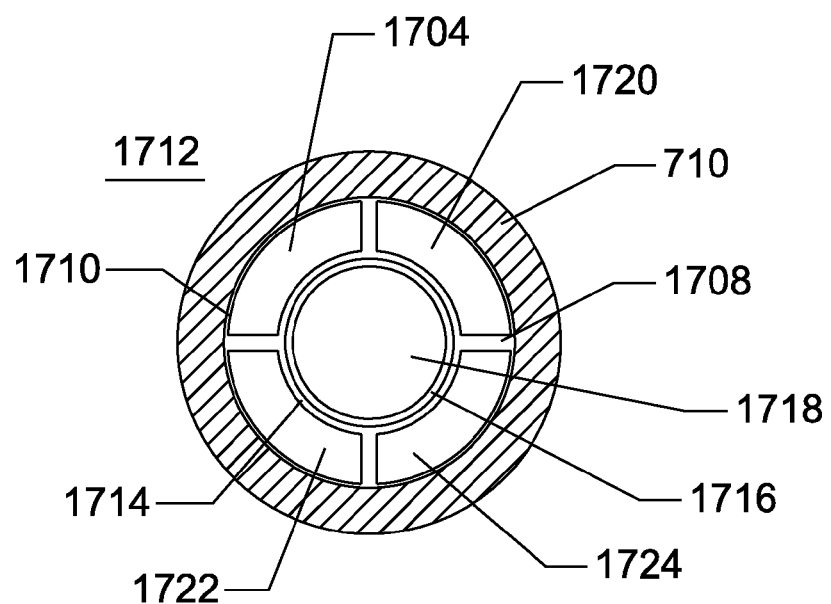
FIG. 17B illustrates a cross-sectional view of a steerable transseptal punch comprising an outer tube and four control rods, each subtending approximately ¼ of the internal circumference of the outer tube, some or all of which can be functional and each of which is separated from the other by the spacing and all residing within the central lumen of the outer tube, and further including an innermost tube to control the fluid path and prevent ingress of egress of fluid from the central lumen of the punch assembly, according to an embodiment of the invention.

FIG. 17B illustrates a lateral cross-sectional view of another embodiment of the shaft 1712 of a steerable needle or punch. The shaft 1712 comprises an outer tube 710 further comprising a lumen 1710, a plurality of rods 1704, 1720, 1722, and 1724, a plurality of rod spaces 1708, and a resultant central lumen 1714. The shaft 1712 further comprises a tubular liner 1716, disposed within the lumen remaining within rods 1704, 1720, 1722, and 1724, which can serve as a fluid-tight barrier, or liner, to prevent the migration fluids into or out of the central lumen 1718 through the side walls of the inner or outer tube in the flexible regions (when the flexible regions are formed with slots as illustrated in the Figures). The liner 1716 can be fabricated from materials such as, but not limited to, polyimide, polyamide, polyester, polyurethane, silicone, PEEK, PTFE, PFA, FEP, stainless steel, nitinol, titanium, cobalt nickel alloys, and the like. The wall thickness of the liner can range from about 0.0005 inches to about 0.010 inches, with a preferred range of about 0.0007 to about 0.005 inches. The liner 1716 can be affixed to the hub (not shown) at the proximal end and to the distal end of the outer tube 710, either directly or through an intermediary structure which could include a bonding ring or at least one of the rods 1704, 1720, 1722, and 1724.

In the device of FIG. 17B, rods 1704 and 1720 are control rods while rods 1722 and 1724 are configured as keepers or stays. As illustrated, the keeper is a partial cylinder (hollow, in this case, though they may be solid) disposed in the lumen 1712 or 1718 radially opposite or displaced from the control rods. The keepers or stays 1722 and 1724 are preferably disconnected from the control rods 1704 and 1720, and not directly attached to the control rods. The keepers or stays 1722 and 1724 can be free-floating within the lumen of the outer tube 710 (not fixedly attached to the outer tube or the control rod), or they may be affixed to the outer tube 710 at the distal end, a point proximal to the flexible region, or a point somewhere intermediate within the flexible region, without being directly fixed to the control rods. The keeper or stay 1722 is preferably disconnected from the other keeper or stay 1724 such that relative axial motion can occur between the two elements.

The two control rods 1704 and 1720 are preferably adjacent to each other but not affixed to each other, again so that relative axial motion can occur between the two elements. The first control rod 1704 is preferably disposed at about 90 degrees, or orthogonal, to the cross-sectional location of the second control rod 1720. The keepers or stays 1722 and 1724 retain the control rods 1704 and 1720 radially outward and away from the center such that the control rods 1704 and 1720 can exert off-center forces on the distal end of the outer tube 710, as well as optionally maintaining a lumen for the passage of fluid, instruments, or the like. The control rods 1704 and 1720 can be affixed to the outer tube 710, at a location approximately distal to the flexible region of the outer tube.

The control rods 1704 and 1720 can be affixed to control mechanisms at the proximal end of the steerable catheter, needle, punch or other axially elongate medical instrument. The control rods 1704 and 1720 are constrained to move axially, or longitudinally, within the outer tube 710, and relative to each other. The keepers or stays 1722 and 1724 preferably do not extend all the way to the proximal end of the steerable medical device but could do so as long as they are not connected to other structures. In some embodiments, proximal to the flexible region, only the control rods 1704 and 1720 would exist and could subtend up to about ½ of the total circumferential arc, each.

In the embodiment shown in FIG. 17B, exerted axial force on control rod 1704, relative to the outer tube 710, can cause bending within a plane running generally midline through the control rod 1704 cross-section. Axial force exerted on the control rod 1720, relative to the outer tube 710, can cause bending within a plane running generally midline through the control rod 1720 arc. Both compression and tension forces can be applied to the control rods 1704, 1720 relative to the outer tube 710 such that bending in both a positive and negative direction can be performed using only a single control rod 1704, 1720, rather than a complementary pair of pull wires, which can operate generally only in tension.

In yet other embodiments, only one of the rods 1704, 1720, 1722, 1724 is a control rod and the other rods are keepers. In yet other embodiments, three or four of the rods operate as control rods for bending or other functions to be transmitted from the proximal end to the distal end of the axially elongate device. In other embodiments, more than four rods are comprised by the device with a realistic maximum of 10 to 20 rods. A major advantage of using a plurality of disconnected rods is maximization of bending and flexion within the device tubing.

Figure 18A:
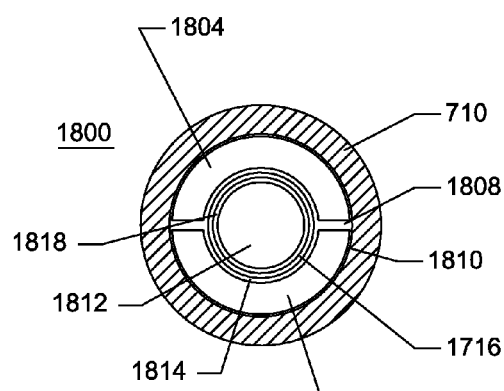
FIG. 18A illustrates a lateral cross-section of a steerable transseptal punch comprising an outer tube, a control rod, a control rod retainer, an internal pressure sleeve to prevent ingress or egress of fluids, and a stylet, according to an embodiment of the invention.

FIG. 18A illustrates a lateral cross-sectional view of another embodiment of the shaft 1800 of a steerable needle or punch. The shaft 1800 comprises the outer tube 710 further comprising a lumen 1810, a control rod 1804, a control rod retainer 1806, guide, or keeper, a plurality of control rod spaces 1808, and a resultant central lumen 1814. The shaft 1800 further comprises a tubular liner 1716, as in FIG. 17A. A stylet 1812 is slidably disposed within the fluid impermeable central lumen 1818. The control rod 1804 is slidably disposed within the lumen 1810 and retained against or near the internal wall of the outer tube 710 by the control rod retainer 1806. The plurality of control rod spaces 1808 between the control rod 1804 and the control rod retainer 1806 are intentionally kept as small as possible without generating excessive friction that would hinder longitudinal relative movement between the control rod 1804 and the control rod retainer 1806, as well as between the control rod 1804 and the outer tube 710. In the illustrated embodiment, the plurality of control rod spaces 1806 are about 0.002 inches wide while the radial distance between the outer wall of the control rod and the inner wall of the inner tube is about 0.001 inches. These spaces could be increased up to, but not beyond, the point where the retaining function of the control rod retainer 1806 is defeated and the control rod 1804 can move laterally into the center of the lumen 1814. The outer tube 710 is shown with a 0.050 inch OD and a wall thickness of about 0.006 inches with a range of about 0.001 to 0.020 inches. The control rod 1804 is illustrated with a wall thickness of about 0.008 inches but can range from about 0.001 to about 0.020 inches.

Figure 18B:
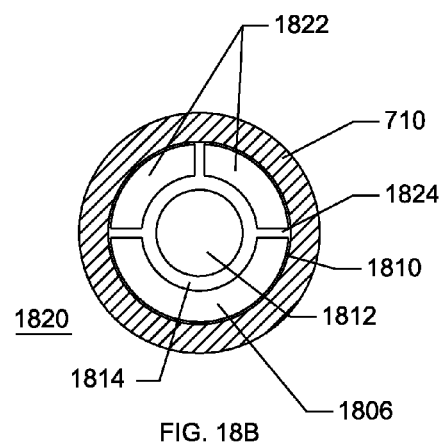
FIG. 18B illustrates a lateral cross-section of a steerable transseptal punch comprising an outer tube, two control rods subtending (together) ½ of the internal circumference of the inner lumen and a control rod retainer subtending ½ of the internal circumference of the outer tube, along with a central stylet, according to an embodiment of the invention.

FIG. 18B illustrates a lateral cross-sectional view of another embodiment of a shaft 1820 of a steerable needle or punch. The shaft 1820 comprises the outer tube 710 further comprising the lumen 1810, two control rods 1822, a control rod retainer 1806, guide, or keeper, a plurality of control rod spaces 1824, and a resultant central lumen 1814. A stylet 1812 is slidably disposed within the central lumen 1814. The control rod retainer 1806 can be affixed at the distal end of the outer tube 710, it can be affixed at a hub (not shown), or it can be affixed to the outer tube at a point intermediate the hub and a flexible region in the outer tube 710. In a preferred embodiment, the control rod retainer 1806 is affixed to the outer tube at one axial location only. In another embodiment the control rod retainer 1806 is not affixed to the outer tube or the inner tube, but rather rides loosely within the outer tube 710 held in place by the control rods 1822. This structure applies to all the control rods and control rod retainers described within this specification.

The two control rods 1822 are affixed at their proximal end to a hub (not shown) or a control mechanism within a hub (not shown) allowing the control rods 1822 to be independently moved longitudinally, or axially, relative to the outer tube 710, under manual or assisted control. Such assisted control includes, but is not limited to, rotational electric motors, pneumatic actuators, stepping motors, linear electric motors, hydraulic actuators, and the like and may further be controlled by computers or other automated control systems. The two control rods 1822 can, in other embodiments, be one or both affixed directly to the hub, or through an intermediary member, such that any relative motion between the control rods and the outer tube is brought about by moving the outer tube by an actuator while the control rods, one or both, remain affixed to the hub, directly or through an intermediary member such as another tube, anchor, fastener, or the like. Affixation can be performed using methods and devices such as, but not limited to, welds, laser welds, silver solder, fasteners, adhesives, mechanical interlock, ultrasonic welds, or the like.

At the distal end, the control rods 1822 can be affixed directly to the outer tube 710 distal to a region of enhanced flexibility or through an intermediary such as a separate tube, linkage, control rod, fastener, or the like. The control rods 1822 can be affixed at a same point or at different locations along the circumference or longitudinal axis of the outer tube 710.

Figure 18C:
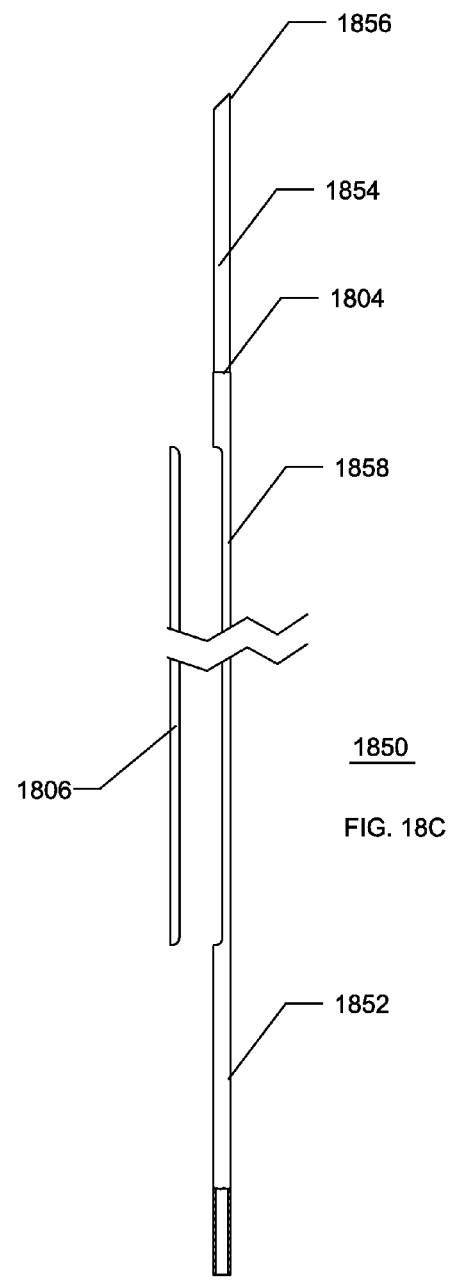
FIG. 18C illustrates a side view of a control rod and keeper system comprising a c-shaped control rod and a c-shaped control rod guide, retainer, or keeper configured to maintain the control rod against the inside diameter of an outer tube and further comprising ends configured for welding and providing a fluid-tight seal with other structures within a punch, according to an embodiment of the invention.

FIG. 18C illustrates a side view of a control rod and keeper system 1850 comprising a c-cross-sectional shaped control rod 1804 (a half-pipe) and a c-cross-sectional shaped control rod keeper 1806 (also a half-pipe). This configuration is shown in lateral cross-section in FIG. 18A. The control rod 1804 can extend or run substantially the entire working length of the steerable needle between a hub (not shown) and a region distal to any deflectable or steerable regions of the outer tube 710 (refer to FIGS. 18A and 18B). The control rod 1804 can also be configured, as shown, to have a C-shape or half-pipe configuration only within the approximate region of a bendable or articulating region of the outer tube 710. In other areas, proximal (1852) and distal (1858) to the flexible region, the control rod 1804 can be a complete tube or cylinder, or it may continue in the half-pipe or partial cylinder configuration for the entire length of the control rod, from its proximal attachment at the proximal hub to the distal attachment to the outer tube. The control rod 1804 is affixed to, or integral to, a distal tubing extension 1854, which can be optionally terminated with a sharp point, as shown, or with a rounded blunt end, with a tapered dilator, or the like. The distal tubing extension 1854 steps up, in the illustrated example, to a larger diameter at the point 1860. The distal tubing extension 1854 can be integral, or affixed to the control rod 1804 or the control rod guide 1806 by a weld, adhesive bond, mechanical fastener, solder joint, brazing joint, or the like.

In the devices of FIGS. 17A through 18C, multi-axis steering is accomplished with the plurality of control rods. These partial cylinder controls rods replace the inner tube of the device of FIGS. 7 through 15, and because the control rods can tension the outer tube at radially displaced point, each control rod can be tensioned to bend the flexible region across a different plane, or in a different radial direction.

The c-shaped control rod guide or retainer 1806 can be completely disconnected from the control rod 1804, or it can be affixed at a point distal to the flexible region, at a point proximal to the flexible region, but not both proximal and distal. In other embodiments, the control rod retainer 1806 can be affixed to the outer tube 710 but not to the control rod 1804. The control rod retainer 1806 serves the function of forcing the control rod 1804 laterally off-center to maintain off-center within the outer tube 710 and for filling the lumen of the outer tube 710 to prevent collapse of the lumen and kinking during articulation or bending.

Figure 19A:
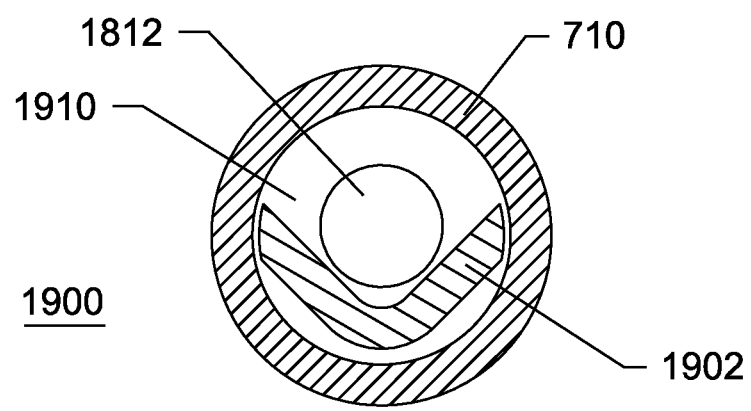
FIG. 19A illustrates a lateral cross section of a steerable transseptal punch comprising an outer tube and a control rod in the shape of a "V" or "L", according to an embodiment of the invention.

FIG. 19A illustrates a lateral cross-sectional view of another embodiment of a shaft 1900 of a steerable needle or punch. The shaft 1900 comprises the outer tube 710 further comprising the lumen 1910, one or more "V" shaped control rod 1902, a resultant central lumen 1910. A stylet 1812 can be slidably disposed within the central lumen 1910. The V-shaped control rod 1902 can be slidably disposed within the lumen 1910 of the outer tube 710 such that it can be axially displaced without substantial resistance, yet it is still constrained against substantial lateral movement due to the space restrictions within the lumen 1910.

Figure 19B:
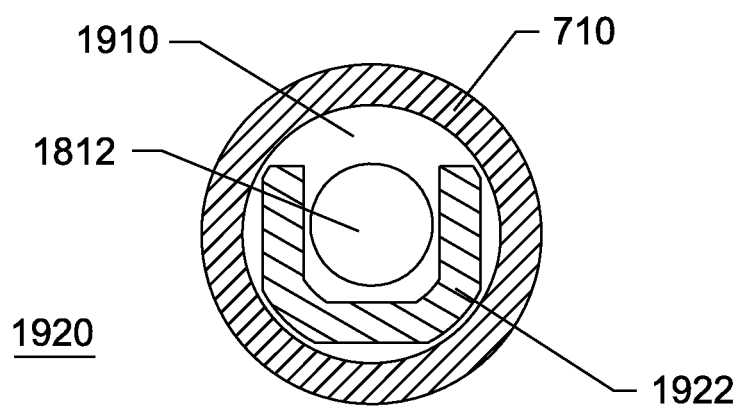
FIG. 19B illustrates a lateral cross section of a steerable transseptal punch comprising an outer tube and a control rod in the shape of a open ended box or "U", according to an embodiment of the invention.

FIG. 19B illustrates a lateral cross-sectional view of another embodiment of a shaft 1920 of a steerable needle or punch. The shaft 1920 comprises the outer tube 710 further comprising the lumen 1910, one or more "U" shaped control rod 1922, a resultant central lumen 1910. The stylet 1812 can be slidably disposed within the central lumen 1910. The U-shaped control rod 1922 can be slidably disposed within the lumen 1910 of the outer tube 710 such that it can be axially displaced without substantial resistance, yet it is still constrained against substantial lateral movement due to the space restrictions within the lumen 1910.

Referring to all the control rods disclosed herein, these control rods can extend the entire length of the device from the hub or handle to a region distal to any flexible regions or regions of enhanced bendability in the outer tube. The control rods can also be affixed or integral to rods, tubing, or other structures extending part way through the device but not traversing the flexible regions or regions of enhanced bendability. The control rods can be affixed to the hub or handle by way of an anchor, weld, adhesive, mechanical interlock, actuator, or the like. The control rods can further comprise hinges or areas of substantially increased flexibility proximate one or both of the ends, proximal and distal.

Figure 20A:
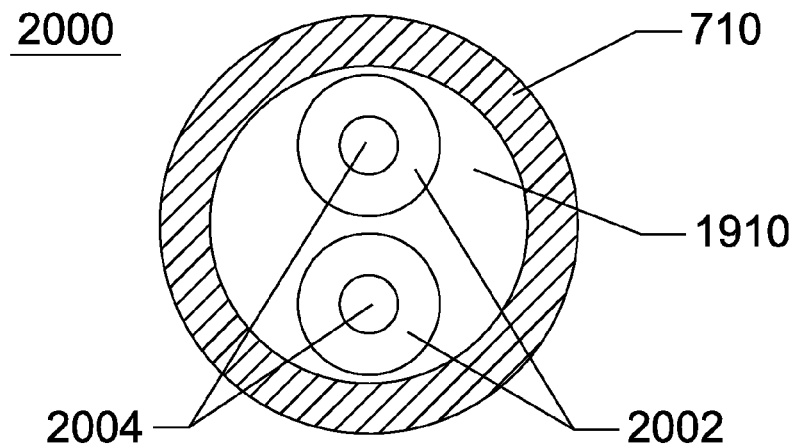
FIG. 20A illustrates a lateral cross section of a steerable transseptal punch comprising an outer tube and two hollow control rods, each of which having a circular cross-section, according to an embodiment of the invention.

FIG. 20A illustrates a lateral cross-sectional view of another embodiment of a shaft 2000 of a steerable needle or punch. The shaft 2000 comprises the outer tube 710 further comprising the lumen 1910, one or more hollow, round control rods 2002, the control rods further comprising a resultant central lumen 2004. This arrangement does not leave room for a large diameter, round stylet but it does provide for a substantial lumen for fluid flow 1910 within the outer tube 710.

Figure 20B:
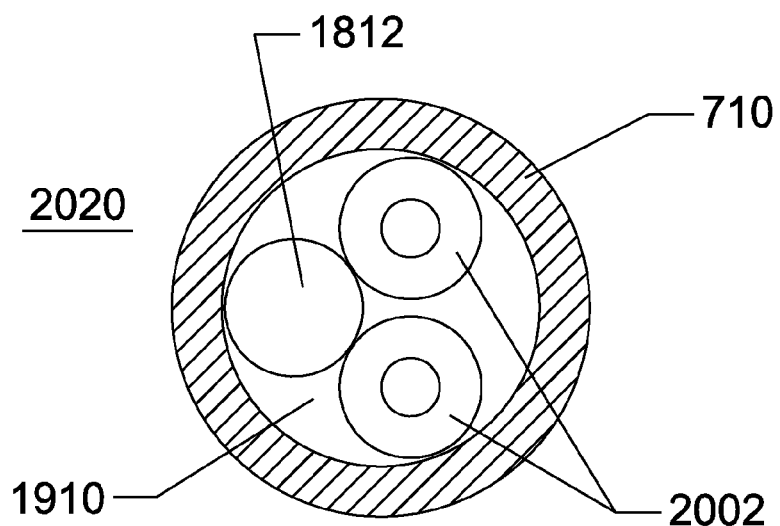
FIG. 20B illustrates a lateral cross section of a steerable transseptal punch comprising an outer tube, two hollow control rods, and a stylet, each of which comprising a circular cross-section, according to an embodiment of the invention.

FIG. 20B illustrates a lateral cross-sectional view of another embodiment of a shaft 2020 of a steerable needle or punch. The shaft 2020 comprises the outer tube 710 further comprising the lumen 1910, one or more hollow, round control rods 2002, and an off-center but full size stylet 1812. This arrangement does provide for a lumen for fluid flow 1910 within the outer tube 710 and the stylet 1812 further provides the function of the control rod retainer, when the stylet 1812 is in place within the lumen 1910.

Figure 21A:
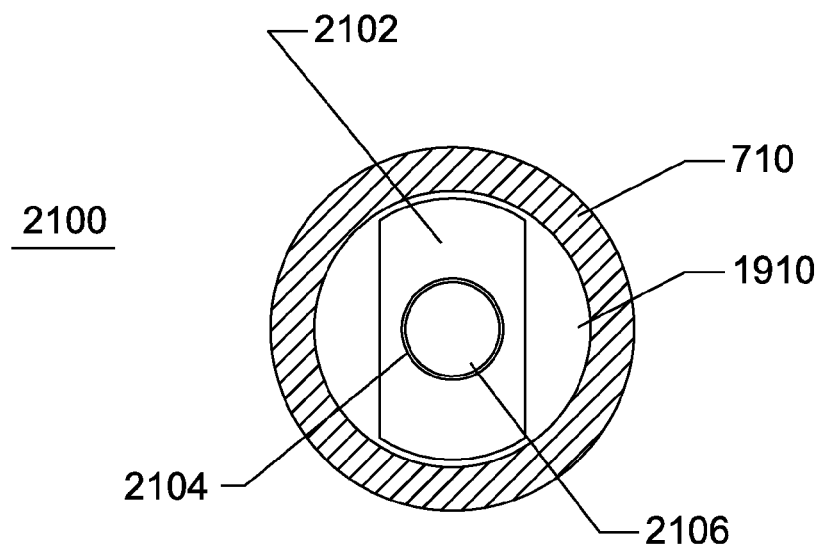
FIG. 21A illustrates a lateral cross section of a steerable transseptal punch comprising an outer tube, a rectangular control rod with rounded ends and a round stylet within a lumen of the control rod, according to an embodiment of the invention.

FIG. 21A illustrates a lateral cross-sectional view of another embodiment of a shaft 2100 of a steerable needle or punch. The shaft 2100 comprises the outer tube 710 further comprising the lumen 1910, a rectangular control rod 2102, the control rod 2102 further comprising a central lumen 2104. A round stylet can be retained within the lumen 2104 and it does provide for a substantial lumen 1910 for fluid flow within the outer tube 710. The distal end of the control rod 2102 can be affixed to the outer tube 710 on one side or another thus generating some offset forces to bend the outer tube 710.

Figure 21B:
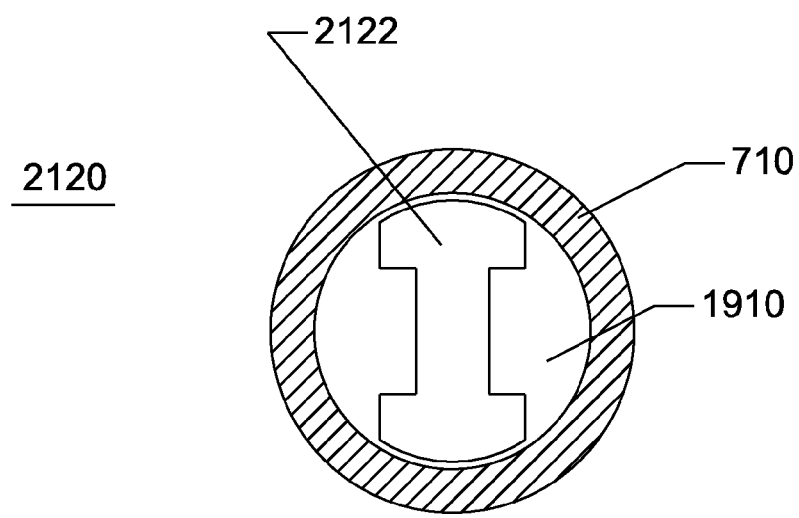
FIG. 21B illustrates a lateral cross section of a steerable transseptal punch comprising an outer tube and an I-beam shaped control rod, according to an embodiment of the invention.

FIG. 21B illustrates a lateral cross-sectional view of another embodiment of a shaft 2120 of a steerable needle or punch. The shaft 2200 comprises the outer tube 710 further comprising the lumen 1910, and an I-Beam shaped control rod 2122. A round stylet cannot be retained within the lumen 1910 but it does provide for a substantial lumen 1910 for fluid flow within the outer tube 710, even greater than that for the embodiment shown in FIG. 21A. Note that the edges of the control rods 2122 and 2102 in FIGS. 21A and 21B are rounded to provide a smoother fit within the lumen 1910, but this rounding, or even part of it, is optional.

Figure 22A:
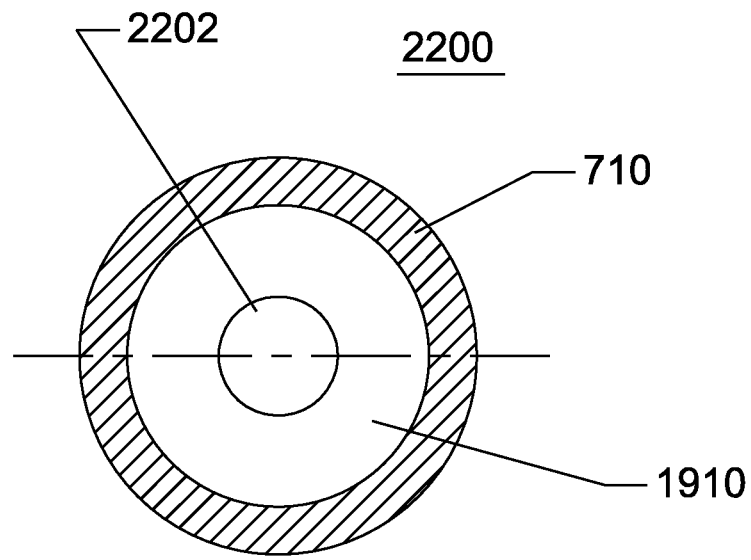
FIG. 22A illustrates a lateral cross section of a steerable transseptal punch comprising an outer tube having a central lumen and a control rod disposed within the central lumen, according to an embodiment of the invention.

FIG. 22A illustrates a lateral cross-sectional view of another embodiment of a shaft 2200 of a steerable needle or punch. The shaft 2200 comprises the outer tube 710 further comprising the lumen 1910, and a round, solid control rod 2202. A round stylet (shown in FIG. 22B) can be retained within the lumen 1910 by moving the control rod 2202 off-center and it does provide for a substantial lumen 1910 for fluid flow within the outer tube 710 but little control over the radial or circumferential position of the control rod within the outer tube 710 is provided.

Figure 22B:
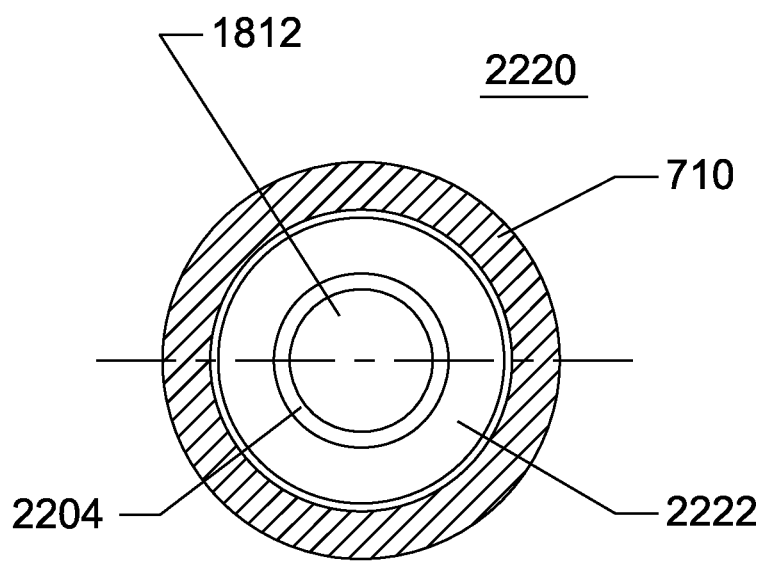
FIG. 22B illustrates a lateral cross section of a steerable transseptal punch comprising an outer tube, a hollow control rod disposed within the lumen of the outer tube, and a stylet disposed within the lumen of the control rod, according to an embodiment of the invention.

FIG. 22B illustrates a lateral cross-sectional view of another embodiment of a shaft 2220 of a steerable needle or punch. The shaft 2220 comprises the outer tube 710 further comprising the lumen 1910, and a round, hollow control rod 2222 further comprising a lumen 2204. The stylet 1812 is retained within the lumen 2204 of the hollow control rod 2222.

Figure 23A:
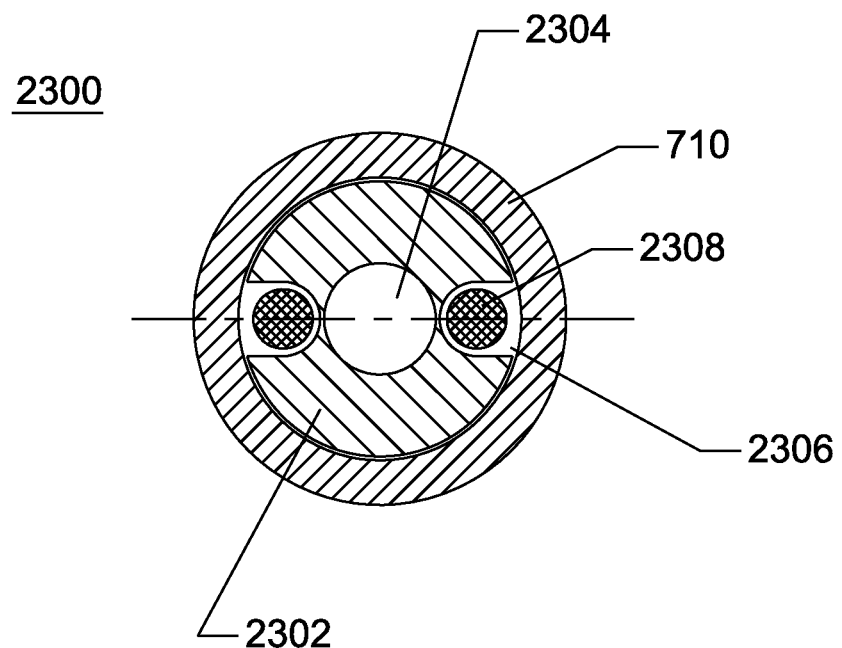
FIG. 23A illustrates a lateral cross section of a steerable transseptal punch comprising an outer tube having a central lumen and a control rod disposed within the central lumen, the control rod having a central lumen and two channels to retain the one or more control wires or rods, according to an embodiment of the invention.

FIG. 23A illustrates a lateral cross-sectional view of another embodiment of a shaft 2300 of a steerable needle or punch. The shaft 2300 comprises the outer tube 710 further comprising the lumen 1910, and a round, hollow control rod retainer 2302 further comprising a central lumen 2304 and a plurality of retainer grooves 2306, and a plurality of control rods or pull wires 2308. A round stylet (shown in FIG. 22B) can be retained within the lumen 2304 but is left out of this illustration. The control rods or pull wires 2308 are illustrated as solid but can comprise structures such as, but not limited to, stranded, tubular, circularly braided, flat braided, continuous tubular, slotted tubular, or the like. The grooves 2306, which can be termed channels, slots, or the like, are beneficially cut or formed into the exterior of the control rod retainer 2302. In other embodiments, these grooves 2306 could be replaced by one or more off-center lumens (not shown) within the cross-section of the control rod retainer 2302. The control rod retainer 2302 can be affixed at one or more points within the outer tube 710 or it can be free floating. The central lumen 2304 is capable of accepting another wire or control rod, a stylet, or fluid.

Figure 23B:
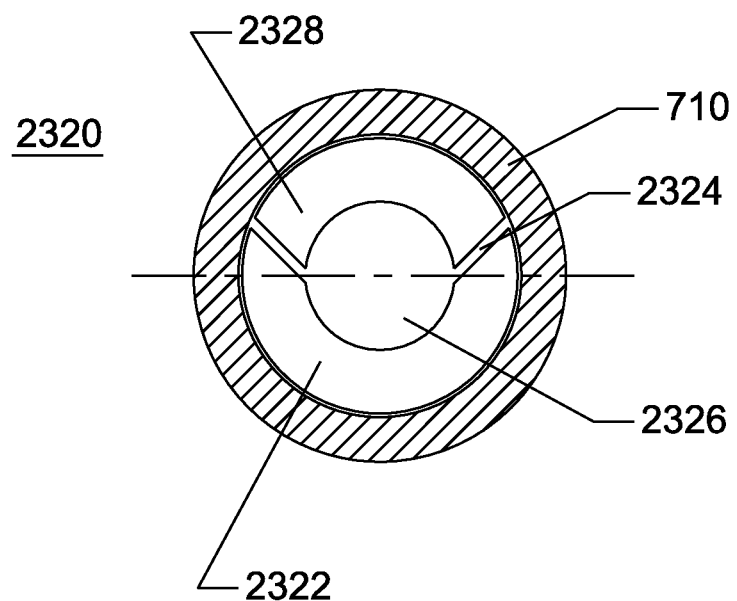
FIG. 23B illustrates a lateral cross section of a steerable transseptal punch comprising an outer tube, a control rod, and a control rod guide, the guide and the control rod being separated by slots formed at an angle other than radial, according to an embodiment of the invention.

FIG. 23B illustrates a lateral cross-sectional view of another embodiment of a shaft 2320 of a steerable needle or punch. The shaft 2320 comprises the outer tube 710 further comprising the lumen 1910, an arcuate or curved, c-shaped control rod retainer 2322 and an arcuate or c-shaped cross-section control rod 2328. The control rod 2328 and the control rod retainer 2322 are separated by a plurality of gaps or spaces 2324. A round stylet (not shown here but shown in FIG. 22B) can be retained within the remaining lumen 2326. The spaces 2324 between the control rod retainer 2322 and the control rod 2328 do not radiate from the center in a radial direction but rather at an angle from the radial direction. The spaces 2324 between the control rod retainer 2322 and the control rod 2328 are drawn at about 0.002 inches spacing but that spacing could be between about 0.0005 and 0.015 inches with a preferable spacing of between about 0.001 and 0.008 inches.

Figure 24A:
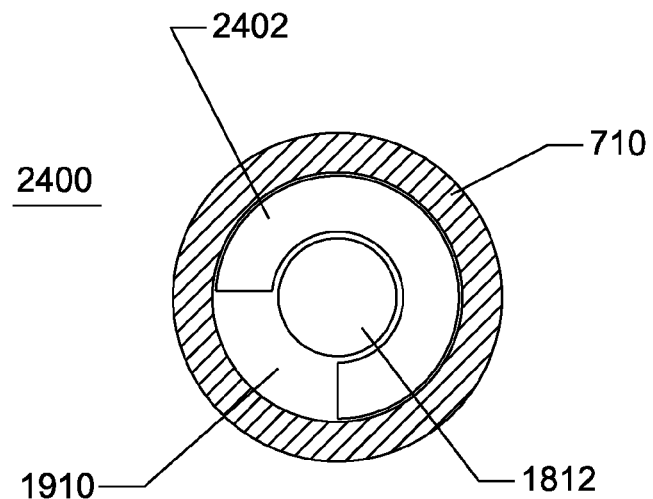
FIG. 24A illustrates a lateral cross section of a steerable transseptal punch comprising an outer tube having a central lumen, a control rod disposed within the central lumen of the outer tube, the control rod having a central lumen and subtending less than a full circle circumferentially, and a central stylet, according to an embodiment of the invention.

FIG. 24A illustrates a lateral cross-sectional view of another embodiment of a shaft 2400 of a steerable needle or punch. The shaft 2400 comprises the outer tube 710 further comprising the lumen 1910, an arcuate or curved control rod 2402 which subtends approximately 270 degrees of circumference on the inside diameter of the outer tube 710. A round stylet 1812 is illustrated as slidably, and removably, retained within the remaining lumen 1910 which is defined by the curvature in the center of the arcuate control rod 2402. The arcuate control rod 2402 is retained against the side wall of the outer tube 710 by its shape, being greater than 180 degrees in circumference. Because the arcuate control rod 2402 is not a full 360 degree control rod, it will have somewhat increased bending and decreased resistance, relative to a fully circular control rod, to lateral forces imposed thereupon.

Figure 24B:
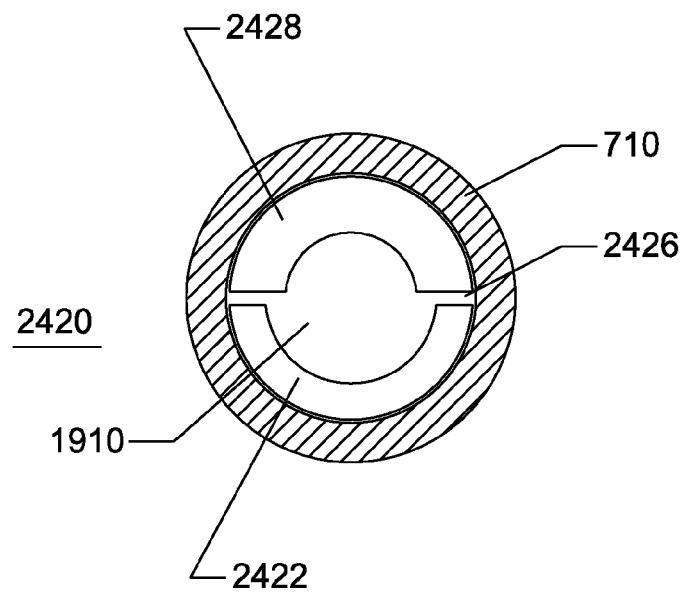
FIG. 24B illustrates a lateral cross section of a steerable transseptal punch comprising an outer tube, a c-shaped control rod, and a control rod guide having thinner wall than the control rod, the guide and the control rod being separated by slots formed radially, according to an embodiment of the invention.

FIG. 24B illustrates a lateral cross-sectional view of another embodiment of a shaft 2420 of a steerable needle or punch. The shaft 2420 comprises the outer tube 710 further comprising the lumen 1910, an arcuate or curved control rod 2428 which subtends approximately 180 degrees of circumference on the inside diameter of the outer tube 710, along with an arcuate control rod retainer 2422 which further subtends approximately 180 degrees within the outer tube 710. A plurality of slits, or slots, 2426 separate the control rod 2428 and the control rod retainer 2422.

The control rod retainer 2422 of FIG. 24B is smaller in wall thickness than that of the control rod 2428 to permit greater fluid flow rates therein and still keep the control rod 2428 against the inside wall of the outer tube 710 and offset from the centerline.

Figure 25A:
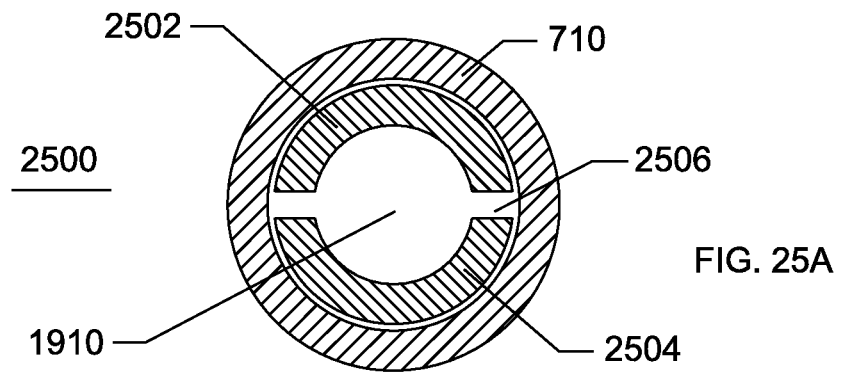
FIG. 25A illustrates a lateral cross section of a steerable transseptal punch comprising an outer tube having a central lumen, a c-shaped control rod disposed within the central lumen of the outer tube, a c-shaped control rod retainer, and narrow slots separating the control rod and the retainer, according to an embodiment of the invention.

FIG. 25A illustrates a lateral cross-sectional view of another embodiment of a shaft 2500 of a steerable needle or punch. The shaft 2500 comprises the outer tube 710 further comprising the lumen 1910, an arcuate or curved control rod 2502 which subtends approximately 180 degrees of circumference on the inside diameter of the outer tube 710, along with an arcuate control rod retainer 2504 which further subtends approximately 180 degrees within the outer tube 710. A plurality of slits, or slots, 2506 separate the control rod 2502 and the control rod retainer 2504. This configuration is similar to that shown in FIG. 18A except that the control rod 2502 and the control rod retainer 2504 subtend a greater arc than the device of FIG. 18A and thus, the gaps 2506 are much smaller, in this case about 0.002 inches and leaving very little room for lateral displacement of the control rod 2502. The outer tube 710, as shown, is an 18 gauge tube with an outside diameter of about 0.050 inches and an inside diameter of about 0.038 inches. This diameter can change to suit the occasion but the concept of tight tolerances between the inner and outer structures is important in retaining alignment and off-center positioning.

Figure 25B:
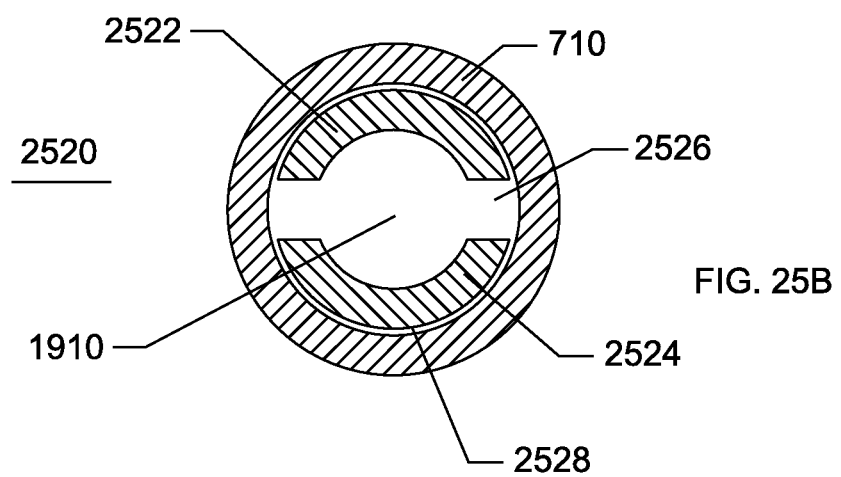
FIG. 25B illustrates a lateral cross section of a steerable transseptal punch comprising an outer tube having a central lumen, a c-shaped control rod disposed within the central lumen of the outer tube, a c-shaped control rod retainer, and medium width slots separating the control rod and the retainer, according to an embodiment of the invention.

FIG. 25B illustrates a lateral cross-sectional view of another embodiment of a shaft 2520 of a steerable needle or punch. The shaft 2520 comprises the outer tube 710 further comprising the lumen 1910, an arcuate or curved control rod 2522 which subtends approximately 180 degrees of circumference on the inside diameter of the outer tube 710, along with an arcuate control rod retainer 2524 which further subtends approximately 180 degrees within the outer tube 710. A plurality of slits, or slots, 2526 separate the control rod 2522 and the control rod retainer 2524. This configuration is similar to that shown in FIG. 25A except that the control rod 2522 and the control rod retainer 2524 subtend a significantly reduced arc than the device of FIG. 25A and thus, the gaps 2526 are much larger, in this case about 0.009 inches and leaving much more room for lateral displacement of the control rod 2522. As in FIG. 25A, the outside arc of the control rod 2522 and the control rod retainer 2524 is a close fit with the inside diameter of the outer tube 710, having only a gap of about 0.001 inches. Since the materials used in all the elements can be metallic, friction from longitudinal relative translation is low and is not a major factor relative to the forces needed to bend the structure.

Figure 25C:
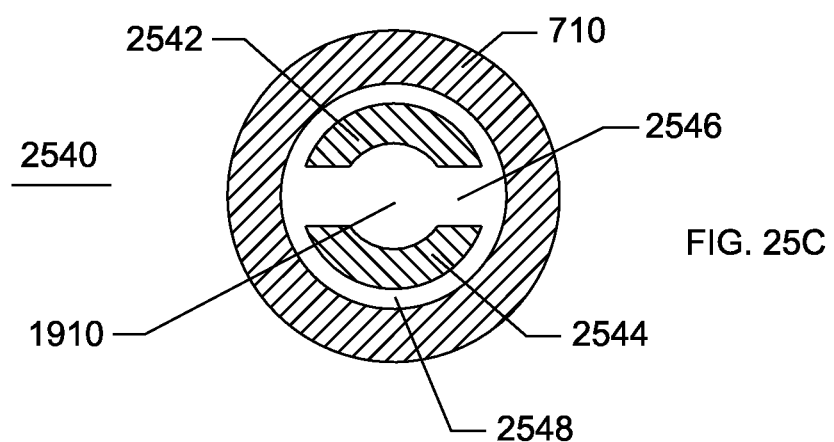
FIG. 25C illustrates a lateral cross section of a steerable transseptal punch comprising an outer tube having a central lumen, a c-shaped control rod disposed within the central lumen of the outer tube, a c-shaped control rod retainer, extremely wide slots separating the control rod and the retainer, and a large gap between the OD of the control rod and retainer and the ID of the outer tube, according to an embodiment of the invention.

FIG. 25C illustrates a lateral cross-sectional view of another embodiment of a shaft 2540 of a steerable needle or punch. The shaft 2540 comprises the outer tube 710 further comprising the lumen 1910, an arcuate or curved control rod 2542 which subtends approximately 180 degrees of circumference on the inside diameter of the outer tube 710, along with an arcuate control rod retainer 2544 which further subtends approximately 180 degrees within the outer tube 710. A plurality of slits, or slots, 2546 separate the control rod 2542 and the control rod retainer 2544. This configuration is similar to that shown in FIG. 25B, with approximately the same slot width 2546, except that the control rod 2542 and the control rod retainer 2544 comprise a significantly reduced outside diameter than the device of FIG. 25B, and thus, the gap 2548 between the control rod 2542 and the inside diameter of the outer tube 710, as well as that of the control rod retainer and the inside diameter of the outer tube 710 are much larger and leave much more room for lateral displacement of the control rod 2542 and the retainer 2544.

Figure 26A:
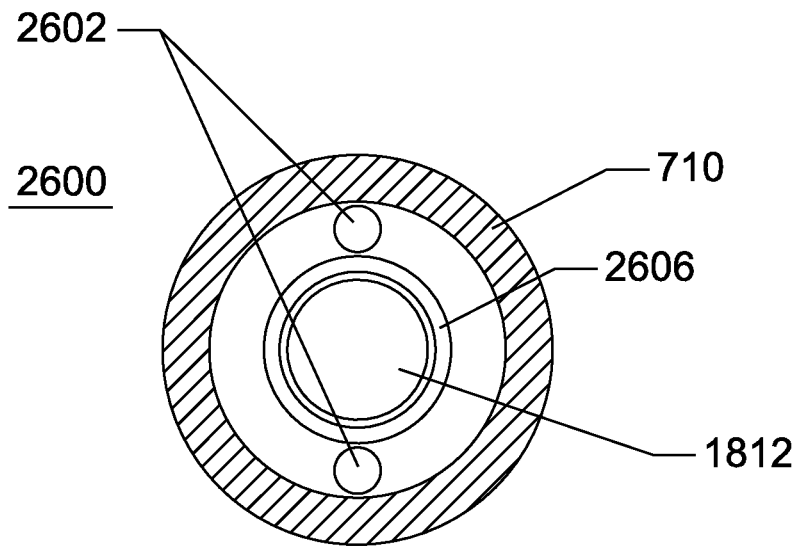
FIG. 26A illustrates a lateral cross section of a steerable transseptal punch comprising an outer tube having a central lumen, a plurality of control rods or wires, an intermediate tube, and a central stylet, according to an embodiment of the invention.

FIG. 26A illustrates a lateral cross-sectional view of another embodiment of a shaft 2600 of a steerable needle or punch. The shaft 2600 comprises the outer tube 710 further comprising the lumen 1910. The shaft 2600 further comprises a plurality of solid control rods or wires 2602, an intermediate or inner tube 2606, and a stylet 1812. The plurality of control rods or wires 2602 ride within the annulus 2610 comprised between the outside of the intermediate or inner tube 2606 and the inside of the outer tube 710.

Figure 26B:
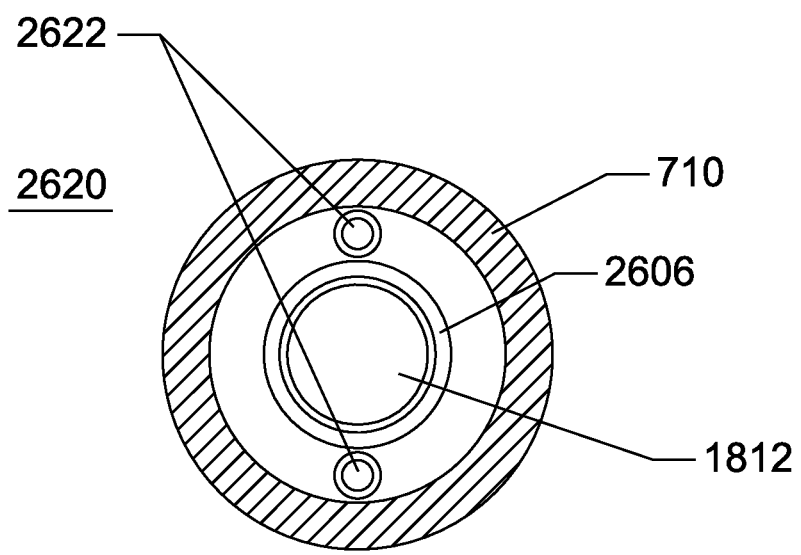
FIG. 26B illustrates a lateral cross section of a steerable transseptal punch comprising an outer tube having a central lumen, a plurality of hollow tubular control rods or wires, an intermediate tube, and a central stylet, according to an embodiment of the invention.

FIG. 26B illustrates a lateral cross-sectional view of another embodiment of a shaft 2620 of a steerable needle or punch. The shaft 2620 comprises the outer tube 710 further comprising the lumen 1910. The shaft 2620 further comprises a plurality of hollow control rods or wires 2622, an intermediate or inner tube 2606, and a stylet 1812. The plurality of control rods or wires 2622 ride within the annulus 2610 comprised between the outside of the intermediate or inner tube 2606 and the inside of the outer tube 710. The hollow control rods or wires 2622 can be tubular in configuration and either solid wall or fenestrated, woven, braided, or the like. The inner tube 1606 restrains the control wires or rods 1606, 2622 radially off-center but does not provide much resistance against circumferential misalignment.

Figure 27A:
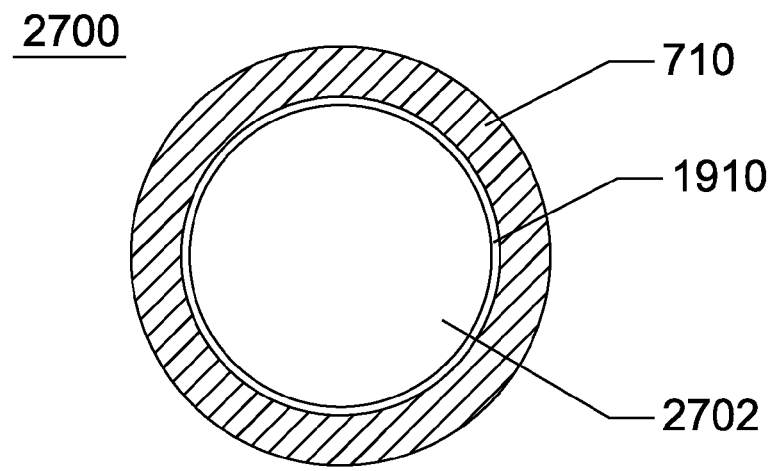
FIG. 27A illustrates a lateral cross section of a steerable transseptal punch comprising an outer tube having a central lumen and a solid central control rod slidably disposed therein, according to an embodiment of the invention.

FIG. 27A illustrates a lateral cross-sectional view of another embodiment of a shaft 2700 of a steerable needle or punch. The shaft 2700 comprises the outer tube 710 further comprising the lumen 1910 and a solid, full diameter control rod 2702 that is slidably disposed or constrained within the lumen 1910 with adequate wall clearance such that minimal friction is encountered but maximum bracing against kinking of the outer tube 710 is provided.

Figure 27B:
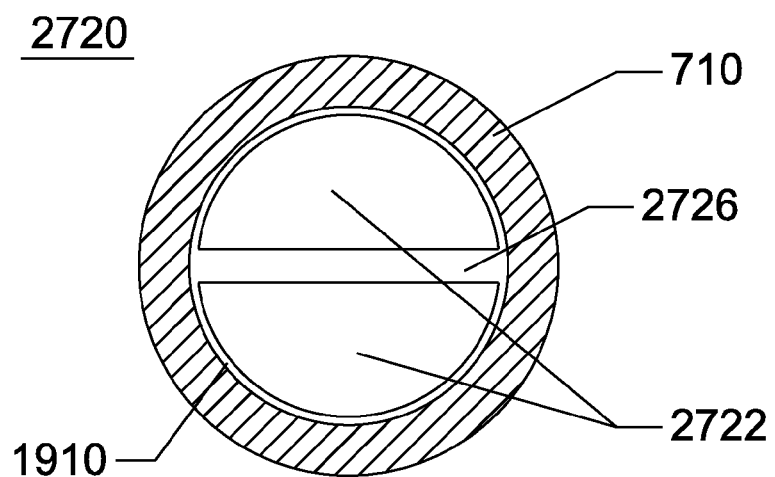
FIG. 27B illustrates a lateral cross section of a steerable transseptal punch comprising an outer tube having a central lumen, a semi-circular first solid control rod, and a semi-circular solid control rod retainer or second control rod, according to an embodiment of the invention.

FIG. 27B illustrates a lateral cross-sectional view of another embodiment of a shaft 2720 of a steerable needle or punch. The shaft 2720 comprises the outer tube 710 further comprising the lumen 1910 and a plurality of solid, partial diameter control rods 2722 that are slidably disposed within the lumen 1910 with adequate wall clearance, and comprise gaps or space 2726 from each other, such that minimal friction is encountered but maximum bracing against kinking of the outer tube 710 is provided. The plurality of control rods 2722 can be hollow or solid. They can be fabricated from tubes, and filling the center, or from a round, solid bar. The central gap 2726 can be fabricated by slotting a tube or bar or by forming the two parts separately.

should be gaps 2806 and 2804

FIG. 28A illustrates a lateral (side) view of a distal, deflectable region 2800 of a steerable needle or punch. The distal deflectable region 2800 comprises the outer tube 2802, with a first plurality of radially directed, partial cuts or gaps 2804 oriented in a first direction, and a second plurality of radially directed partial cuts or gaps 2806 oriented in a second direction. The gaps 2802 and 2804 are formed in the wall such that not all cuts 2802 are grouped together but are, in at least one case, interleaved with the cuts 2804. The distal deflect able region 2800 further comprises a first control rod 1802, a second control rod 1804, and a control rod retainer or keeper 1806, each separated by a plurality of slots 1810. The deflectable region 2800 further comprises the first weld 2814 and the second weld 2812, which axially and radially fix control rods 2806 and 2804 to the outer tube, at a point distal to the flexible region. The two control rods 1802 and 1804 are able to separately apply off-center forces on the outer tube 2802 and, due to the selective ability of the outer tube to bend in the first and second directions, cause the outer tube to flex or articulate in these two directions. The stability of the control rod 1802 allows the second control rod 1804 to flex the tube without closing or opening the gaps 2804 but instead closing or opening the gaps 2806. The same condition is true for the control rod 1804 stabilizing longitudinal movement of the outer tube against opening or closing of the gaps 2806 in a specific direction so that the control rod 1802 can flex the outer tube in the direction of the gaps 2804.

The control rods 1802 and 1804 can be separately affixed to the outer tube 2802 distal to the articulating region or they can be affixed together and to the outer tube 2802 distal to the articulating region. The control rods can be affixed together, to the outer tube, or to an intermediary structure such as another tube using methods such as, but not limited to, welding, soldering, fasteners, mechanical interlock, adhesive bonding, and the like. In the illustrated embodiment, the first control rod 1802 is affixed to the outer tube by the first weld 2814 and the second control rod 1804 is affixed to the outer tube by the second weld 2812. These welds 2812, 2814 can preferably be laser welds or silver soldered joints although the other listed methods can also be used.

FIG. 28B illustrates a cross-section 2820 of the tubing 2800 in the distal articulating region as viewed in the direction shown. The cross-section 2820 comprises the outer tube 2802, the central lumen 1808, the first control rod 1802, the second control rod 1804, the control rod retainer 1806, and the plurality of gaps 1810.

Figures 29A, 29B:
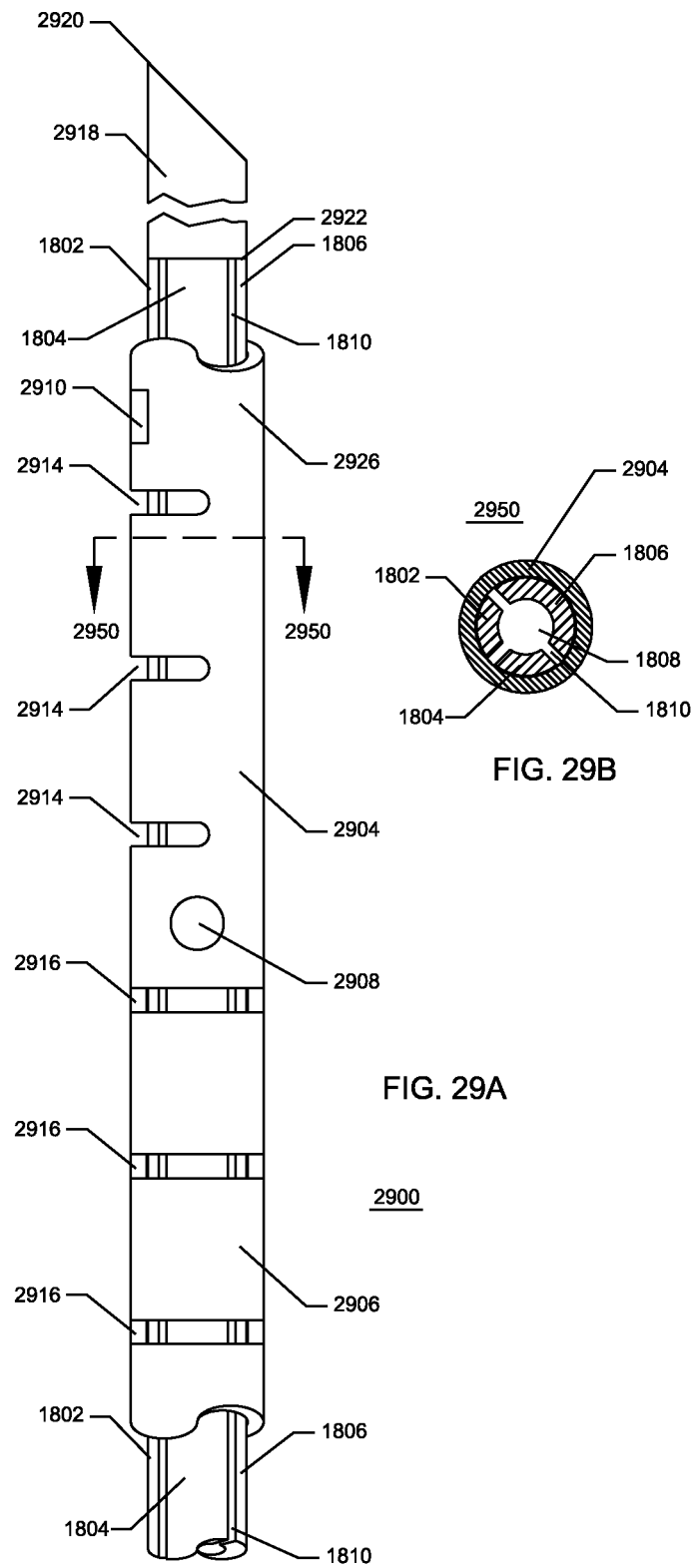
FIG. 29A illustrates a lateral cross section of a steerable transseptal punch comprising an outer tube having a central lumen and a plurality of radially oriented cuts or grooves disposed in two generally orthogonal directions, the different cuts or grooves being placed in order with the grooves in the first direction in a different axial region of the tube than the grooves in the second direction and each defining a flexible region in a specific direction, a plurality of control rods, a plurality of distal weld points, and a control rod retainer, according to an embodiment of the invention.
FIG. 29B illustrates a lateral cross section of the steerable transseptal punch comprising an outer tube having a central lumen, two quarter-circular arcuate control rods, and a semi-circular hollow control rod retainer, according to an embodiment of the invention.

FIG. 29A illustrates a lateral (side) view of a distal, bi-directionally deflectable region 2900 of a steerable needle or punch. The distal bi-directionally deflectable region 2900 comprises a first outer tube region 2906, with a first plurality of radially directed, partial cuts or gaps 2916 oriented in a first direction, a second outer tube region 2904 comprising and a second plurality of radially directed partial cuts or gaps 2914 oriented in a second direction. The cuts or fenestrations 2914 and 2816 are formed in the wall such that all cuts or gaps 2914 or 2916 are grouped together in their respective outer tube regions 2904 and 2906. The distal deflectable region 2900 further comprises a first control rod 1802, a second control rod 1804, and a control rod retainer or keeper 1806, each separated by a plurality of slots 1810. The deflectable region 2900 further comprises the first weld 2908 and the second weld 2910, which are located at different axial locations along the tubing. The distal end of the outer tubing 2918, located axially distal to the deflectable region, is terminated distally by a sharp point 2920 and affixed to one or more of the control rods 1802, 1804, the control retainer 1806, the distal-most outer tube 2926, or one or more of these by a fixation point, arc, or ring 2922, which can be a weld, adhesive bond, solder joint, mechanical fastener, integral fabrication, intermediary structure or the like. The two control rods 1802 and 1804, affixed to the outer tube at different locations immediately distal to their respective articulating regions 2904, 2906 by welds 2910 and 2908, are able to separately apply off-center forces on the outer tube regions 2904 and 2906 and cause the outer tube to flex or articulate in these two directions within their specific locations 2906, 2904. The stability of the control rod 1802, in both compression and tension, allows the second control rod 1804 to flex the 2906 tube without closing or opening the gaps 2914 but instead closing or opening the gaps 2916. The same condition is true for the control rod 1804 stabilizing longitudinal movement of the outer tube against opening or closing of the gaps 2916 in a specific direction so that the control rod 1802 can flex the outer tube in the direction of the gaps 2914.

The control rods 1802 and 1804 are separately affixed to the outer tube distal to their respective articulating. The control rods can be affixed to the outer tube, or to an intermediary structure such as another tube using methods such as, but not limited to, welding, soldering, fasteners, mechanical interlock, adhesive bonding, and the like. In the illustrated embodiment, the first control rod 1802 is affixed to the outer tube by the first weld 2910 and the second control rod 1804 is affixed to the outer tube by the second weld 2908. These welds 2908, 2910 can preferably be laser welds or silver soldered joints although the other listed methods can also be used.

FIG. 29B illustrates a cross-section 2950 of the tubing region 2904 in the distal articulating region as viewed in the direction shown. The cross-section 2950 comprises the outer tube 2904, the central lumen 1808, the first control rod 1802, the second control rod 1804, the control rod retainer 1806, and the plurality of gaps 1810.

Figures 30A, 30B:
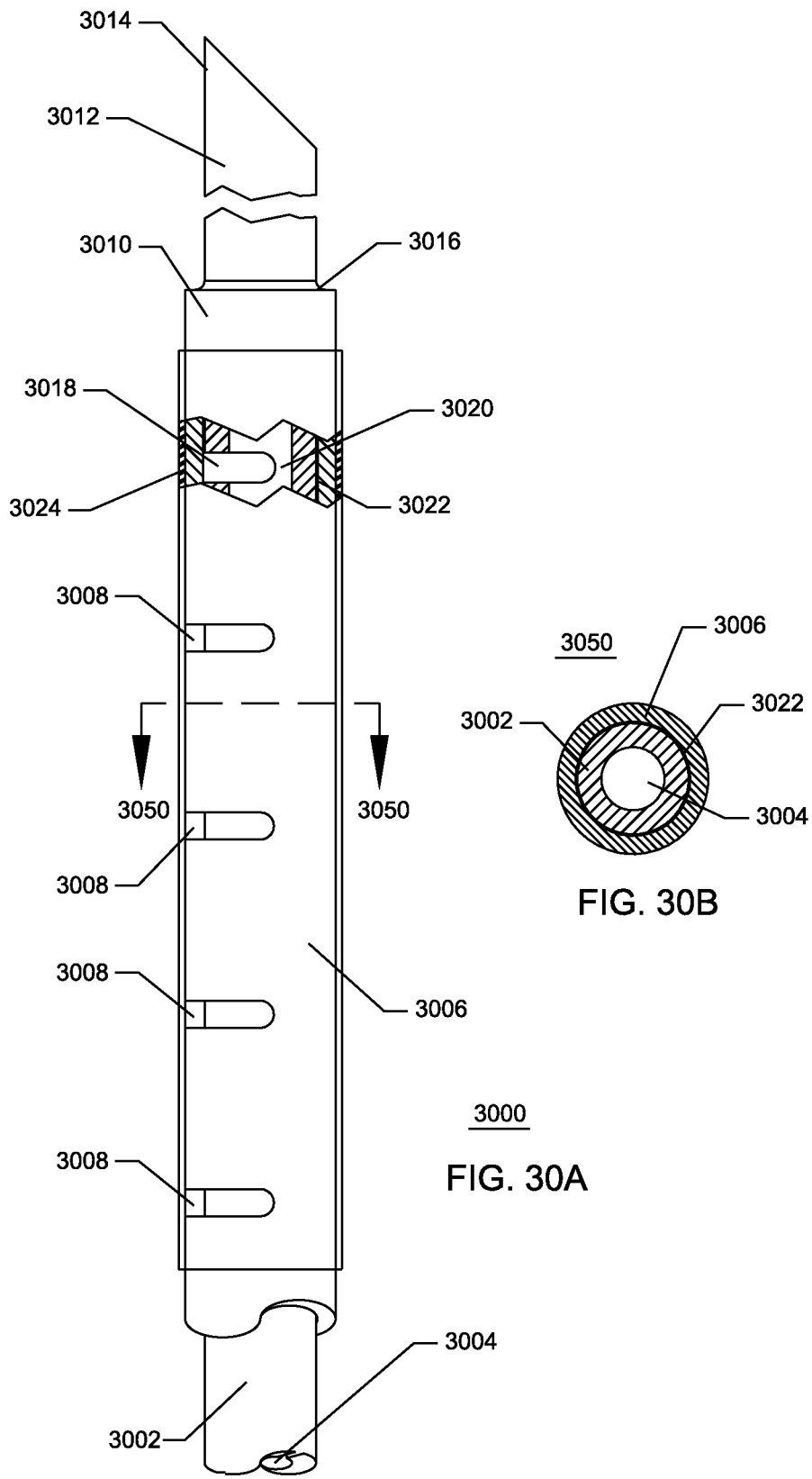
FIG. 30A illustrates a lateral cross section of a steerable transseptal needle comprising an outer tube having a central lumen and a plurality of radially oriented openings, cuts, or grooves disposed in a single direction, defining a flexible region in a specific direction, a hollow circular control rod, a distal weld point between the control rod and the outer tube, a pressure jacket over the openings in the outer tube to prevent fluid leakage or ingress, and a distal hinge on the control rod, according to an embodiment of the invention.
FIG. 30B illustrates a lateral cross section of the steerable transseptal punch comprising an outer tube having a central lumen and a hollow circular, tubular control rod having a central lumen, according to an embodiment of the invention.

FIG. 30A illustrates a lateral (side) view of a distal, bi-directionally deflectable region 3000 of a steerable needle or punch. The distal bi-directionally deflectable region 3000 comprises an outer tube 3006, with a plurality of radially directed, partial cuts or gaps 3008 oriented in a first direction, and further comprising a distal end 3010. The distal region 3000 further comprises a hollow tubular control rod 3002, a central lumen 3004, a distal weld 3016, a tubing extension 3012 optionally terminated by a sharp point 3014, and a hinge region 3020 created, in this embodiment, by a cut 3018 in the control rod 3002. The cuts or fenestrations 3008 are formed in the wall such that all cuts or gaps extend and transect approximately 50% of the diameter of the tube. This transection or cut can range from about 10% to about 90% of the diameter with a preferred range of about 30% to about 70% of the diameter. The transaction can be a simple cut with a rounded end, as illustrated, it can have substantially no rounding, or it can comprise T-slots at the end to facilitate bending depending on the strength of the material and resistance to bending. The transection can comprise a width of about 0.001 to about 0.020 inches with a preferred range of about 0.005 to about 0.015 inches and a most preferred range of about 0.007 to about 0.012 inches. The control rod 3002 can be affixed to the distal-most outer tube 3010, distal to any flexibility enhancing features such as the transections 3008, by a fixation point, arc, or ring 3016, which can be a weld, adhesive bond, solder joint, mechanical fastener, integral fabrication, intermediary structure or the like.

This configuration retains the internal lumen as mostly fluid-tight and leak free, except in the region of the hinge cutout 3018 in the control rod 3002. To prevent leakage through the slots 3008 from the slot 3018, a pressure shroud 3024 is affixed around the exterior of the outer tube. This pressure shroud can comprise, for example, a shrink wrapped or bonded tube of polyester, polyurethane, PTFE, FEP, PFA, or the like. The wall thickness of the pressure shroud 3018 can range from about 0.00025 inches to about 0.010 inches with a preferred range of about 0.0005 to about 0.005 inches and a most preferred range of about 0.0007 to about 0.002 inches. The central lumen 3004 is capable of serving as a leak-free channel for infusion and withdrawal of fluids, both liquid and gas, and can serve as a pressure monitoring lumen, for example, without concern for migration of materials out of, or into, the sides of the device.

The hinge 3020, generated by cutting a notch 3018 in the control rod 3002 is optional. The hinge 3020 could also be fabricated using more standard hinge construction comprising a pin and loops or by the inclusion of materials of elastomeric nature to permit flexing. The partial lateral cuts can be configured so that a given section of outer tube bends more readily in a given direction while another section bends more readily in another, preferably orthogonal, direction. In another embodiment, the cuts in different directions can be interspersed next to each other such that a given flexible region can flex in two directions or planes in the same linear region.

FIG. 30B illustrates a cross-section 3050 of the tubing region 3006 in the distal articulating region as viewed in the direction shown. The cross-section 3050 comprises the outer tube 3006, the central lumen 3004, the hollow control rod 3002, and the gap 3522 between the control rod 3002 and the outer tube 3006. The gap 3522 needs to be enough to prevent binding of the control rod 3002 against the outer tube 3006 during bending. The gap 3006 can be sized radially between about 0.001 and 0.025 inches with a preferred gap of about 0.005 to about 0.020 inches, with a most preferred gap of about 0.010 to 0.015 inches.

FIG. 31A illustrates a side view, in partial breakaway, of the distal end of a steerable transseptal needle 3100 comprising an outer tube 3112, an inner tube 3106, further comprising a lumen 3108 and a blunted distal end 3110, a stylet 3102 further comprising a sharp, pointed, distal end 3104, which is shown retracted inside the lumen 3108, a control rod 3114, and a keeper or stay 3116. The sharp tip 3104 can be formed integrally to the stylet 3102. The sharp tip 3104 can be conical and be sharpened to angles ranging from about 10 degrees to about 60 degrees from the longitudinal axis, per side. The blunted distal end 3110 of the inner tube 3106 can comprise a full round approximately equal to the wall thickness, a taper, a chamfer, or the like. The inner tube 3106 is small in diameter and is difficult to make completely non-sharp but it is blunted to the extent possible. The control rod 3114 is illustrated and extends within the flexible region of the steerable transseptal needle. Sufficient space can exist around the stylet shaft 3102 and within the lumen 3108 to permit fluids to be injected and withdrawn or pressure measurements to be taken. In another embodiment, the stylet wire shaft 3102 can comprise one or more longitudinal slots (not shown) to increase fluid flow area therethrough. The stylet wire or shaft 3102 can also have a star shaped cross-section, a C-shaped cross-section, or the like. The sharp tip 3104 is retracted sufficiently inside the blunted end 3110 that there is no risk of unwanted tissue or guide catheter shaft puncture or damage while the steerable transseptal needle is being advanced or positioned.

FIG. 31B illustrates a side view of the distal end of the steerable transseptal needle 3100 with the stylet 3102 advanced beyond the blunted distal end 3110 of the inner tube to expose the sharp tip 3104. The steerable transseptal needle comprises the outer tube 3112, the inner tube 3106 with the blunted distal end 3110, the stylet 3102, shown advanced, further comprising the sharp, pointed, distal end 3104, the control rod 3114, and the keeper or stay 3116. The sharp tip 3104 is advanced sufficiently to provide for a clean tissue puncture and so that the pierced tissue can ride over the stylet shaft 3102, over the blunted distal end 3110, and onto the outside of the inner tube 3106. Projection of the inner tube 3106 beyond the outer tube 3112 is traditionally about 1.5 cm. This distal projection distance of the inner tube 3106 can be maintained so that the sharp tip 3104 projects beyond the 1.5 cm or the inner tube 3106 projection can be reduced so that the sharp tip 3104 is positioned at approximately 1.5 cm (or less) from the outer tube 3112, when the stylet is fully advanced.

FIG. 32A illustrates a side view, in partial breakaway, of the distal end of a steerable transseptal needle 3200 comprising the outer tube 3112, the inner tube 3106, the lumen 3108 of the outer tube 3112, the blunted distal end 3110, the stylet 3102 further comprising a neck down 3210 to a smaller diameter more proximal stylet shaft 3208, the sharp, pointed, distal end 3104, which is shown retracted inside the lumen 3108, the control rod 3114, the keeper or stay 3116, a radiopaque marker 3202 further comprising a radiopaque marker lumen 3204, and a radiopaque marker retainer 3206. The radiopaque marker 3202 can comprise materials such as, but not limited to, tantalum, platinum, gold, platinum iridium, or the like. The radiopaque marker 3202 is preferably affixed within the lumen 3108 but can, in other embodiments, be affixed to the exterior of the inner tube 3106. The radiopaque marker 3202 can be affixed to the wall of the inner tube 3106, as is, or the inner tube 3106 wall can be machined to create an increased diameter on the ID or a decreased diameter on the OD to accept the radiopaque marker 3202. The radiopaque marker 3202 can be affixed to the inner tube 3106 by welding, adhesive bonding, swaging, a combination thereof, or the like. In an embodiment, the inner tube 3106 can be formed down to a smaller diameter after the radiopaque marker is installed to prevent the radiopaque marker from ever being dislodged.

FIG. 32B illustrates a side, partial breakaway view of the distal end of the steerable transseptal needle 3200 with the stylet 3102 advanced to expose the sharp end 3104 distal to the distal end 3210 of the inner tube 3202. The steerable transseptal needle 3200 comprises the outer tube 3112, the inner tube 3106, further comprising the lumen 3108 and the blunted distal end 3110, the stylet 3102, further comprising the smaller diameter more proximal stylet shaft 3208, the sharp, pointed, distal end 3104, which is shown advanced and exposed beyond the end of the inner tube 3106, the inner tube lumen 3108, the control rod 3114, the keeper or stay 3116, the radiopaque marker 3202 further comprising the radiopaque marker lumen 3204, and the radiopaque marker retainer 3206. The lumen 3204 of the RO marker 3202 is sufficiently large that the stylet wire 3102 can slidably project therethrough with no appreciable drag or binding. The RO marker lumen 3204 should be at least approximately 0.002 inches larger in diameter than the OD of the stylet shaft 3102.

FIG. 33A illustrates a side view, in partial breakaway, of the distal end of a steerable transseptal needle 3300 comprising all the elements of the steerable transseptal needle 3200 of FIGS. 323A and 32B, but wherein the sharp pointed end 3104 of the stylet 3102 is replaced by a beveled, sharp end 3302. The beveled end 3302 can be angled at about 10 degrees to about 60 degrees from the longitudinal axis of the stylet wire 3102. The beveled end 3302 can further comprise one or more facets, not shown.

FIG. 34A illustrates a side view of a stylet hub 3400 comprising the proximal length of stylet wire 3102, the hub body 3402, further comprising a hub lumen 3416, a male Luer taper 3414, and a male Luer lock feature 3412, a spring housing 3404, a push cap 3406, a wire retaining tube 3408, a spring 3410, an O-Ring 3418, and an O-ring retainer 3420. The stylet hub 3400 is shown with the push cap 3406 and its spring container retracted, as biased by the spring 3410. The hub body 3402, the spring housing 3404, the cap 3406, and the O-ring retainer 3420 can comprise plastic such as, but not limited to, polycarbonate, polysulfone, PEEK, PVC, ABS, or the like. The parts can be assembled using adhesive bonding, solvent bonding, ultrasonic welding, interference snap fits, or the like. The spring housing 3404 slides axially over the OD of the hub body 3402 and these two parts are not bonded together. The cap 3406 is affixed to the wire holding tube 3408 using adhesive bonding, a mechanical interference, or the like. The stylet wire 3102 can be affixed to the holding tube 3408 using laser welds, silver solder, crimping, mechanical fasteners, or the like. The O-ring 3418 prevents fluid leakage through the lumen 3416 into the interior of the spring housing 3404 where it could escape and cause patient hemorrhage. Air ingress through the lumen 3416 could also lead to an air embolism and thus needs to be prevented by this O-ring. The spring 3410 can be fabricated from materials such as, but not limited to, stainless steel, nitinol, titanium, cobalt nickel alloy, or the like. In the illustrated embodiment, the spring 3410 is an open coil, when relaxed, but could also be a leaf spring or other spring structure. The spring 3410 biases the hub 3400 to keep the stylet 3102 fully retracted except when activation is required. In the illustrated embodiment, the spring 3410 is fabricated from stainless steel and comprises an OD of 0.25 inches and a wire diameter of about 0.01 to 0.03 inches, with a preferred wire diameter of about 0.015 to 0.014 inches.

FIG. 34B illustrates a side view of the stylet hub 3400 with the spring compressed and the push cap 3406 and its spring housing 3404 fully advanced to compress the spring 3410. The stylet hub 3400 comprises the proximal length of stylet wire 3102, the hub body 3402, further comprising the hub lumen 3416, the male Luer taper 3414, and a male Luer lock feature 3412, the spring housing 3404, the push cap 3406, the wire retaining tube 3408, a the spring 3410. The stylet wire 3102 is now advanced distally due to distal relative motion of the push cap 3406.

Figure 35A:
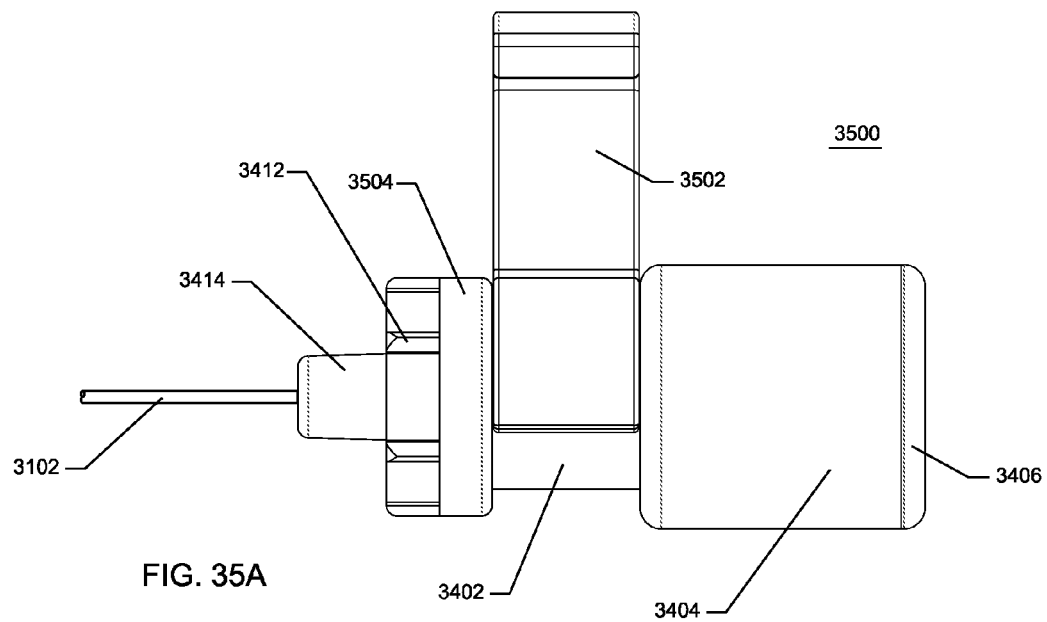
FIG. 35A illustrates a side exterior view of a stylet hub further comprising a removable safety clip, according to an embodiment of the invention.

FIG. 35A illustrates a side view of a stylet hub 3500 comprising the hub body 3402 further comprising the Luer lock feature 3412, the male Luer taper 3414, an enlarged diameter grip 3504 around the male Luer lock feature 3412, the spring housing 3404, the push cap 3406, and a safety clip 3502. The safety clip 3502 resides within the depression created by the spring housing 3404 and the enlargement 3504. The safety clip 3502 comprises a grip region and a c-shaped section that removably snaps around the barrel of the hub body 3402. Thus, the C-shape comprise sufficient opening to permit easy attachment and release of the C-clip 3502 by grasping the grip region or handle. The safety clip 3502 prevents the user from advancing the spring housing 3404 and cap 3406 distally. Once the safety clip is removed, the spring housing 3404 and cap 3406 can move distally, under spring compression, to force the stylet shaft 3102 distally. The safety can comprise other structures that permit such a safety feature. Such safety features can comprise integral switches, control knobs, mechanical interlocks, or the like.

Figure 35B:
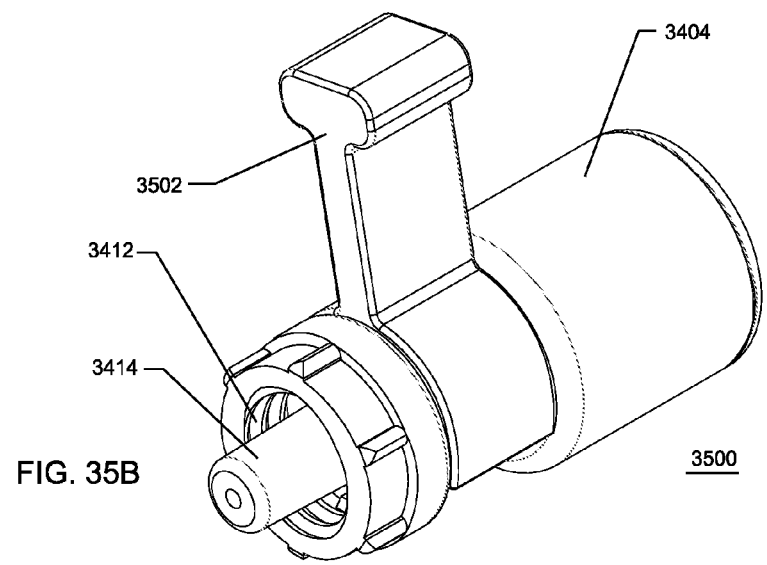
FIG. 35B illustrates the hub of FIG. 35A in oblique view, according to an embodiment of the invention.

FIG. 35B illustrates an oblique view of the stylet hub 3500, comprising the spring housing 3404, the Male Luer lock feature 3412, the male Luer taper 3414, and the removable safety clip 3502. The threads forming the male Luer lock feature 3412 can be clearly seen. These threads interlock with threads on the flange of a female Luer lock connector to form a bayonet mount or screw mount to securely maintain attachment. When fully secured, the hub 3500 or 3400 are positioned precisely with relation to the hub 3500 or 3400 on the steerable transseptal needle (FIG. 36), thus providing for precise locating and function of the stylet tip protrusion distance.

Figure 36A:
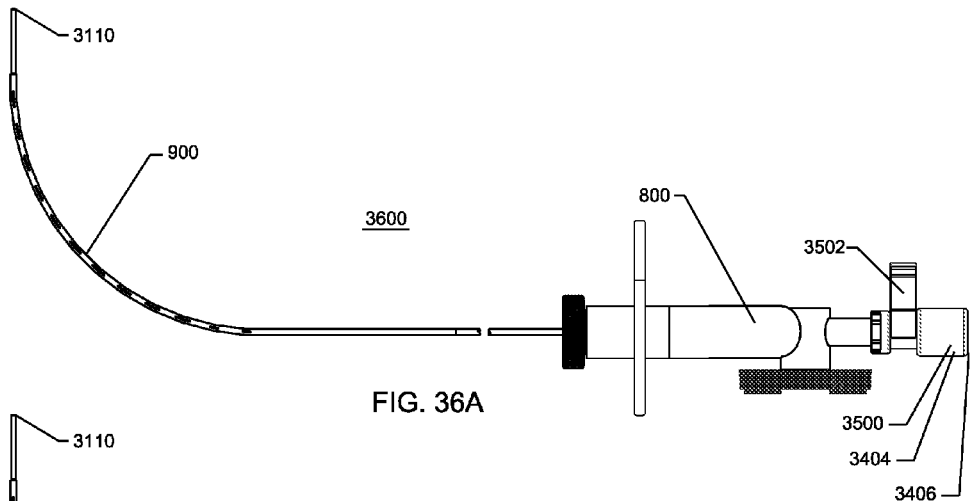
FIGS. 36A, 36B and 36C illustrate side views of a steerable transseptal needle with a piercing stylet hub removably affixed to the proximal end of the needle hub, according to an embodiment of the invention.

FIG. 36A illustrates an exterior side view of a steerable transseptal needle 3600 with its distal end curved 90 degrees. The steerable transseptal needle comprises the stylet 3102 (not shown because it is retracted), the stylet hub 3500, further comprising the stylet hub button 3404 and cap 3406, the safety clip 3502, the flexible region of the needle 900, the steerable transseptal needle hub 800, and the blunted distal end 3110.

Note that the stylet hub 3500 can be released and removed from the hub 800 of the steerable transseptal needle 3600. Although a Luer lock is shown as the preferred attachment, any type of quick connect can be used such as, but not limited to, mechanical fastener, bayonet mount, screw mount, or the like.

Figure 36B:
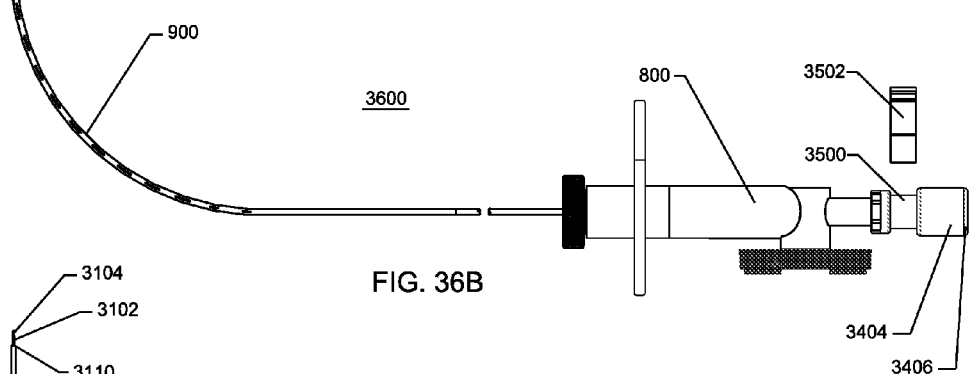

FIG. 36B illustrates the steerable transseptal needle of FIG. 36A with the safety clip 3502 removed but the activation button 3404, 3406 on the stylet hub 3500 has not been advanced or depressed.

Figure 36C:
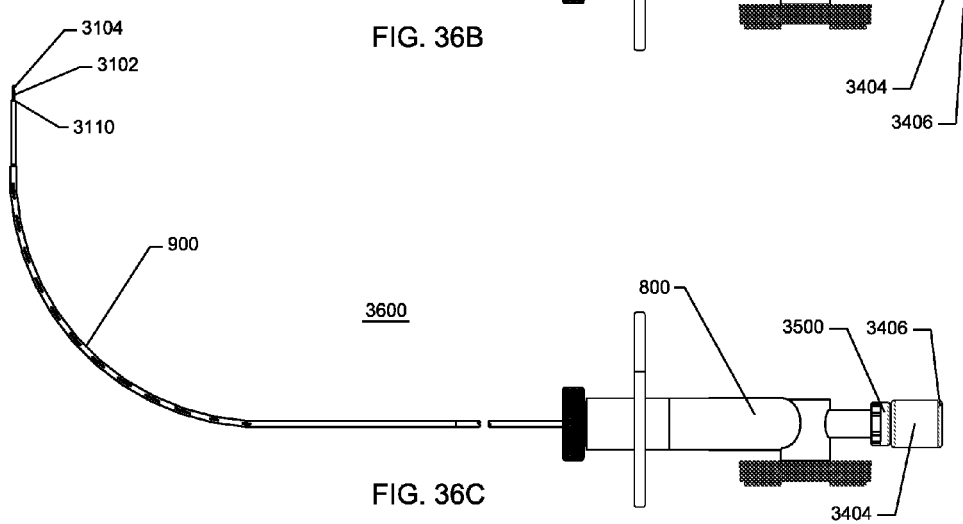

FIG. 36C illustrates the steerable transseptal needle of FIG. 36B with the activation button 3404, 3406 on the stylet hub 3500 having been depressed and causing the stylet 3102, and its sharp tip 3104, to be exposed distally beyond the end 3110 of the inner tube.

In other embodiments, the stylet hub can comprise a quick release feature for the spring. In these embodiments, when a control button is pushed, an intermediate structure is engaged and forces the stylet shaft 3102 distally until a certain point is reached, wherein the intermediate structure is disengaged and the spring forces the stylet shaft 3102 proximally. This disengagement can result from mechanical action that spreads holding features apart sufficiently to release the stylet shaft 3102 and spring 3410. The disengagement can also occur by means of a rotary intermediate device that turns such that the stylet shaft 3102 and spring 3410 lose engagement and are allowed to be biased proximally. In this embodiment, the stylet sharp tip 3104 is never advanced for very long and inadvertent advancement of the structure has less risk of causing damage to critical tissues because the sharp stylet tip 3104 retracts faster than a human can push the device forward.

In yet other embodiments, the hub of the steerable transseptal needle can comprise a side port that is operably connected to the central lumen of the steerable transseptal needle. This side port can be terminated with a female Luer lock and optionally a hemostasis valve or stopcock. This side port can be used to inject or withdraw fluids or to measure pressure while the piercing stylet system is in place and locked onto the proximal end of the steerable transseptal needle.

Figure 37:
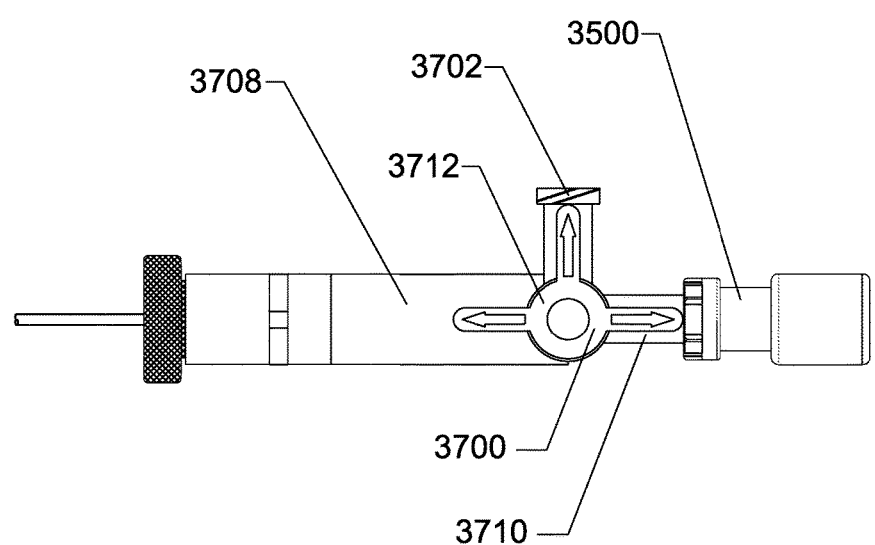
FIG. 37 illustrates a top view of a steerable transseptal needle comprising a three-way stopcock affixed to its hub, rather than the standard one-way stopcock, according to an embodiment of the invention.

FIG. 37 illustrates a top view of a steerable transseptal needle hub body 3708 affixed to a three-way stopcock 3700. The stopcock 3700 comprises a side port 3702 further comprising a lumen (not shown), which is operably connected to the other lumens of the stopcock through the petcock 3712, which allows both the side port 3702 and the proximal through port 3710 to be operably connected to a central lumen (not shown) of the hub 3708. The ends of the stopcock lumens are preferably female Luer lock ports, but could also be regular threaded mounts, quick connects, bayonet mounts, or the like. The piercing stylet hub 3500 is affixed to the Luer threads of the proximal through port 3710.

Figure 38:
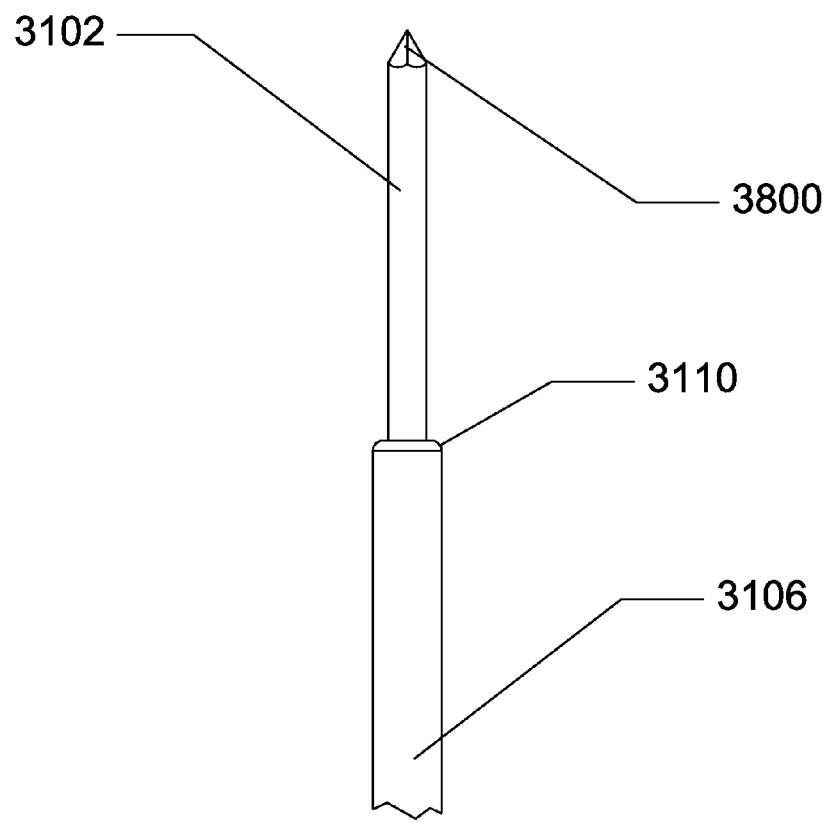
FIG. 38 illustrates a faceted sharp distal end of a piercing stylet, according to an embodiment of the invention.

FIG. 38 illustrates a side view of a faceted sharp distal end 3800 of a piercing stylet 3102. Also illustrated in FIG. 38 are the outer tube 3106 and the blunted, generally laterally cut and rounded distal end 3110 of the outer tube. The number of facets can range from 1 to 10 or more with a preferred number of 2 to 4. Where the stylet tip is not faceted, it can comprise a simple cone or bevel as Illustrated elsewhere. The facets can be cut at an angle of between about 5 and about 45 degrees relative to the longitudinal axis of the stylet 3102.

Figure 39:
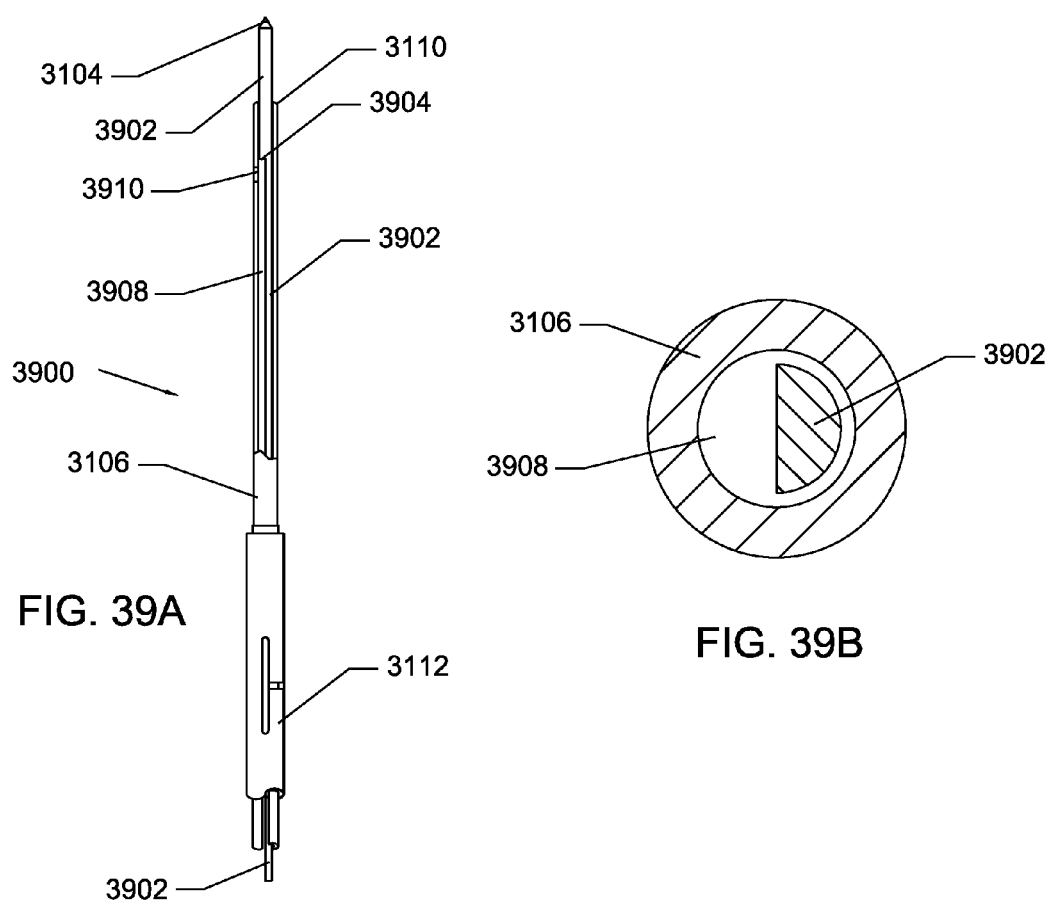
FIG. 39A illustrates a side, partial breakaway view of the distal end of a steerable transseptal needle wherein a portion of the stylet shaft has been cut away to facilitate fluid flow within the central lumen of the steerable transseptal needle, according to an embodiment of the invention.
FIG. 39B illustrates a lateral cross-section of a stylet wire configured to facilitate fluid flow or pressure measurement while the stylet wire is in place within the steerable transseptal needle lumen, according to an embodiment of the invention.

FIG. 39A illustrates a side, partial breakaway view of a steerable transseptal needle comprising a piercing stylet 3900 further comprising a distal shaft 3902, the sharp distal tip 3104, a transition zone 3904, a cutout or cutaway section 3908, and a central shaft 3902. The steerable transseptal needle comprises the inner tube 3106, the outer tube 3112, and the blunted distal end 3110 of the inner tube 3106, and one or more, optional, fenestration, window, opening, or hole 3910 in the side wall of the outer tube. The cutaway region 3908 can run the entire length of the stylet wire or it can terminate at a transition, as shown, to a substantially, completely rounded distal end 3902. The cutaway region 3908 can comprise a partial cylinder, hollow or solid, with a longitudinal axis which is general coaxial with the longitudinal axis of the outer tube, and the inner tube or the several control rods and keepers, and any liner used in the assembly. The cutaway region 3908 can project out the distal end of the inner tube 3106 or it can fully reside within the inner tube 3106 when retracted, extended, or both. Thus, at least a portion of the stylet may be a partial cylinder, or the entire length of the stylet may be a partial cylinder. The window 3910 can permit pressure measurement and fluid injection or removal therethrough when operably in communication with the cutaway region 3908. When an obturator is used in place of the piercing stylet, the structure of the obturator can be similar, with the exception of the sharp tip, to the structure of the stylet.

FIG. 39B illustrates a lateral cross-section of a stylet wire 3900 configured to facilitate fluid flow or pressure measurement while the stylet wire 3900 is in place within the lumen of a steerable transseptal needle. The stylet wire 3900 has had its cross section reduced thus creating a half-moon shaped shaft and creating a half-moon shaped lumen 3908 within the inner tube 3106. The cross-section can be half-moon shaped, as illustrated, or it can be C-shaped, S-shaped, D-Shaped, U shaped, or the like.

Figure 40:
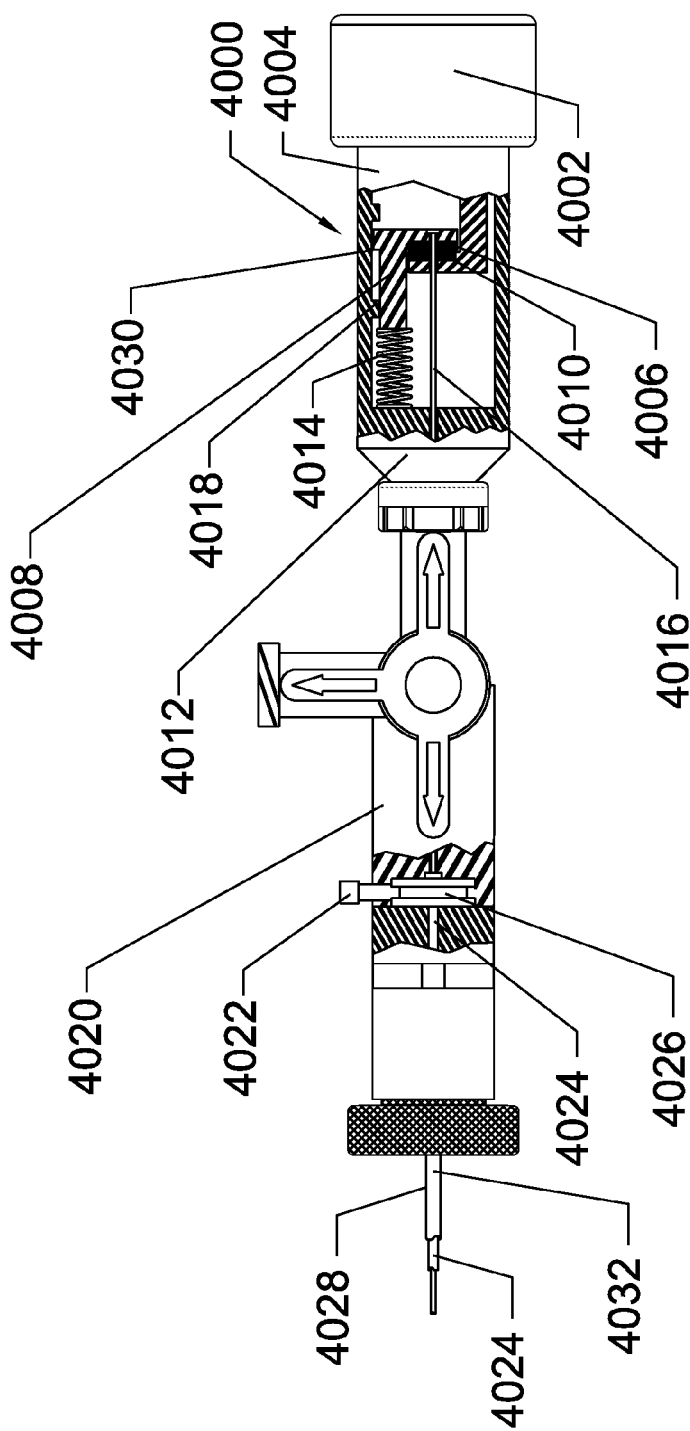
FIG. 40 illustrates a hub of a steerable transseptal needle safety piercing stylet wherein the hub comprises magnetic latches to actuate the stylet, according to an embodiment of the invention.

FIG. 40 illustrates a hub of a steerable transseptal needle safety piercing stylet wherein the hub of the stylet comprises a quick release to actuate, and then retract the stylet. The stylet hub 4000 comprises a push button 4002, a first transmission arm 4004 further comprising a first magnet 4006, a second transmission arm 4008 further comprising a second magnet 4010 and a catch 4030, a stylet hub body 4012 further comprising a stop 4018, a stylet wire 4016 and a return spring 4014. The hub 4020 of the steerable transseptal needle further comprises an electrical connector 4022, operably connected to the inner tubing 4024 or its anchor 4026. The outer tubing of the needle is covered with an insulating jacket 4028.

The stylet wire 4016 is affixed to the first transmission arm 4004. First magnet 4006 is affixed to the first transmission arm 4004 and the second magnet 4010 is affixed to the second transmission arm 4008. The return spring 4014 is operably connected to the first transmission arm 4004 to bias the first transmission arm 4004 proximally away from the second transmission arm 4008. The first 4004 and second 4008 transmission arms as well as the spring 4014 reside with, and are radially constrained within a cavity within the stylet hub body 4012. The spring 4014, as well as the first and second transmission arms 4004 and 4008 can move longitudinally within the cavity of the stylet hub body 4012. The spring 4014 is affixed at one end to the stylet hub body 4012 and to the second transmission arm 4008 such that the spring 4014, at rest, is uncompressed and distal movement of the second transmission arm 4008 forces the spring 4014 into compression from which it wants to recover. The spring 4014 can also be used in tension using an alternative layout. The stop 4018 within the stylet hub body 4012 prevents unwanted distal motion of the second transmission arm 4008 because of the stop 4030 interferes with the catch 4030. This interference forces the first and second transmission arms and their magnets 4006 and 4010 apart after a predetermined travel.

The magnets 4010 and 4006 can comprise materials such as, but not limited to, samarium cobalt, neodymium iron boron, iron, or the like. The magnets can comprise magnifier structures to optimize the magnetic fields. The magnets can be configured, in a preferred embodiment, so that opposite poles come together to provide attraction between the magnets, or wherein like poles come together to provide for repulsive forces.

The electrical connector 4022 is integral or affixed to the anchor 4026 or it can be operably connected and affixed to another metal component, such as the jackscrew traveler (not shown). Application of electrical RF power to the electrical connector 4022 is in electrical communication with the inner tube 4024. A separate ground wire can be applied to the patient. The electrical insulator jacket 4028 is optional but is preferably affixed around the outer tube for its full length or substantially so. Thus the inner tube 4024 ultimately receives the RF energy and is the component that can burn or cauterize tissue. The inner tube 4024 can be blunted, partially, or completely closed off at its distal end to render it maximally atraumatic.

The steerable transseptal needle, in other embodiments, can comprise monitoring systems to measure, display, announce, record, or evaluate operating parameters of the steerable transseptal needle. In an embodiment, the steerable transseptal needle can comprise strain gauges to measure the force being applied by the user to bend the needle. A torque gauge can also be comprised by the system to measure torque being applied to the control knob or the torque being applied by the distal curvature movement. The strain gauge or torque gauge can be affixed within the hub or elsewhere within the steerable transseptal needle to measure compression or tension forces. This information can be displayed in the form of a readout device, such as a digital display of the force or torque. The number of turns can be counted and displayed by, for example, a Hall-Effect sensor, mechanical counter, or the like. In an embodiment, the force or toque can be correlated to the angle of deflection at the distal end, the number of turns applied to the control knob, or both. The readout can be digital or analog and can be affixed to the hub or can be wirelessly received and displayed on external equipment such as a smart phone, computer, tablet computer, panel display, or the like. The wireless technology can, for example, comprise Wi-Fi, Bluetooth®, or other standardized protocols. The human interface can, in other embodiments, comprise audible feedback such as a simple beep or tone, or it can be more sophisticated and provide information using language callouts such as force, turns, torque, or the like.

In operation, the system operates similarly to the standard steerable transseptal needle with a few exceptions. The procedure is to advance a steerable transseptal needle, with a tissue piercing stylet affixed in place, through a transseptal introducer that has already been placed. The steerable transseptal needle is articulated to generate the proper curve, as determined under fluoroscopic or ultrasound guidance. The steerable transseptal needle transseptal introducer assembly is withdrawn caudally out of the superior vena cava and into the right atrium of the heart. Proper location, orientation, tenting, and other features are confirmed. Radiopaque dye can be injected through the steerable transseptal needle to facilitate marking of the fossa ovalis or blood flow around the distal end of the steerable transseptal needle. Pressure measurements can also be taken through the lumen of the steerable transseptal needle to confirm tracings consistent with the right or left atrium of the heart. Once proper positioning has been confirmed, a safety is removed from the stylet hub and a button on the stylet hub is depressed or actuated to cause the sharpened stylet tip to advance out beyond the distal end of the steerable transseptal needle. This sharpened stylet punches through the fossa ovalis and the septal tissue pulls over the stylet, over the inner tube, and over the obturator or dilator of the transseptal introducer. At this point, the sharp stylet is released and retracts proximally within the steerable transseptal needle. The transseptal introducer is now within the left atrium of the heart and the steerable transseptal introducer can be withdrawn from the lumen of the obturator.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A device for penetrating a body lumen or hollow organ of a mammal comprising:
    an outer tube, said outer tube characterized by a distal end, and proximal end, and an outer tube lumen extending from the distal end to the proximal end thereof, said outer tube having a flexible region near the distal end of the outer tube;
    a first control rod disposed with the outer tube, said first control rod characterized by a distal end and a proximal end; wherein said first control rod is fixed to the distal end of the outer tube and extends proximally to the proximal end of the outer tube; and
    a second control rod disposed with the outer tube, said second control rod characterized by a distal end and a proximal end; wherein said second control rod is fixed to the distal end of the outer tube and extends proximally to the proximal end of the outer tube; wherein
    the first control rod and the second control rod comprise partial cylinders disposed coaxially within the outer tube; and
    a fluid impermeable tubular liner disposed within the outer tube lumen, and within the first and second control rods.

2. A device for penetrating a body lumen or hollow organ of a mammal comprising:
- an outer tube, said outer tube characterized by a distal end, and proximal end, and an outer tube lumen extending from the distal end to the proximal end thereof, said outer tube having a flexible region near the distal end of the outer tube;
- a first control rod disposed with the outer tube, said first control rod characterized by a distal end and a proximal end; wherein said first control rod is fixed to the distal end of the outer tube and extends proximally to the proximal end of the outer tube; and
- a second control rod disposed with the outer tube, said second control rod characterized by a distal end and a proximal end; wherein said second control rod is fixed to the distal end of the outer tube and extends proximally to the proximal end of the outer tube; wherein
- the first control rod and the second control rod comprise partial cylinders disposed coaxially within the outer tube; and
- a keeper, comprising a partial cylinder, disposed within the outer tube, in the flexible region, and disposed radially displaced from the first and second control rods, wherein said keeper is not fixed directly to the first control rod or the second control rod.

3. The device of claim 2, wherein the keeper is free-floating within the outer tube.

4. A device for penetrating a body lumen or hollow organ of a mammal comprising:
- an outer tube, said outer tube characterized by a distal end, and proximal end, and an outer tube lumen extending from the distal end to the proximal end thereof, said outer tube having a flexible region near the distal end of the outer tube;
- a control rod disposed with the outer tube, said control rod characterized by a distal end and a proximal end; wherein the control rod is fixed to the distal end of the outer tube and extends proximally to the proximal end of the outer tube, and includes a portion disposed within the flexible region of the outer tube; and
- wherein the portion disposed within the flexible region of the outer tube comprises a partial cylinder; and
- a keeper, comprising a partial cylinder, disposed within the outer tube, in the flexible region, and disposed radially displaced from the partial cylinder of the control rod, wherein said keeper is not fixed directly to the control rod.

5. The device of claim 4, wherein the keeper is free-floating within the outer tube.

6. An apparatus adapted for punching a hole in a body lumen or hollow organ of a mammal comprising:
- an outer tube having a proximal end, a distal end, a longitudinal axis, and a lumen extending therethrough, and a flexible region proximate the distal end;
- an inner tube disposed within the outer tube, said inner tube comprising a partial cylinder along a portion of its length, extending from the proximal end of the outer tube to a proximal end of the flexible region;
- a control rod disposed within the lumen of the outer tube, said control rod extending from the inner tube through the flexible region of the outer tube, said control rod longitudinally fixed to a distal end of the inner tube and longitudinally fixed to the outer tube at a point distal to the flexible region;
- a hub comprising a first portion longitudinally affixed to a proximal end of the inner tube, and a second portion affixed to the proximal end of the outer tube, and said first and second portions are movable relative to each other to tension the inner tube relative to the outer tube.

7. The apparatus of claim 6, further comprising a third tube extending from the control rod, distally, and extending from the distal end of the outer tube.

8. The apparatus of claim 6, further comprising a control rod retainer configured to maintain the control rod off center within the lumen of the outer tube.

9. The apparatus of claim 8, wherein the control rod retainer is integral, or affixed to the control rod in a region distal to the flexible region.

10. The apparatus of claim 8, wherein the control rod retainer is not affixed to the control rod.

11. The apparatus of claim 6, wherein the control rod is affixed to an intermediate structure, which is, in turn, affixed to a hub.

12. The apparatus of claim 6, wherein the outer tube flexible region comprises a slotted portion of the outer tube, and further comprising a pressure jacket disposed exterior to the outer tube to prevent ingress or egress of fluid through the slotted portion of the outer wall.

13. The apparatus of claim 6, further comprising a fluid impermeable tubular liner disposed within the outer tube lumen.

14. The apparatus of claim 6, further comprising a removable obturator or stylet slidably disposed within a central lumen of the inner tube and control rod.

15. The apparatus of claim 14, wherein the obturator or stylet comprises a partial cylinder along at least a portion of its length, and the outer tube has a opening in a sidewall of the outer tube.

16. The apparatus of claim 6, wherein the control rod comprises a V-shaped lateral cross-section.

17. The apparatus of claim 6, wherein the control rod comprises a U-shaped lateral cross-section.

18. The apparatus of claim 6, further comprising a central stylet that is sharpened and configured to punch tissue, said stylet being constrained within a lumen of the inner tube to be retracted within the inner tube until activated, wherein said stylet comprises a primary punching mechanism of the apparatus.

19. The apparatus of claim 18, wherein a stylet hub is affixed to a proximal end of the central stylet, said stylet hub being configured to be releasably affixed to the hub.

* * * * *